(12) United States Patent
Ahmadian et al.

(10) Patent No.: US 7,262,032 B2
(45) Date of Patent: Aug. 28, 2007

(54) ALLELE-SPECIFIC MUTATION DETECTION ASSAY USING AN ENZYME-DISABLING AGENT

(76) Inventors: Afshin Ahmadian, KTH, Royal Institute of Technology, AlbaNova University Center, Dept of Biotechnology, Roslagstullsbacken 21, Stockholm (SE) S-106 91; Joakim Lundeberg, KTH, Royal Institute of Technology, AlbaNova University Center, Dept of Biotechnology, Roslagstullsbacken 21, Stockholm (SE) S-106 91

( * ) Notice: Subject to any disclaimer, the term of this patent is extended or adjusted under 35 U.S.C. 154(b) by 0 days.

(21) Appl. No.: 11/256,694

(22) Filed: Oct. 21, 2005

(65) Prior Publication Data

US 2006/0088872 A1  Apr. 27, 2006

Related U.S. Application Data

(63) Continuation of application No. PCT/GB2004/001766, filed on Apr. 26, 2004.

(30) Foreign Application Priority Data

Apr. 24, 2003 (GB) .................................. 0309350

(51) Int. Cl.
*C12Q 1/68* (2006.01)
*C12P 19/34* (2006.01)
*C12N 15/64* (2006.01)
*C12N 15/66* (2006.01)
*C12N 9/14* (2006.01)

(52) U.S. Cl. .................. 435/91.2; 435/6; 435/91.1; 435/91.41; 435/91.5; 435/91.52; 435/195

(58) Field of Classification Search .................. 435/6, 435/91.1
See application file for complete search history.

(56) References Cited

U.S. PATENT DOCUMENTS

| | | | | |
|---|---|---|---|---|
| 4,654,267 | A | 3/1987 | Ugelstad et al. | ............ 428/407 |
| 5,302,509 | A | 4/1994 | Franklin | ..................... 426/633 |
| 5,338,671 | A | 8/1994 | Scalice et al. | ............. 435/91.2 |
| 5,565,340 | A | 10/1996 | Chenchik et al. | .......... 435/91.2 |
| 5,587,287 | A | 12/1996 | Scalice et al. | .................. 435/6 |
| 6,020,130 | A | 2/2000 | Gold et al. | ..................... 435/6 |
| 6,087,095 | A | 7/2000 | Rosenthal et al. | ............. 435/6 |
| 6,183,998 | B1 * | 2/2001 | Ivanov et al. | ............... 435/91.2 |
| 6,190,865 | B1 * | 2/2001 | Jendrisak et al. | ............... 435/6 |

FOREIGN PATENT DOCUMENTS

| | | |
|---|---|---|
| EP | 0 393 743 A2 | 10/1990 |
| EP | 0 417 842 A2 | 3/1991 |
| EP | 0 592 035 B1 | 1/1996 |
| EP | 0 745 688 A1 | 12/1996 |
| WO | WO98/13523 | 4/1998 |
| WO | WO98/28440 | 7/1998 |
| WO | WO 00/43540 | 7/2000 |
| WO | WO 00/53812 | 9/2000 |
| WO | WO 02/061428 A2 | 8/2002 |
| WO | WO 02/006684 A2 | 9/2002 |
| WO | WO 02/068684 A2 | 9/2002 |

OTHER PUBLICATIONS

Zhou G. et al., "Quantitative detection of single nucleotide polymorphisms for a pooled sample by a bioluminometric assay coupled with modified primer extension reactions (BAMPER)," Oct. 1, 2001, Nucleic Acids Research, 29(19):E93.*

Gerry NP et al., "Universal DNA microarray method for multiplex detection of low abundance point mutations," Sep. 17, 1999, J Mol Biol., 292(2):251-62.*

Landegren U. et al., "Detecting Genes with Ligases," Feb. 1996, Methods, 9(1):84-90.*

Bernard PS. et al., "Homogenous multiplex genotyping of hemochromatosis mutations with fluorescent hybridization probes," Oct. 1998, Am J Pathol., 153(4):1055-61.*

Abu Al-Soud W. et al., "Capacity of nine thermostable DNA polymerases To mediate DNA amplification in the presence of PCR-inhibiting samples," Appl Environ Microbiol, Oct. 1998;64(10):3748-53.*

Lin Y. et al., "Inhibition of multiple thermostable DNA polymerases by a heterodimeric aptamer," J Mol Biol., Aug. 8, 1997;271(1):100-11.*

Ailenberg M. et al., "Controlled hot start and improved specificity in carrying out PCR utilizing touch-up and loop incorporated primers (TULIPS)," Biotechniques, Nov. 2000;29(5):1018-20, 1022-4.*

Afshin Ahmadian et al., "A Brief History Of Genetic Variation Analysis", BioTechniques, vol. 32, No. 5, pp. 1122-1137 (2002).

D. G.Wang et al., "Large-Scale Identification, Mapping, And Genotyping Of Single-Nucleotide Polymorphisms In The Human Genome", Science, vol. 280, (5366) pp. 1077-1082 (1998).

J.N. Hirschhorn et al., "SBE-TAGS: An Array-Based-Method For Efficient Single-Nucleotide Polymorphism Genotyping", Proc. Natl. Acad. Sci., vol. 97, No. 22. pp. 12164-12169 (2000).

(Continued)

*Primary Examiner*—Kenneth R. Horlick
*Assistant Examiner*—Molly E. Baughman
(74) *Attorney, Agent, or Firm*—Winston & Strawn LLP

(57) ABSTRACT

The present invention relates to a method of detecting a base at a pre-determined position in a nucleic acid molecule by performing enzymatic detection reactions using base-specific detection oligomers, where each oligomer is specific for a particular base at the predetermined position, and then comparing the enzymatic detection reactions to determine which base is present at the position, with an enzyme-disabling agent being present during the enzymatic detection reaction. In preferred embodiments the enzymatic detection reaction is an oligomer elongation extension reaction, catalysed by, among others, polymerase or ligase. Also disclosed are methods of performing the assay in a liquid phase and on microarrays.

27 Claims, 17 Drawing Sheets

OTHER PUBLICATIONS

T. Pastinen et al., "A System For Specific, High-Throughput Genotyping By Allele-Specific Primer Extension On Microarrays", Genome Research, vol. 10, No. 7, pp. 1031-1042 (2000).

T. Pastinen et al., "Minisequencing: A Specific Tool For DNA Analysis And Diagnostic On Oligonucleotide Arrays", Genome Research, vol. 7, No. 6, pp. 606-614 (1997).

S. J. Laken et al., "Genotyping By Mass Spectrometric Analysis Of Short DNA Fragments", Nature Biotechnology, vol. 16, No. 13, pp. 1352-1356 (1998).

Afshin Ahmadian et al., "Single-Nucleotide Polymorphism Analysis By Pyrosequencing", Analytical Biochemistry, vol. 280, No. 1, pp.103-110 (2000).

G. Scott Higgins et al., "Competitive Olignucleotide Single-Base Extension Combined With Mass Spectrometric Detection For Mutation Screening", BioTechniques, vol. 23, No. 4, pp. 710-714 (1997).

Newton et al., "Amplification Refractory Mutation System For Prenatal Diagnosis And Carrier Assessment In Cystic- Fibrosis", .The Lancet. vol. 23, No. 30, pp. 1481-1483 (1980).

B. Goergen et al., "Mutation Specific PCR And Direct Solid Phase Sequencing Assay For The Detection Of Hepatitis B Virus Pre-C/C Mutants in Anti-HBe-Positive, Chronic Hepatitis B", Journal of Medical Virology, vol. 43, , No. 1, pp. 97-102 (1994).

Newton et al., "Analysis Of Any Point Mutation In DNA. The Amplification Refractory Mutation System (ARMS)", Nucleic Acids Research, vol. 17, No. 7, pp. 2503-2516 (1989).

S. Ayyadevara et al., "Discrimination of Primer 3'-Nucleotide Mismatch By Taq DNA Polymerase During Polymerase Chain Reaction", Analytical Biochemistry, vol. 284, No. 1, pp. 11-18 (2000).

J. P. Day et al., "Nucleotide Analogs Facilitate Base Conversion With 3' Mismatch Primers", Nucleic Acids Research, vol. 27, No. 8, pp. 1810-1818 (1999).

S. Kwok et al., "Effects Of Primer-Template Mismatches On The Polymerase Chain Reaction: Human Immunodeficiency Virus Type 1 Model Studies", Nucleic Acids Reseach, vol. 18, No. 4, pp. 999-1005 (1990).

Afshin Ahmadian et al., "Genotyping By Apyrase-Mediated Allele-Specific Extension", Nucleic Acids Research, vol. 29, No. 24e121, pp. 1-5 (2001).

D. O'Meara et al., "SNP Typing By Apyrase-Mediated Allele-Specific Primer Extension On DNA Microarrays", Nucleic Acids Research, vol. 30, No. 15e75, pp. 1-8 (2002).

M. Ronaghi et al., "Improved Performance of Pyrosequencing Using Single-Stranded DNA-Binding Protein", Analytical Biochemistry, vol. 286, No. 2, pp. 282-288 (2000).

G. T.Tan et al., "Natural-Product Inhibitors Of Human DNA Ligase I", Biochem. J., vol. 314, pp. 993-1000 (1996)..

P. Nyŕen et al., "Detection Of Single-Base Changes Using A Bioluminometric Primer Extension Assay", Analytical Biochemistry, vol. 244, No. 2, pp. 367-373 (1997).

M. Ronaghi et al., "A Sequencing Method Based On Real-Time Pyrophosphate", Science, vol. 281 (5375), pp. 363-365 (1998).

P. Nyŕen et al., "Enzymatic Method For Continuous Monitoring Of Inorganic Pyrophosphate Synthesis", Analytical Biochemistry, vol. 151, No. 2, pp. 504-509 (1985).

Peter A.C. 't Hoen et al., "Fluorescent Labelling Of cRNA For Microarray Applications", Nucleic Acids Research, vol. 31, No. 5e20, pp. 1-8 (2003).

G. T.Tran et al., "Parallel Genotyping Of Human SNPs Using Generic High-Density Oligonucleotide Tag Arrays", Genome Research, vol. 10, No. 6, pp. 853-860 (2000).

D. O'Meara et al., "Capture Of Single-Stranded DNA Assisted By Oligonucleotide Modules", Analytical Biochemistry, vol. 255, No. 2, pp. 195-203 (1998).

D. O'Meara et al., "Cooperative Oligonucleotides Mediating Direct Capture Of Hepatitis C Virus RNA From Serum", Journal of Clinical Microbiology, vol. 36, No. 9, pp. 2454-2459 (1998).

K.J. Livak et al., "Oligonucleotide With Fluorescent Dyes At Opposite Ends Provide A Quenched Probe System Useful For Detecting PCR Product And Nucleic Acid Hybridization", PCR Methods and Applications, vol. 4, No. 6, pp. 357-362 (1995).

C. Christopherson et al., "The Effects Of Internal Primer-Template Mismatches On RT-PCR: HIV-1 Model Studies", Nucleic Acids Research, vol. 25, No. 3, pp. 654-658 (1997).

S.D. O'Dell et al., "SNP Genotyping By Combination Of 192-Well MADGE, ARMS And Computerized Gel Image Analysis", BioTechniques, vol. 29, No. 3, pp. 500-506 (2000).

E. Huzltin et al., "Competitive enzymatic reaction to control allele-specific extensions", Nucleic Acids Research, vol. 33, No. 5e48, pp. 1-10 (2005).

M. Kaller et al., "Tag-Array Based HPV Genotyping By Competitive Hybridization And Extension",. J Virol Methods, Journal of Virological Methods, vol. 129, No. 2, pp. 102-112 (2005).

Gharizadeh et al. "Viral And Microbial By A Combination Of Muliplex Competitive Hybridization And Specific Extension Followed By Hybridization To Generic Tag Arrays" Nucleic Acids Research, vol. 31, No. 22 e146, pp. 1-12 (2003).

\* cited by examiner

FIGURE 14 - PART 1

FIGURE 14 - PART 2

FIGURE 14 - PART 3

| | Oligonucleotide 1 | Oligonucleotide 2 | Oligonucleotide 3 | Total Nr. of mismatches | | | 3'-terminus mismatch | | | Sum of discriminations | | |
|---|---|---|---|---|---|---|---|---|---|---|---|---|
| | | | | 1 | 2 | 3 | 1 | 2 | 3 | 1 | 2 | 3 |
| HPV73-OLIGO | TAGAAGCACTAATTTTTCTG | TACACAGGCTAGTAGTCT | TGCCAACTCTAATTTTAAGA | 7 | 11 | 12 | yes | yes | yes | yes | yes | yes |
| HPV45-OLIGO | CCGCAGTAGTAATTTAACAT | TACACAAAATCCTGTGCCA | TCGTACTAAGTTTAAGCACT | 4 | 10 | 12 | yes | no | yes | yes | yes | yes |
| HPV40-OLIGO | TCGTAGCACTAATTTAAGCT | CACACAGTCCCCACACCA | TAACAGTAATTTCAAGGAAT | 4 | 7 | 13 | no/yes | no | yes | yes | yes | yes |
| HPV33-OLIGO | TCGGAGTACTAATATGACTT | AGTAACTAGTGACAGTACA | GAATTTTAAAGAATATATAA | 3 | 14 | 17 | yes | yes | yes | yes | yes | yes |
| HPV31-OLIGO | ACGTAGTACCAATATGTCTG | AATTGCAAACAGTGATACT | TAGTAATTTAAAGAGTATT | 7 | 12 | 6 | yes | yes | yes | yes | yes | yes |
| HPV18-OLIGO | TCGCAGTACCAATTTAACAA | TACACAGTCTCCTGTACCT | TGCTACGCAAATTTAAGCAGT | 3 | 7 | 12 | no/yes | yes | yes | yes | yes | yes |
| HPV16-OLIGO | ACGCAGTACAAATATGTCAT | CATATCTACTTCAGAAAGT | TACTAACTTTAAAGAGTACC | 7 | 9 | 6 | yes | yes | yes | yes | yes | yes |
| HPV11-OLIGO | AGGCAGTACAAATATGACAC | TGTGTCTAAATCTGGTACA | AGATTATAAGGAATACATGC | 6 | 12 | 12 | yes | no | no/yes | yes | yes | yes |
| HPV6-OLIGO | ACGCAGTACCAACATGACAT | CGTAACTACATCTTCCACA | TGATTATAAAGAGTAGATGC | 6 | 12 | 16 | yes | yes | no/yes | yes | yes | yes |
| HPV72-OLIGO | TCGCAGTACTAATGTAACTA | CACAGGCGTCCTGTGTATCA | TTCTAATTTTCGTGAGTATC | 7 | 10 | 14 | yes | no | no/yes | yes | yes | yes |
| HPV72-CONSENSUS SEQUENCE | TCGCAGTACTAATGTAACTA | CACAGGCGTCCTCTGTATCA | TTCTAATTTTCGTGAGTATC | | | | | | | | | |
| HPV72-OLIGO | TCGCAGTACTAATGTAACTA | CACAGGCGTCCTGTGTATCA | TTCTAATTTTCGTGAGTATC | 7 | 11 | 12 | yes | yes | yes | yes | yes | yes |
| HPV45-OLIGO | CCGCAGTACTAATTTAACAT | TACACAAAATCCTGTGCCA | TCGTACTAAGTTTCAAGCACT | 8 | 10 | 16 | yes | yes | yes | yes | yes | yes |
| HPV40-OLIGO | TCGTAGCACTAATTTAAGCT | CACACAGTCCCCACACCA | TAACAGTAATTTCAAGGAAT | 8 | 10 | 17 | yes | yes | yes | yes | yes | yes |
| HPV33-OLIGO | TCGGAGTACTAATATGACTT | AGTAACTAGTGACAGTACA | GAATTTTAAAGAATATATAA | 6 | 14 | 16 | yes | yes | yes | yes | yes | yes |
| HPV31-OLIGO | ACGTAGTACCAATATGTCTG | AATTGCAAACAGTGATACT | TAGTAATTTAAAGAGTATT | 7 | 13 | 12 | no | no | yes | yes | yes | yes |
| HPV18-OLIGO | TGCAGTACCAATTTAACAA | TACACAGTCTCCTGTACCT | TGCTACGCAAATTTAAGCAGT | 8 | 7 | 13 | yes | no | yes | yes | yes | yes |
| HPV16-OLIGO | ACGCAGTACAAATATGTCAT | CATATCTACTTCAGAAAGT | TACTAACTTTAAAGAGTACC | 10 | 13 | 11 | yes | yes | yes | yes | yes | yes |
| HPV11-OLIGO | ACGCAGTACAAATATGACAC | TGTGTCTAAATCTGGTACA | AGATTATAAGGAATACATGC | 10 | 16 | 14 | yes | no | yes | yes | yes | yes |
| HPV6-OLIGO | ACGCAGTACCAACATGACAT | CGTAACTACATCTTCCACA | TGATTATAAAGAGTAGATGC | 11 | 14 | 13 | yes | yes | yes | yes | yes | yes |
| HPV73-OLIGO | TAGAAGCACTAATTTTTCTG | TACACAGGCTAGTAGTCT | TGCCAACTCTAATTTTAAGA | | | | | | | | | |
| HPV73-CONSENSUS SEQUENCE | TAGAAGCACTAATTTTTCTG | TACACAGGCTAGTAGTCT | TGCCAACTCTAATTTTAAGA | | | | | | | | | |

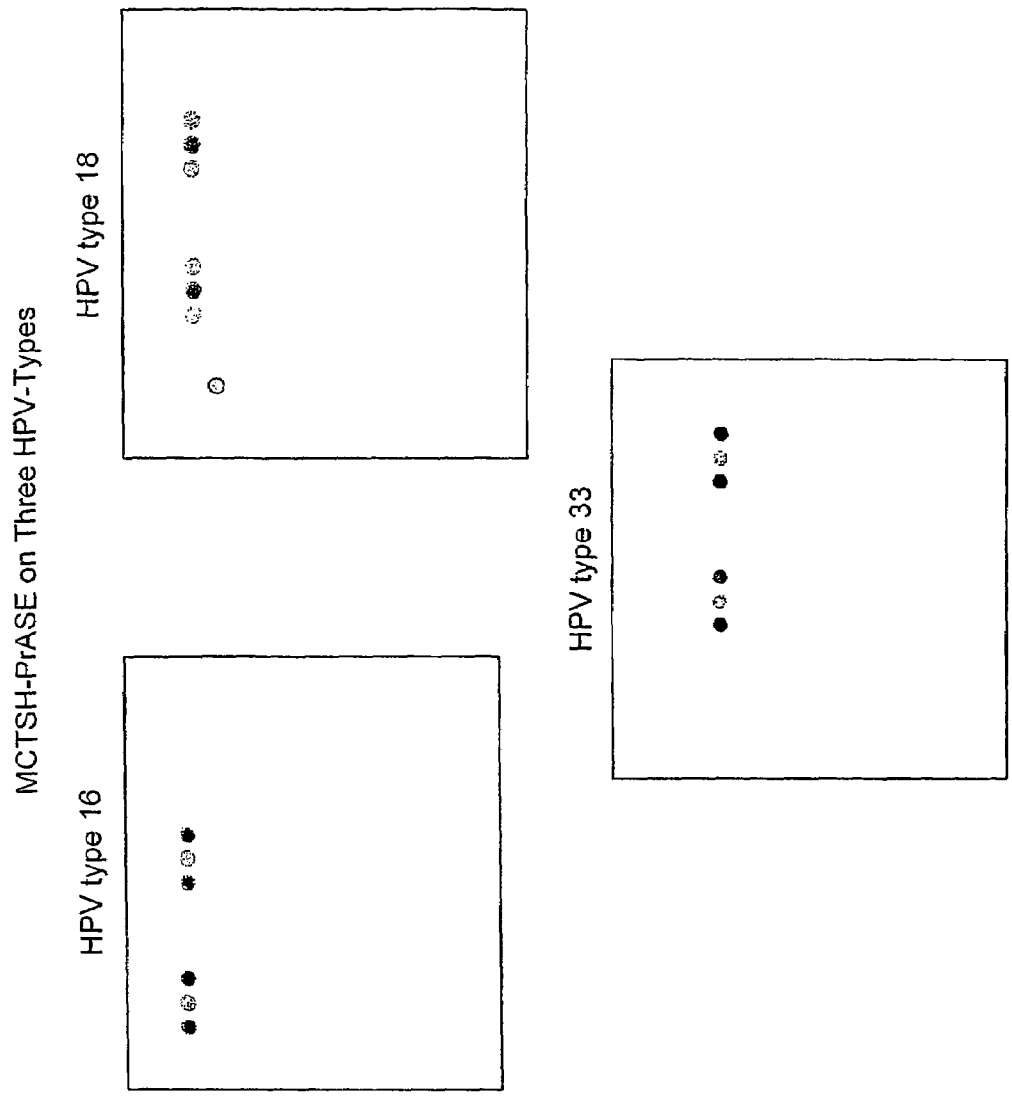

SEQUENCE LISTING

<160> NUMBER OF SEQ ID NOS: 520

<210> SEQ ID NO 1
<211> LENGTH: 60
<212> TYPE: DNA
<213> ORGANISM: artificial
<220> FEATURE:
<221> NAME/KEY: misc_feature
<222> LOCATION: ()..()
<223> OTHER INFORMATION: Oligonucleotide Forward-exon1-wt

<400> SEQUENCE: 1
tgactgagta caaactggtg gtggttggag caggtggtgt tgggaaaagc gcactgacaa        60

<210> SEQ ID NO 2
<211> LENGTH: 56
<212> TYPE: DNA
<213> ORGANISM: artificial
<220> FEATURE:
<221> NAME/KEY: misc_feature
<222> LOCATION: ()..()
<223> OTHER INFORMATION: Oligonucloetide Forward-exon2-wt -continued

```
<400> SEQUENCE: 2
ctgtttgttg gacatactgg atacagctgg acaagaagag tacagtgcca tgagag        56

<210> SEQ ID NO 3
<211> LENGTH: 60
<212> TYPE: DNA
<213> ORGANISM: artificial
<220> FEATURE:
<221> NAME/KEY: misc_feature
<222> LOCATION: ()..()
<223> OTHER INFORMATION: Oligonucleotide Forward-exon1-mutation-in-
      position1-G/T

<400> SEQUENCE: 3
tgactgagta caaactggtg gtggttggag catgtggtgt tgggaaaagc gcactgacaa    60

<210> SEQ ID NO 4
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 4
tttttttttt tttttctggt ggtggttgga gcag                               34

<210> SEQ ID NO 5
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 5
tttttttttt tttttctggt ggtggttgga gcaa                               34

<210> SEQ ID NO 6
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 6
tttttttttt tttttctggt ggtggttgga gcac                               34

<210> SEQ ID NO 7
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer

<400> SEQUENCE: 7
tttttttttt tttttctggt ggtggttgga gcat                               34

<210> SEQ ID NO 8
<211> LENGTH: 34
<212> TYPE: DNA
```

```
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 8
tttttttttt tttttggtg gtggttggag cagg                              34

<210> SEQ ID NO 9
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 9
tttttttttt tttttggtg gtggttggag caga                              34

<210> SEQ ID NO 10
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 10
tttttttttt tttttggtg gtggttggag cagc                              34

<210> SEQ ID NO 11
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 11
tttttttttt tttttggtg gtggttggag cagt                              34

<210> SEQ ID NO 12
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 12
tttttttttt tttttggtgg tggttggagc aggt                             34

<210> SEQ ID NO 13
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 13
tttttttttt tttttggtgg tggttggagc agga                             34
```

```
<210> SEQ ID NO 14
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 14
tttttttttt tttttggtgg tggttggagc aggc                               34

<210> SEQ ID NO 15
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 15
tttttttttt tttttggtgg tggttggagc aggg                               34

<210> SEQ ID NO 16
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 16
tttttttttt tttttgtggt ggttggagca ggtg                               34

<210> SEQ ID NO 17
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 17
tttttttttt tttttgtggt ggttggagca ggta                               34

<210> SEQ ID NO 18
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 18
tttttttttt tttttgtggt ggttggagca ggtc                               34

<210> SEQ ID NO 19
<211> LENGTH: 34
<212> TYPE: DNA
<213> ORGANISM: artificial
<220> FEATURE:
<221> NAME/KEY: misc_feature
<222> LOCATION: ()..()
```

-continued

<223> OTHER INFORMATION: Allele-specific Primer

<400> SEQUENCE: 19
tttttttttt tttttgtggt ggttggagca ggtt                              34

<210> SEQ ID NO 20
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer

<400> SEQUENCE: 20
tttttttttt tttttggtg gttggagcag gtgg                               34

<210> SEQ ID NO 21
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 21
tttttttttt tttttggtg gttggagcag gtga                               34

<210> SEQ ID NO 22
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 22
tttttttttt tttttggtg gttggagcag gtgc                               34

<210> SEQ ID NO 23
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 23
tttttttttt tttttggtg gttggagcag gtgt                               34

<210> SEQ ID NO 24
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 24
tttttttttt tttttggtgg ttggagcagg tggt                              34

<210> SEQ ID NO 25
<211> LENGTH: 34

```
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 25
tttttttttt tttttggtgg ttggagcagg tgga                                34

<210> SEQ ID NO 26
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 26
tttttttttt tttttggtgg ttggagcagg tggc                                34

<210> SEQ ID NO 27
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 27
tttttttttt tttttggtgg ttggagcagg tggg                                34

<210> SEQ ID NO 28
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 28
tttttttttt tttttcgctt tcccaacac cacc                                 34

<210> SEQ ID NO 29
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 29
tttttttttt tttttcgctt tcccaacac caca                                 34

<210> SEQ ID NO 30
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 30
```

```
tttttttttt tttttcgctt tcccaacac cacg                          34
```

<210> SEQ ID NO 31
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 31

```
tttttttttt tttttcgctt tcccaacac cact                          34
```

<210> SEQ ID NO 32
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 32

```
tttttttttt tttttgcgct tttcccaaca ccac                         34
```

<210> SEQ ID NO 33
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 33

```
tttttttttt tttttgcgct tttcccaaca ccaa                         34
```

<210> SEQ ID NO 34
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 34

```
tttttttttt tttttgcgct tttcccaaca ccag                         34
```

<210> SEQ ID NO 35
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 35

```
tttttttttt tttttgcgct tttcccaaca ccat                         34
```

<210> SEQ ID NO 36
<211> LENGTH: 34
<212> TYPE: DNA
<213> ORGANISM: artificial
<220> FEATURE:
<221> NAME/KEY: misc_feature

```
<222> LOCATION: ()..()
<223> OTHER INFORMATION: Allele-specific Primer

<400> SEQUENCE: 36
tttttttttt tttttgcgc ttttcccaac acca                              34

<210> SEQ ID NO 37
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 37
tttttttttt tttttgcgc ttttcccaac accc                              34

<210> SEQ ID NO 38
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 38
tttttttttt tttttgcgc ttttcccaac accg                              34

<210> SEQ ID NO 39
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 39
tttttttttt tttttgcgc ttttcccaac acct                              34

<210> SEQ ID NO 40
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 40
tttttttttt tttttgtgcg cttttcccaa cacc                             34

<210> SEQ ID NO 41
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 41
tttttttttt tttttgtgcg cttttcccaa caca                             34

<210> SEQ ID NO 42
```

```
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 42
tttttttttt ttttgtgcg cttttcccaa cacg                              34

<210> SEQ ID NO 43
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer

<400> SEQUENCE: 43
tttttttttt ttttgtgcg cttttcccaa cact                              34

<210> SEQ ID NO 44
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 44
tttttttttt ttttagtgc gcttttccca acac                              34

<210> SEQ ID NO 45
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 45
tttttttttt ttttagtgc gcttttccca acaa                              34

<210> SEQ ID NO 46
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 46
tttttttttt ttttagtgc gcttttccca acag                              34

<210> SEQ ID NO 47
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 47
```

-continued ttttttttt tttttagtgc gcttttccca acat    34

<210> SEQ ID NO 48
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 48
tttttttttt ttttcagtg cgcttttccc aaca    34

<210> SEQ ID NO 49
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 49
tttttttttt ttttcagtg cgcttttccc aacc    34

<210> SEQ ID NO 50
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 50
tttttttttt ttttcagtg cgcttttccc aacg    34

<210> SEQ ID NO 51
<211> LENGTH: 34
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer

<400> SEQUENCE: 51
tttttttttt ttttcagtg cgcttttccc aact    34

<210> SEQ ID NO 52
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 52
tttttttttt tttttcatac tggatacagc tggac    35

<210> SEQ ID NO 53
<211> LENGTH: 35
<212> TYPE: DNA
<213> ORGANISM: artificial
<220> FEATURE:

```
<221> NAME/KEY: misc_feature
<222> LOCATION: ()..()
<223> OTHER INFORMATION: Allele-specific Primer

<400> SEQUENCE: 53
tttttttttt tttttcatac tggatacagc tggaa                         35

<210> SEQ ID NO 54
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 54
tttttttttt tttttcatac tggatacagc tggag                         35

<210> SEQ ID NO 55
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 55
tttttttttt tttttcatac tggatacagc tggat                         35

<210> SEQ ID NO 56
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 56
tttttttttt tttttatact ggatacagct ggaca                         35

<210> SEQ ID NO 57
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 57
tttttttttt tttttatact ggatacagct ggacc                         35

<210> SEQ ID NO 58
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 58
tttttttttt tttttatact ggatacagct ggacg                         35
```

```
<210> SEQ ID NO 59
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 59 ttttttttt tttttatact ggatacagct ggact                                35

<210> SEQ ID NO 60
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 60 ttttttttt ttttttactg gatacagctg gacaa                                35

<210> SEQ ID NO 61
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 61 ttttttttt ttttttactg gatacagctg gacac                                35

<210> SEQ ID NO 62
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 62 ttttttttt ttttttactg gatacagctg gacag                                35

<210> SEQ ID NO 63
<211> LENGTH: 35
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 63 ttttttttt ttttttactg gatacagctg gacat                                35

<210> SEQ ID NO 64
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer
```

-continued

```
<400> SEQUENCE: 64
tttttttttt tttttcatgg cactgtactc ttcttg                              36

<210> SEQ ID NO 65
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 65
tttttttttt tttttcatgg cactgtactc ttctta                              36

<210> SEQ ID NO 66
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 66
tttttttttt tttttcatgg cactgtactc ttcttc                              36

<210> SEQ ID NO 67
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 67
tttttttttt tttttcatgg cactgtactc ttcttt                              36

<210> SEQ ID NO 68
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 68
tttttttttt tttttttcatg gcactgtact cttctt                             36

<210> SEQ ID NO 69
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 69
tttttttttt tttttttcatg gcactgtact cttcta                             36

<210> SEQ ID NO 70
<211> LENGTH: 36
<212> TYPE: DNA
<213> ORGANISM: artificial
```

```
<220> FEATURE:
<221> NAME/KEY: misc_feature
<222> LOCATION: ()..()
<223> OTHER INFORMATION: Allele-specific Primer

<400> SEQUENCE: 70
tttttttttt tttttcatg gcactgtact cttctc                                36

<210> SEQ ID NO 71
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 71
tttttttttt tttttcatg gcactgtact cttctg                                36

<210> SEQ ID NO 72
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 72
tttttttttt tttttctcat ggcactgtac tcttct                               36

<210> SEQ ID NO 73
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 73
tttttttttt tttttctcat ggcactgtac tcttca                               36

<210> SEQ ID NO 74
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 74
tttttttttt tttttctcat ggcactgtac tcttcc                               36

<210> SEQ ID NO 75
<211> LENGTH: 36
<212> TYPE: DNA
<213> ORGANISM: artificial
<220> FEATURE:
<221> NAME/KEY: misc_feature
<222> LOCATION: ()..()
<223> OTHER INFORMATION: Allele-specific Primer

<400> SEQUENCE: 75
tttttttttt tttttctcat ggcactgtac tcttcg                               36
```

<210> SEQ ID NO 76
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 76
tttttttttt tttttcggag gttgtgaggc gct                    33

<210> SEQ ID NO 77
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 77
tttttttttt tttttcggag gttgtgaggc gca                    33

<210> SEQ ID NO 78
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 78
tttttttttt tttttcggag gttgtgaggc gcc                    33

<210> SEQ ID NO 79
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 79
tttttttttt tttttcggag gttgtgaggc gcg                    33

<210> SEQ ID NO 80
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 80
tttttttttt tttttggagg ttgtgaggcg ctg                    33

<210> SEQ ID NO 81
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

```
<400> SEQUENCE: 81
tttttttttt tttttggagg ttgtgaggcg cta                              33

<210> SEQ ID NO 82
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 82
tttttttttt tttttggagg ttgtgaggcg ctc                              33

<210> SEQ ID NO 83
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 83
tttttttttt tttttggagg ttgtgaggcg ctt                              33

<210> SEQ ID NO 84
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 84
tttttttttt tttttgaggt tgtgaggcgc tgc                              33

<210> SEQ ID NO 85
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 85
tttttttttt tttttgaggt tgtgaggcgc tga                              33

<210> SEQ ID NO 86
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 86
tttttttttt tttttgaggt tgtgaggcgc tgg                              33

<210> SEQ ID NO 87
<211> LENGTH: 33
<212> TYPE: DNA
```

```
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 87
tttttttttt tttttgaggt tgtgaggcgc tgt                                33

<210> SEQ ID NO 88
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 88
tttttttttt tttttaggtt gtgaggcgct gcc                                33

<210> SEQ ID NO 89
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 89
tttttttttt tttttaggtt gtgaggcgct gca                                33

<210> SEQ ID NO 90
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 90
tttttttttt tttttaggtt gtgaggcgct gcg                                33

<210> SEQ ID NO 91
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 91
tttttttttt tttttaggtt gtgaggcgct gct                                33

<210> SEQ ID NO 92
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 92
tttttttttt tttttggttg tgaggcgctg ccc                                33
```

<210> SEQ ID NO 93
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 93 ttttttttttt tttttggttg tgaggcgctg cca                    33

<210> SEQ ID NO 94
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 94 ttttttttttt tttttggttg tgaggcgctg ccg                    33

<210> SEQ ID NO 95
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 95 ttttttttttt tttttggttg tgaggcgctg cct                    33

<210> SEQ ID NO 96
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 96 ttttttttttt tttttgttgt gaggcgctgc ccc                    33

<210> SEQ ID NO 97
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 97 ttttttttttt tttttgttgt gaggcgctgc cca                    33

<210> SEQ ID NO 98
<211> LENGTH: 33
<212> TYPE: DNA
<213> ORGANISM: artificial
<220> FEATURE:
<221> NAME/KEY: misc_feature
<222> LOCATION: ()..()

<223> OTHER INFORMATION: Gene-specific extension primer

<400> SEQUENCE: 98
tttttttttt tttttgttgt gaggcgctgc ccg					33

<210> SEQ ID NO 99
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 99
tttttttttt tttttgttgt gaggcgctgc cct					33

<210> SEQ ID NO 100
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 100
tttttttttt ttttttgtg aggcgctgcc ccc					33

<210> SEQ ID NO 101
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 101
tttttttttt tttttttgtg aggcgctgcc cca					33

<210> SEQ ID NO 102
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 102
tttttttttt tttttttgtg aggcgctgcc ccg					33

<210> SEQ ID NO 103
<211> LENGTH: 33
<212> TYPE: DNA
<213> ORGANISM: artificial
<220> FEATURE:
<221> NAME/KEY: misc_feature
<222> LOCATION: ()..()
<223> OTHER INFORMATION: Gene-specific extension primer

<400> SEQUENCE: 103
tttttttttt tttttttgtg aggcgctgcc cct					33

<210> SEQ ID NO 104
<211> LENGTH: 60

```
<212> TYPE: DNA
<213> ORGANISM: artificial
<220> FEATURE:
<221> NAME/KEY: misc_feature
<222> LOCATION: ()..()
<223> OTHER INFORMATION: Hybridised oligonucleotide

<400> SEQUENCE: 104
accatcgcta tctgagcagc gctcatggtg ggggcagcgc ctcacaacct ccgtcatgtg      60

<210> SEQ ID NO 105
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 105
gcagatcaat taatacgata cctgcggtgt cctgtcctct gagacg                     46

<210> SEQ ID NO 106
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 106
ggttctgttc ttcgttgaca tgagggtgtc ctgtcctctg agaca                      45

<210> SEQ ID NO 107
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 107
ttagtctccg acggcaggct tcaatatggc aaagtccagg gcaca                      45

<210> SEQ ID NO 108
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 108
ctgtgacaga gccaacacgc agtctatggc aaagtccagg gcacg                      45

<210> SEQ ID NO 109
<211> LENGTH: 47
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 109
```

```
cctggtggtt gactgatcac cataactcag aaacttcttg aacccag         47
```

<210> SEQ ID NO 110
<211> LENGTH: 47
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 110

```
gcatgtatag aacataaggt gtctcctcag aaacttcttg aacccaa         47
```

<210> SEQ ID NO 111
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 111

```
gctagatgaa gagcaagcgc atggatgtac gggaggaggc atgg            44
```

<210> SEQ ID NO 112
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 112

```
tacaaccgac agatgtatgt aaggctgtac gggaggaggc atga            44
```

<210> SEQ ID NO 113
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 113

```
ttcaatctgg tctgacctcc ttgtggcccc aggttcccta gtcg            44
```

<210> SEQ ID NO 114
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 114

```
acacgatgtg aatattatct gtggcgcccc aggttcccta gtca            44
```

<210> SEQ ID NO 115
<211> LENGTH: 46
<212> TYPE: DNA
<213> ORGANISM: artificial
<220> FEATURE:
<221> NAME/KEY: misc_feature

```
<222> LOCATION: ()..()
<223> OTHER INFORMATION: Allele-specific primer with tag

<400> SEQUENCE: 115
ttgaagttcg cagaatcgta tgtgtcaaga aagcactgac ctggat              46

<210> SEQ ID NO 116
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 116
aacgtctgtt gagcacatcc tgtaacaaga aagcactgac ctggac              46

<210> SEQ ID NO 117
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 117
ggcaactcat gcaattattg tgagcgcaga ggggacggga aagg                44

<210> SEQ ID NO 118
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 118
ccagaagtat attaatgagc agtgcaggca gaggggacgg gaaaga              46

<210> SEQ ID NO 119
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 119
aagcagtctg tcagtcagtg cgtgaaaagg aagcaccggg gcaaat              46

<210> SEQ ID NO 120
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 120
aatgatgctc tgcgtgatga tgttgaagga agcaccgggg caaac               45

<210> SEQ ID NO 121
```

```
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 121
aatacacgaa ggagttagct gatgcgtgtc caccacaccc ctgg            44

<210> SEQ ID NO 122
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 122
gctgttaatc attaccgtga taacgccgtg tccaccacac ccctga          46

<210> SEQ ID NO 123
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 123
gcggaacggt cagagagatt gatgttggcg gttgtgcgga ttcag           45

<210> SEQ ID NO 124
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 124
gttatggtca gttcgagcat aaggctggcg gttgtgcgga ttcaa           45

<210> SEQ ID NO 125
<211> LENGTH: 48
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 125
ttacctatga ttgatcgtgg tgatatccgg gtggagggac tggaacat        48

<210> SEQ ID NO 126
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 126
```
gctgtggcat tgcagcagat taagggggtgg agggactgga acac  44

<210> SEQ ID NO 127
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 127
tgacgtcatt gtaggcggag agctaggaga cataagtact tctcct  46

<210> SEQ ID NO 128
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 128
tcaataatca acgtaaggcg ttcctggaga cataagtact tctccc  46

<210> SEQ ID NO 129
<211> LENGTH: 49
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 129
ttatcggcta catcggtact gactcaaaga ccaaaacatt tcaagacat  49

<210> SEQ ID NO 130
<211> LENGTH: 49
<212> TYPE: DNA
<213> ORGANISM: artificial
<220> FEATURE:
<221> NAME/KEY: misc_feature
<222> LOCATION: ()..()
<223> OTHER INFORMATION: Allele-specific primer with tag

<400> SEQUENCE: 130
ccattatcgc ctggttcatt cgtgaaaaga ccaaaacatt tcaagacac  49

<210> SEQ ID NO 131
<211> LENGTH: 26
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 131
cgcaggtatc gtattaattg atctgc  26

<210> SEQ ID NO 132
<211> LENGTH: 25
<212> TYPE: DNA
<213> ORGANISM: artificial
<220> FEATURE:

```
<221> NAME/KEY: misc_feature
<222> LOCATION: ()..()
<223> OTHER INFORMATION: Sequence tag

<400> SEQUENCE: 132
cctcatgtca acgaagaaca gaacc                                              25

<210> SEQ ID NO 133
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 133
attgaagcct gccgtcggag actaa                                              25

<210> SEQ ID NO 134
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 134
agactgcgtg ttggctctgt cacag                                              25

<210> SEQ ID NO 135
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 135
ttatggtgat cagtcaacca ccagg                                              25

<210> SEQ ID NO 136
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 136
gagacacctt atgttctata catgc                                              25

<210> SEQ ID NO 137
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 137
tccatgcgct tgctcttcat ctagc                                              25
```

```
<210> SEQ ID NO 138
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 138
gccttacata catctgtcgg ttgta                                    25

<210> SEQ ID NO 139
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 139
cacaaggagg tcagaccaga ttgaa                                    25

<210> SEQ ID NO 140
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 140
gccacagata atattcacat cgtgt                                    25

<210> SEQ ID NO 141
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 141
acacatacga ttctgcgaac ttcaa                                    25

<210> SEQ ID NO 142
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 142
ttacaggatg tgctcaacag acgtt                                    25

<210> SEQ ID NO 143
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag
```

```
<400> SEQUENCE: 143
gctcacaata attgcatgag ttgcc                                    25

<210> SEQ ID NO 144
<211> LENGTH: 27
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 144
ctgcactgct cattaatata cttctgg                                  27

<210> SEQ ID NO 145
<211> LENGTH: 26
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 145
ttcacgcact gactgacaga ctgctt                                   26

<210> SEQ ID NO 146
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 146
caacatcatc acgcagagca tcatt                                    25

<210> SEQ ID NO 147
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 147
gcatcagcta actccttcgt gtatt                                    25

<210> SEQ ID NO 148
<211> LENGTH: 27
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 148
ggcgttatca cggtaatgat taacagc                                  27

<210> SEQ ID NO 149
<211> LENGTH: 25
<212> TYPE: DNA
<213> ORGANISM: artificial
```

```
<220> FEATURE:
<221> NAME/KEY: misc_feature
<222> LOCATION: ()..()
<223> OTHER INFORMATION: Sequence tag

<400> SEQUENCE: 149
acatcaatct ctctgaccgt tccgc                                              25

<210> SEQ ID NO 150
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 150
gccttatgct cgaactgacc ataac                                              25

<210> SEQ ID NO 151
<211> LENGTH: 29
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 151
cggatatcac cacgatcaat cataggtaa                                          29

<210> SEQ ID NO 152
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 152
ccttaatctg ctgcaatgcc acagc                                              25

<210> SEQ ID NO 153
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 153
tagctctccg cctacaatga cgtca                                              25

<210> SEQ ID NO 154
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 154
aggaacgcct tacgttgatt attga                                              25
```

<210> SEQ ID NO 155
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 155
gagtcagtac cgatgtagcc gataa        25

<210> SEQ ID NO 156
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 156
actcgaatga accaggcgat aatgg        25

<210> SEQ ID NO 157
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 157
attatatctg ccgcgaaggt acgcc        25

<210> SEQ ID NO 158
<211> LENGTH: 26
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 158
ggacagacag tggctacggc tcagtt       26

<210> SEQ ID NO 159
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

<400> SEQUENCE: 159
cggtattcgc ttaattcagc acaac        25

<210> SEQ ID NO 160
<211> LENGTH: 25
<212> TYPE: DNA
<213> ORGANISM: artificial
<220> FEATURE:
<221> NAME/KEY: misc_feature
<222> LOCATION: ()..()
<223> OTHER INFORMATION: Sequence tag

```
<400> SEQUENCE: 160
gctcttacct gttgtgcaga tataa                                              25

<210> SEQ ID NO 161
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 161
gcagatcaat taatacgata cctgcgacgc agtaccaaca tgacat                       46

<210> SEQ ID NO 162
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 162
ggttctgttc ttcgttgaca tgaggcgtaa ctacatcttc caca                         44

<210> SEQ ID NO 163
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 163
ttagtctccg acggcaggct tcaattgatt ataaagagta catgc                        45

<210> SEQ ID NO 164
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 164
ctgtgacaga gccaacacgc agtctacgca gtacaaatat gacac                        45

<210> SEQ ID NO 165
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 165
cctggtggtt gactgatcac cataatgtgt ctaaatctgc taca                         44

<210> SEQ ID NO 166
<211> LENGTH: 45
<212> TYPE: DNA
```

```
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 166
gcatgtatag aacataaggt gtctcagatt ataaggaata catgc                45

<210> SEQ ID NO 167
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 167
gctagatgaa gagcaagcgc atggaacgca gtacaaatat gtcat                45

<210> SEQ ID NO 168
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 168
tacaaccgac agatgtatgt aaggccatat ctacttcaga aact                 44

<210> SEQ ID NO 169
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 169
ttcaatctgg tctgacctcc ttgtgtacta actttaaaga gtacc                45

<210> SEQ ID NO 170
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 170
acacgatgtg aatattatct gtggctcgca gtaccaattt aacaa                45

<210> SEQ ID NO 171
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 171
ttgaagttcg cagaatcgta tgtgttacac agtctcctgt acct                 44
```

<210> SEQ ID NO 172
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 172
aacgtctgtt gagcacatcc tgtaatgcta ccaaatttaa gcagt                45

<210> SEQ ID NO 173
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 173
ggcaactcat gcaattattg tgagcacgta gtaccaatat gtctg                45

<210> SEQ ID NO 174
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 174
ccagaagtat attaatgagc agtgcagaat tgcaaacagt gatact               46

<210> SEQ ID NO 175
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 175
aagcagtctg tcagtcagtg cgtgaatagt aattttaaag agtatt               46

<210> SEQ ID NO 176
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 176
aatgatgctc tgcgtgatga tgttgtcgca gtactaatat gactt                45

<210> SEQ ID NO 177
<211> LENGTH: 44
<212> TYPE: DNA
<213> ORGANISM: artificial
<220> FEATURE:
<221> NAME/KEY: misc_feature
<222> LOCATION: ()..()

<223> OTHER INFORMATION: Sequence tag and base-specific primer

<400> SEQUENCE: 177
aatacacgaa ggagttagct gatgcagtaa ctagtgacag taca        44

<210> SEQ ID NO 178
<211> LENGTH: 47
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 178
gctgttaatc attaccgtga taacgccgaa ttttaaagaa tatataa        47

<210> SEQ ID NO 179
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 179
gcggaacggt cagagagatt gatgttcgta gcactaattt aacct        45

<210> SEQ ID NO 180
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 180
gttatggtca gttcgagcat aaggccacac agtcccccac acca        44

<210> SEQ ID NO 181
<211> LENGTH: 49
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 181
ttacctatga ttgatcgtgg tgatatccgt aacagtaatt tcaaggaat        49

<210> SEQ ID NO 182
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 182
gctgtggcat tgcagcagat taaggccgca gtactaattt aacat        45

<210> SEQ ID NO 183
<211> LENGTH: 44

<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 183
tgacgtcatt gtaggcggag agctatacac aaaatcctgt gcca                    44

<210> SEQ ID NO 184
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 184
tcaataatca acgtaaggcg ttccttccta ctaagtttaa gcact                   45

<210> SEQ ID NO 185
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 185
ttatcggcta catcggtact gactctcgca gtactaatgt aacta                   45

<210> SEQ ID NO 186
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 186
ccattatcgc ctggttcatt cgtgacacag cgtcctctgt atca                    44

<210> SEQ ID NO 187
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 187
ggcgtacctt cgcggcagat ataatttcta attttcgtga gtatc                   45

<210> SEQ ID NO 188
<211> LENGTH: 46
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 188
aactgagccg tagccactgt ctgtcctaga agcactaatt tttctg    46

<210> SEQ ID NO 189
<211> LENGTH: 44
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 189
gttgtgctga attaagcgaa taccgtacac aggctagtag ctct    44

<210> SEQ ID NO 190
<211> LENGTH: 45
<212> TYPE: DNA
<213> ORGANISM: artificial
<220> FEATURE:
<221> NAME/KEY: misc_feature
<222> LOCATION: ()..()
<223> OTHER INFORMATION: Sequence tag and base-specific primer

<400> SEQUENCE: 190
ttatatctgc acaacaggta agagctgcca actctaattt taagg    45

<210> SEQ ID NO 191
<211> LENGTH: 20
<212> TYPE: DNA
<213> ORGANISM: Human papillomavirus

<400> SEQUENCE: 191
tagaagcact aatttttctg    20

<210> SEQ ID NO 192
<211> LENGTH: 20
<212> TYPE: DNA
<213> ORGANISM: Human papillomavirus

<400> SEQUENCE: 192
tcgcagtact aatgtaacta    20

<210> SEQ ID NO 193
<211> LENGTH: 20
<212> TYPE: DNA
<213> ORGANISM: Human papillomavirus

<400> SEQUENCE: 193
ccgcagtact aatttaacat    20

<210> SEQ ID NO 194
<211> LENGTH: 20
<212> TYPE: DNA
<213> ORGANISM: Human papillomavirus

<400> SEQUENCE: 194
tcgtagcact aatttaacct    20

<210> SEQ ID NO 195
<211> LENGTH: 20
<212> TYPE: DNA
<213> ORGANISM: Human papillomavirus

<400> SEQUENCE: 195
tcgcagtact aatatgactt    20

```
<210> SEQ ID NO 196
<211> LENGTH: 20
<212> TYPE: DNA
<213> ORGANISM: Human papillomavirus

<400> SEQUENCE: 196
acgtagtacc aatatgtctg                                              20

<210> SEQ ID NO 197
<211> LENGTH: 20
<212> TYPE: DNA
<213> ORGANISM: Human papillomavirus

<400> SEQUENCE: 197
tcgcagtacc aatttaacaa                                              20

<210> SEQ ID NO 198
<211> LENGTH: 20
<212> TYPE: DNA
<213> ORGANISM: Human papillomavirus

<400> SEQUENCE: 198
acgcagtaca aatatgtcat                                              20

<210> SEQ ID NO 199
<211> LENGTH: 20
<212> TYPE: DNA
<213> ORGANISM: Human papillomavirus

<400> SEQUENCE: 199
acgcagtaca aatatgacac                                              20

<210> SEQ ID NO 200
<211> LENGTH: 20
<212> TYPE: DNA
<213> ORGANISM: Human papillomavirus

<400> SEQUENCE: 200
acgcagtacc aacatgacat                                              20

<210> SEQ ID NO 201
<211> LENGTH: 20
<212> TYPE: DNA
<213> ORGANISM: Human papillomavirus

<400> SEQUENCE: 201
acgcagtacc aacatgacat                                              20

<210> SEQ ID NO 202
<211> LENGTH: 20
<212> TYPE: DNA
<213> ORGANISM: Human papillomavirus

<400> SEQUENCE: 202
tagaagcact aatttttctg                                              20

<210> SEQ ID NO 203
<211> LENGTH: 20
<212> TYPE: DNA
<213> ORGANISM: Human papillomavirus

<400> SEQUENCE: 203
```
tcgcagtact aatgtaacta                                              20

<210> SEQ ID NO 204
<211> LENGTH: 20
<212> TYPE: DNA
<213> ORGANISM: Human papillomavirus

<400> SEQUENCE: 204
ccgcagtact aatttaacat                                              20

<210> SEQ ID NO 205
<211> LENGTH: 20
<212> TYPE: DNA
<213> ORGANISM: Human papillomavirus

<400> SEQUENCE: 205
tcgtagcact aatttaacct                                              20

<210> SEQ ID NO 206
<211> LENGTH: 20
<212> TYPE: DNA
<213> ORGANISM: Human papillomavirus

<400> SEQUENCE: 206
tcgcagtact aatatgactt                                              20

<210> SEQ ID NO 207
<211> LENGTH: 20
<212> TYPE: DNA
<213> ORGANISM: Human papillomavirus

<400> SEQUENCE: 207
acgtagtacc aatatgtctg                                              20

<210> SEQ ID NO 208
<211> LENGTH: 20
<212> TYPE: DNA
<213> ORGANISM: Human papillomavirus

<400> SEQUENCE: 208
tcgcagtacc aatttaacaa                                              20

<210> SEQ ID NO 209
<211> LENGTH: 20
<212> TYPE: DNA
<213> ORGANISM: Human papillomavirus

<400> SEQUENCE: 209
acgcagtaca aatatgtcat                                              20

<210> SEQ ID NO 210
<211> LENGTH: 20
<212> TYPE: DNA
<213> ORGANISM: Human papillomavirus

<400> SEQUENCE: 210
acgcagtacc aacatgacat                                              20

<210> SEQ ID NO 211
<211> LENGTH: 20
<212> TYPE: DNA
<213> ORGANISM: Human papillomavirus

<400> SEQUENCE: 211

```
acgcagtaca aatatgacac                                              20

<210> SEQ ID NO 212
<211> LENGTH: 20
<212> TYPE: DNA
<213> ORGANISM: Human papillomavirus

<400> SEQUENCE: 212
acgcagtaca aatatgacac                                              20

<210> SEQ ID NO 213
<211> LENGTH: 20
<212> TYPE: DNA
<213> ORGANISM: Human papillomavirus

<400> SEQUENCE: 213
tagaagcact aatttttctg                                              20

<210> SEQ ID NO 214
<211> LENGTH: 20
<212> TYPE: DNA
<213> ORGANISM: Human papillomavirus

<400> SEQUENCE: 214
tcgcagtact aatgtaacta                                              20

<210> SEQ ID NO 215
<211> LENGTH: 20
<212> TYPE: DNA
<213> ORGANISM: Human papillomavirus

<400> SEQUENCE: 215
ccgcagtact aatttaacat                                              20

<210> SEQ ID NO 216
<211> LENGTH: 20
<212> TYPE: DNA
<213> ORGANISM: Human papillomavirus

<400> SEQUENCE: 216
tcgtagcact aatttaacct                                              20

<210> SEQ ID NO 217
<211> LENGTH: 20
<212> TYPE: DNA
<213> ORGANISM: Human papillomavirus

<400> SEQUENCE: 217
tcgcagtact aatatgactt                                              20

<210> SEQ ID NO 218
<211> LENGTH: 20
<212> TYPE: DNA
<213> ORGANISM: Human papillomavirus

<400> SEQUENCE: 218
acgtagtacc aatatgtctg                                              20

<210> SEQ ID NO 219
<211> LENGTH: 20
<212> TYPE: DNA
<213> ORGANISM: Human papillomavirus
```

```
<400> SEQUENCE: 219
tcgcagtacc aatttaacaa                                          20

<210> SEQ ID NO 220
<211> LENGTH: 20
<212> TYPE: DNA
<213> ORGANISM: Human papillomavirus

<400> SEQUENCE: 220
acgcagtaca aatatgacac                                          20

<210> SEQ ID NO 221
<211> LENGTH: 20
<212> TYPE: DNA
<213> ORGANISM: Human papillomavirus

<400> SEQUENCE: 221
acgcagtacc aacatgacat                                          20

<210> SEQ ID NO 222
<211> LENGTH: 20
<212> TYPE: DNA
<213> ORGANISM: Human papillomavirus

<400> SEQUENCE: 222
acgcagtaca aatatgtcat                                          20

<210> SEQ ID NO 223
<211> LENGTH: 20
<212> TYPE: DNA
<213> ORGANISM: Human papillomavirus

<400> SEQUENCE: 223
acgcagtaca aatatgtcat                                          20

<210> SEQ ID NO 224
<211> LENGTH: 20
<212> TYPE: DNA
<213> ORGANISM: Human papillomavirus

<400> SEQUENCE: 224
tagaagcact aattttctg                                           20

<210> SEQ ID NO 225
<211> LENGTH: 20
<212> TYPE: DNA
<213> ORGANISM: Human papillomavirus

<400> SEQUENCE: 225
tcgcagtact aatgtaacta                                          20

<210> SEQ ID NO 226
<211> LENGTH: 20
<212> TYPE: DNA
<213> ORGANISM: Human papillomavirus

<400> SEQUENCE: 226
ccgcagtact aatttaacat                                          20

<210> SEQ ID NO 227
<211> LENGTH: 20
<212> TYPE: DNA
<213> ORGANISM: Human papillomavirus
```

<400> SEQUENCE: 227
tcgtagcact aatttaacct                              20

<210> SEQ ID NO 228
<211> LENGTH: 20
<212> TYPE: DNA
<213> ORGANISM: Human papillomavirus

<400> SEQUENCE: 228
tcgcagtact aatatgactt                              20

<210> SEQ ID NO 229
<211> LENGTH: 20
<212> TYPE: DNA
<213> ORGANISM: Human papillomavirus

<400> SEQUENCE: 229
acgtagtacc aatatgtctg                              20

<210> SEQ ID NO 230
<211> LENGTH: 20
<212> TYPE: DNA
<213> ORGANISM: Human papillomavirus

<400> SEQUENCE: 230
acgcagtaca aatatgtcat                              20

<210> SEQ ID NO 231
<211> LENGTH: 20
<212> TYPE: DNA
<213> ORGANISM: Human papillomavirus

<400> SEQUENCE: 231
acgcagtaca aatatgacac                              20

<210> SEQ ID NO 232
<211> LENGTH: 20
<212> TYPE: DNA
<213> ORGANISM: Human papillomavirus

<400> SEQUENCE: 232
acgcagtacc aacatgacat                              20

<210> SEQ ID NO 233
<211> LENGTH: 20
<212> TYPE: DNA
<213> ORGANISM: Human papillomavirus

<400> SEQUENCE: 233
tcgcagtacc aatttaacaa                              20

<210> SEQ ID NO 234
<211> LENGTH: 20
<212> TYPE: DNA
<213> ORGANISM: Human papillomavirus

<400> SEQUENCE: 234
tcgcagtacc aatttaacaa                              20

<210> SEQ ID NO 235
<211> LENGTH: 20
<212> TYPE: DNA

<213> ORGANISM: Human papillomavirus

<400> SEQUENCE: 235
tagaagcact aatttttctg					20

<210> SEQ ID NO 236
<211> LENGTH: 20
<212> TYPE: DNA
<213> ORGANISM: Human papillomavirus

<400> SEQUENCE: 236
tcgcagtact aatgtaacta					20

<210> SEQ ID NO 237
<211> LENGTH: 20
<212> TYPE: DNA
<213> ORGANISM: Human papillomavirus

<400> SEQUENCE: 237
ccgcagtact aatttaacat					20

<210> SEQ ID NO 238
<211> LENGTH: 20
<212> TYPE: DNA
<213> ORGANISM: Human papillomavirus

<400> SEQUENCE: 238
tcgtagcact aatttaacct					20

<210> SEQ ID NO 239
<211> LENGTH: 20
<212> TYPE: DNA
<213> ORGANISM: Human papillomavirus

<400> SEQUENCE: 239
tcgcagtact aatatgactt					20

<210> SEQ ID NO 240
<211> LENGTH: 20
<212> TYPE: DNA
<213> ORGANISM: Human papillomavirus

<400> SEQUENCE: 240
tcgcagtacc aatttaacaa					20

<210> SEQ ID NO 241
<211> LENGTH: 20
<212> TYPE: DNA
<213> ORGANISM: Human papillomavirus

<400> SEQUENCE: 241
acgcagtaca aatatgtcat					20

<210> SEQ ID NO 242
<211> LENGTH: 20
<212> TYPE: DNA
<213> ORGANISM: Human papillomavirus

<400> SEQUENCE: 242
acgcagtaca aatatgacac					20

<210> SEQ ID NO 243
<211> LENGTH: 20

```
<212> TYPE: DNA
<213> ORGANISM: Human papillomavirus

<400> SEQUENCE: 243
acgcagtacc aacatgacat                                                20

<210> SEQ ID NO 244
<211> LENGTH: 20
<212> TYPE: DNA
<213> ORGANISM: Human papillomavirus

<400> SEQUENCE: 244
acgtagtacc aatatgtctg                                                20

<210> SEQ ID NO 245
<211> LENGTH: 20
<212> TYPE: DNA
<213> ORGANISM: Human papillomavirus

<400> SEQUENCE: 245
acgtagtacc aatatgtctg                                                20

<210> SEQ ID NO 246
<211> LENGTH: 20
<212> TYPE: DNA
<213> ORGANISM: Human papillomavirus

<400> SEQUENCE: 246
tagaagcact aattttctg                                                 20

<210> SEQ ID NO 247
<211> LENGTH: 20
<212> TYPE: DNA
<213> ORGANISM: Human papillomavirus

<400> SEQUENCE: 247
tcgcagtact aatgtaacta                                                20

<210> SEQ ID NO 248
<211> LENGTH: 20
<212> TYPE: DNA
<213> ORGANISM: Human papillomavirus

<400> SEQUENCE: 248
ccgcagtact aatttaacat                                                20

<210> SEQ ID NO 249
<211> LENGTH: 20
<212> TYPE: DNA
<213> ORGANISM: Human papillomavirus

<400> SEQUENCE: 249
tcgtagcact aatttaacct                                                20

<210> SEQ ID NO 250
<211> LENGTH: 20
<212> TYPE: DNA
<213> ORGANISM: Human papillomavirus

<400> SEQUENCE: 250
acgtagtacc aatatgtctg                                                20

<210> SEQ ID NO 251
```

```
<211> LENGTH: 20
<212> TYPE: DNA
<213> ORGANISM: Human papillomavirus

<400> SEQUENCE: 251
tcgcagtacc aatttaacaa                                                   20

<210> SEQ ID NO 252
<211> LENGTH: 20
<212> TYPE: DNA
<213> ORGANISM: Human papillomavirus

<400> SEQUENCE: 252
acgcagtaca aatatgtcat                                                   20

<210> SEQ ID NO 253
<211> LENGTH: 20
<212> TYPE: DNA
<213> ORGANISM: Human papillomavirus

<400> SEQUENCE: 253
acgcagtaca aatatgacac                                                   20

<210> SEQ ID NO 254
<211> LENGTH: 20
<212> TYPE: DNA
<213> ORGANISM: Human papillomavirus

<400> SEQUENCE: 254
acgcagtacc aacatgacat                                                   20

<210> SEQ ID NO 255
<211> LENGTH: 20
<212> TYPE: DNA
<213> ORGANISM: Human papillomavirus

<400> SEQUENCE: 255
tcgcagtact aatatgactt                                                   20

<210> SEQ ID NO 256
<211> LENGTH: 20
<212> TYPE: DNA
<213> ORGANISM: Human papillomavirus

<400> SEQUENCE: 256
tcgcagtact aatatgactt                                                   20

<210> SEQ ID NO 257
<211> LENGTH: 20
<212> TYPE: DNA
<213> ORGANISM: Human papillomavirus

<400> SEQUENCE: 257
tagaagcact aattttctg                                                    20

<210> SEQ ID NO 258
<211> LENGTH: 20
<212> TYPE: DNA
<213> ORGANISM: Human papillomavirus

<400> SEQUENCE: 258
tcgcagtact aatgtaacta                                                   20
```

```
<210> SEQ ID NO 259
<211> LENGTH: 20
<212> TYPE: DNA
<213> ORGANISM: Human papillomavirus

<400> SEQUENCE: 259
ccgcagtact aatttaacat                                              20

<210> SEQ ID NO 260
<211> LENGTH: 20
<212> TYPE: DNA
<213> ORGANISM: Human papillomavirus

<400> SEQUENCE: 260
tcgcagtact aatatgactt                                              20

<210> SEQ ID NO 261
<211> LENGTH: 20
<212> TYPE: DNA
<213> ORGANISM: Human papillomavirus

<400> SEQUENCE: 261
acgtagtacc aatatgtctg                                              20

<210> SEQ ID NO 262
<211> LENGTH: 20
<212> TYPE: DNA
<213> ORGANISM: Human papillomavirus

<400> SEQUENCE: 262
tcgcagtacc aatttaacaa                                              20

<210> SEQ ID NO 263
<211> LENGTH: 20
<212> TYPE: DNA
<213> ORGANISM: Human papillomavirus

<400> SEQUENCE: 263
acgcagtaca aatatgtcat                                              20

<210> SEQ ID NO 264
<211> LENGTH: 20
<212> TYPE: DNA
<213> ORGANISM: Human papillomavirus

<400> SEQUENCE: 264
acgcagtaca aatatgacac                                              20

<210> SEQ ID NO 265
<211> LENGTH: 20
<212> TYPE: DNA
<213> ORGANISM: Human papillomavirus

<400> SEQUENCE: 265
acgcagtacc aacatgacat                                              20

<210> SEQ ID NO 266
<211> LENGTH: 20
<212> TYPE: DNA
<213> ORGANISM: Human papillomavirus

<400> SEQUENCE: 266
tcgtagcact aatttaacct                                              20
```

```
<210> SEQ ID NO 267
<211> LENGTH: 20
<212> TYPE: DNA
<213> ORGANISM: Human papillomavirus

<400> SEQUENCE: 267
tcgtagcact aatttaacct                                              20

<210> SEQ ID NO 268
<211> LENGTH: 20
<212> TYPE: DNA
<213> ORGANISM: Human papillomavirus

<400> SEQUENCE: 268
tagaagcact aattttctg                                               20

<210> SEQ ID NO 269
<211> LENGTH: 20
<212> TYPE: DNA
<213> ORGANISM: Human papillomavirus

<400> SEQUENCE: 269
tcgcagtact aatgtaacta                                              20

<210> SEQ ID NO 270
<211> LENGTH: 20
<212> TYPE: DNA
<213> ORGANISM: Human papillomavirus

<400> SEQUENCE: 270
tcgtagcact aatttaacct                                              20

<210> SEQ ID NO 271
<211> LENGTH: 20
<212> TYPE: DNA
<213> ORGANISM: Human papillomavirus

<400> SEQUENCE: 271
tcgcagtact aatatgactt                                              20

<210> SEQ ID NO 272
<211> LENGTH: 20
<212> TYPE: DNA
<213> ORGANISM: Human papillomavirus

<400> SEQUENCE: 272
acgtagtacc aatatgtctg                                              20

<210> SEQ ID NO 273
<211> LENGTH: 20
<212> TYPE: DNA
<213> ORGANISM: Human papillomavirus

<400> SEQUENCE: 273
tcgcagtacc aatttaacaa                                              20

<210> SEQ ID NO 274
<211> LENGTH: 20
<212> TYPE: DNA
<213> ORGANISM: Human papillomavirus

<400> SEQUENCE: 274
acgcagtaca aatatgtcat                                              20
```

<210> SEQ ID NO 275
<211> LENGTH: 20
<212> TYPE: DNA
<213> ORGANISM: Human papillomavirus

<400> SEQUENCE: 275
acgcagtaca aatatgacac                                               20

<210> SEQ ID NO 276
<211> LENGTH: 20
<212> TYPE: DNA
<213> ORGANISM: Human papillomavirus

<400> SEQUENCE: 276
acgcagtacc aacatgacat                                               20

<210> SEQ ID NO 277
<211> LENGTH: 20
<212> TYPE: DNA
<213> ORGANISM: Human papillomavirus

<400> SEQUENCE: 277
ccgcagtact aatttaacat                                               20

<210> SEQ ID NO 278
<211> LENGTH: 20
<212> TYPE: DNA
<213> ORGANISM: Human papillomavirus

<400> SEQUENCE: 278
ccgcagtact aatttaacat                                               20

<210> SEQ ID NO 279
<211> LENGTH: 20
<212> TYPE: DNA
<213> ORGANISM: Human papillomavirus

<400> SEQUENCE: 279
tagaagcact aattttctg                                                20

<210> SEQ ID NO 280
<211> LENGTH: 20
<212> TYPE: DNA
<213> ORGANISM: Human papillomavirus

<400> SEQUENCE: 280
ccgcagtact aatttaacat                                               20

<210> SEQ ID NO 281
<211> LENGTH: 20
<212> TYPE: DNA
<213> ORGANISM: Human papillomavirus

<400> SEQUENCE: 281
tcgtagcact aatttaacct                                               20

<210> SEQ ID NO 282
<211> LENGTH: 20
<212> TYPE: DNA
<213> ORGANISM: Human papillomavirus

<400> SEQUENCE: 282

```
tcgcagtact aatatgactt                                         20

<210> SEQ ID NO 283
<211> LENGTH: 20
<212> TYPE: DNA
<213> ORGANISM: Human papillomavirus

<400> SEQUENCE: 283
acgtagtacc aatatgtctg                                         20

<210> SEQ ID NO 284
<211> LENGTH: 20
<212> TYPE: DNA
<213> ORGANISM: Human papillomavirus

<400> SEQUENCE: 284
tcgcagtacc aatttaacaa                                         20

<210> SEQ ID NO 285
<211> LENGTH: 20
<212> TYPE: DNA
<213> ORGANISM: Human papillomavirus

<400> SEQUENCE: 285
acgcagtaca aatatgtcat                                         20

<210> SEQ ID NO 286
<211> LENGTH: 20
<212> TYPE: DNA
<213> ORGANISM: Human papillomavirus

<400> SEQUENCE: 286
acgcagtaca aatatgacac                                         20

<210> SEQ ID NO 287
<211> LENGTH: 20
<212> TYPE: DNA
<213> ORGANISM: Human papillomavirus

<400> SEQUENCE: 287
acgcagtacc aacatgacat                                         20

<210> SEQ ID NO 288
<211> LENGTH: 20
<212> TYPE: DNA
<213> ORGANISM: Human papillomavirus

<400> SEQUENCE: 288
tcgcagtact aatgtaacta                                         20

<210> SEQ ID NO 289
<211> LENGTH: 20
<212> TYPE: DNA
<213> ORGANISM: Human papillomavirus

<400> SEQUENCE: 289
tcgcagtact aatgtaacta                                         20

<210> SEQ ID NO 290
<211> LENGTH: 20
<212> TYPE: DNA
<213> ORGANISM: Human papillomavirus

<400> SEQUENCE: 290
```
tcgcagtact aatgtaacta                                          20

<210> SEQ ID NO 291
<211> LENGTH: 20
<212> TYPE: DNA
<213> ORGANISM: Human papillomavirus

<400> SEQUENCE: 291
ccgcagtact aatttaacat                                          20

<210> SEQ ID NO 292
<211> LENGTH: 20
<212> TYPE: DNA
<213> ORGANISM: Human papillomavirus

<400> SEQUENCE: 292
tcgtagcact aatttaacct                                          20

<210> SEQ ID NO 293
<211> LENGTH: 20
<212> TYPE: DNA
<213> ORGANISM: Human papillomavirus

<400> SEQUENCE: 293
tcgcagtact aatatgactt                                          20

<210> SEQ ID NO 294
<211> LENGTH: 20
<212> TYPE: DNA
<213> ORGANISM: Human papillomavirus

<400> SEQUENCE: 294
acgtagtacc aatatgtctg                                          20

<210> SEQ ID NO 295
<211> LENGTH: 20
<212> TYPE: DNA
<213> ORGANISM: Human papillomavirus

<400> SEQUENCE: 295
tcgcagtacc aatttaacaa                                          20

<210> SEQ ID NO 296
<211> LENGTH: 20
<212> TYPE: DNA
<213> ORGANISM: Human papillomavirus

<400> SEQUENCE: 296
acgcagtaca aatatgtcat                                          20

<210> SEQ ID NO 297
<211> LENGTH: 20
<212> TYPE: DNA
<213> ORGANISM: Human papillomavirus

<400> SEQUENCE: 297
acgcagtaca aatatgacac                                          20

<210> SEQ ID NO 298
<211> LENGTH: 20
<212> TYPE: DNA
<213> ORGANISM: Human papillomavirus

```
<400> SEQUENCE: 298
acgcagtacc aacatgacat                                               20

<210> SEQ ID NO 299
<211> LENGTH: 20
<212> TYPE: DNA
<213> ORGANISM: Human papillomavirus

<400> SEQUENCE: 299
tagaagcact aatttttctg                                               20

<210> SEQ ID NO 300
<211> LENGTH: 20
<212> TYPE: DNA
<213> ORGANISM: Human papillomavirus

<400> SEQUENCE: 300
tagaagcact aatttttctg                                               20

<210> SEQ ID NO 301
<211> LENGTH: 19
<212> TYPE: DNA
<213> ORGANISM: Human papillomavirus

<400> SEQUENCE: 301
tacacaggct agtagctct                                                19

<210> SEQ ID NO 302
<211> LENGTH: 19
<212> TYPE: DNA
<213> ORGANISM: Human papillomavirus

<400> SEQUENCE: 302
cacagcgtcc tctgtatca                                                19

<210> SEQ ID NO 303
<211> LENGTH: 19
<212> TYPE: DNA
<213> ORGANISM: Human papillomavirus

<400> SEQUENCE: 303
tacacaaaat cctgtgcca                                                19

<210> SEQ ID NO 304
<211> LENGTH: 19
<212> TYPE: DNA
<213> ORGANISM: Human papillomavirus

<400> SEQUENCE: 304
cacacagtcc cccacacca                                                19

<210> SEQ ID NO 305
<211> LENGTH: 19
<212> TYPE: DNA
<213> ORGANISM: Human papillomavirus

<400> SEQUENCE: 305
agtaactagt gacagtaca                                                19

<210> SEQ ID NO 306
<211> LENGTH: 19
<212> TYPE: DNA
<213> ORGANISM: Human papillomavirus
```

```
<400> SEQUENCE: 306
aattgcaaac agtgatact                                        19

<210> SEQ ID NO 307
<211> LENGTH: 19
<212> TYPE: DNA
<213> ORGANISM: Human papillomavirus

<400> SEQUENCE: 307
tacacagtct cctgtacct                                        19

<210> SEQ ID NO 308
<211> LENGTH: 19
<212> TYPE: DNA
<213> ORGANISM: Human papillomavirus

<400> SEQUENCE: 308
catatctact tcagaaact                                        19

<210> SEQ ID NO 309
<211> LENGTH: 19
<212> TYPE: DNA
<213> ORGANISM: Human papillomavirus

<400> SEQUENCE: 309
tgtgtctaaa tctgctaca                                        19

<210> SEQ ID NO 310
<211> LENGTH: 19
<212> TYPE: DNA
<213> ORGANISM: Human papillomavirus

<400> SEQUENCE: 310
cgtaactaca tcttccaca                                        19

<210> SEQ ID NO 311
<211> LENGTH: 19
<212> TYPE: DNA
<213> ORGANISM: Human papillomavirus

<400> SEQUENCE: 311
cgtaactaca tcttccaca                                        19

<210> SEQ ID NO 312
<211> LENGTH: 19
<212> TYPE: DNA
<213> ORGANISM: Human papillomavirus

<400> SEQUENCE: 312
tacacaggct agtagctct                                        19

<210> SEQ ID NO 313
<211> LENGTH: 19
<212> TYPE: DNA
<213> ORGANISM: Human papillomavirus

<400> SEQUENCE: 313
cacagcgtcc tctgtatca                                        19

<210> SEQ ID NO 314
<211> LENGTH: 19
<212> TYPE: DNA
```

<213> ORGANISM: Human papillomavirus

<400> SEQUENCE: 314
tacacaaaat cctgtgcca                                               19

<210> SEQ ID NO 315
<211> LENGTH: 19
<212> TYPE: DNA
<213> ORGANISM: Human papillomavirus

<400> SEQUENCE: 315
cacacagtcc cccacacca                                               19

<210> SEQ ID NO 316
<211> LENGTH: 19
<212> TYPE: DNA
<213> ORGANISM: Human papillomavirus

<400> SEQUENCE: 316
agtaactagt gacagtaca                                               19

<210> SEQ ID NO 317
<211> LENGTH: 19
<212> TYPE: DNA
<213> ORGANISM: Human papillomavirus

<400> SEQUENCE: 317
aattgcaaac agtgatact                                               19

<210> SEQ ID NO 318
<211> LENGTH: 19
<212> TYPE: DNA
<213> ORGANISM: Human papillomavirus

<400> SEQUENCE: 318
tacacagtct cctgtacct                                               19

<210> SEQ ID NO 319
<211> LENGTH: 19
<212> TYPE: DNA
<213> ORGANISM: Human papillomavirus

<400> SEQUENCE: 319
catatctact tcagaaact                                               19

<210> SEQ ID NO 320
<211> LENGTH: 19
<212> TYPE: DNA
<213> ORGANISM: Human papillomavirus

<400> SEQUENCE: 320
cgtaactaca tcttccaca                                               19

<210> SEQ ID NO 321
<211> LENGTH: 19
<212> TYPE: DNA
<213> ORGANISM: Human papillomavirus

<400> SEQUENCE: 321
tgtgtctaaa tctgctaca                                               19

<210> SEQ ID NO 322
<211> LENGTH: 19

```
<212> TYPE: DNA
<213> ORGANISM: Human papillomavirus

<400> SEQUENCE: 322
tgtgtctaaa tctgctaca                                                  19

<210> SEQ ID NO 323
<211> LENGTH: 19
<212> TYPE: DNA
<213> ORGANISM: Human papillomavirus

<400> SEQUENCE: 323
tacacaggct agtagctct                                                  19

<210> SEQ ID NO 324
<211> LENGTH: 19
<212> TYPE: DNA
<213> ORGANISM: Human papillomavirus

<400> SEQUENCE: 324
cacagcgtcc tctgtatca                                                  19

<210> SEQ ID NO 325
<211> LENGTH: 19
<212> TYPE: DNA
<213> ORGANISM: Human papillomavirus

<400> SEQUENCE: 325
tacacaaaat cctgtgcca                                                  19

<210> SEQ ID NO 326
<211> LENGTH: 19
<212> TYPE: DNA
<213> ORGANISM: Human papillomavirus

<400> SEQUENCE: 326
cacacagtcc cccacacca                                                  19

<210> SEQ ID NO 327
<211> LENGTH: 19
<212> TYPE: DNA
<213> ORGANISM: Human papillomavirus

<400> SEQUENCE: 327
agtaactagt gacagtaca                                                  19

<210> SEQ ID NO 328
<211> LENGTH: 19
<212> TYPE: DNA
<213> ORGANISM: Human papillomavirus

<400> SEQUENCE: 328
aattgcaaac agtgatact                                                  19

<210> SEQ ID NO 329
<211> LENGTH: 19
<212> TYPE: DNA
<213> ORGANISM: Human papillomavirus

<400> SEQUENCE: 329
tacacagtct cctgtacct                                                  19

<210> SEQ ID NO 330
```

```
<211> LENGTH: 19
<212> TYPE: DNA
<213> ORGANISM: Human papillomavirus

<400> SEQUENCE: 330
tgtgtctaaa tctgctaca                                              19

<210> SEQ ID NO 331
<211> LENGTH: 19
<212> TYPE: DNA
<213> ORGANISM: Human papillomavirus

<400> SEQUENCE: 331
cgtaactaca tcttccaca                                              19

<210> SEQ ID NO 332
<211> LENGTH: 19
<212> TYPE: DNA
<213> ORGANISM: Human papillomavirus

<400> SEQUENCE: 332
catatctact tcagaaact                                              19

<210> SEQ ID NO 333
<211> LENGTH: 19
<212> TYPE: DNA
<213> ORGANISM: Human papillomavirus

<400> SEQUENCE: 333
catatctact tcagaaact                                              19

<210> SEQ ID NO 334
<211> LENGTH: 19
<212> TYPE: DNA
<213> ORGANISM: Human papillomavirus

<400> SEQUENCE: 334
tacacaggct agtagctct                                              19

<210> SEQ ID NO 335
<211> LENGTH: 19
<212> TYPE: DNA
<213> ORGANISM: Human papillomavirus

<400> SEQUENCE: 335
cacagcgtcc tctgtatca                                              19

<210> SEQ ID NO 336
<211> LENGTH: 19
<212> TYPE: DNA
<213> ORGANISM: Human papillomavirus

<400> SEQUENCE: 336
tacacaaaat cctgtgcca                                              19

<210> SEQ ID NO 337
<211> LENGTH: 19
<212> TYPE: DNA
<213> ORGANISM: Human papillomavirus

<400> SEQUENCE: 337
cacacagtcc cccacacca                                              19
```

```
<210> SEQ ID NO 338
<211> LENGTH: 19
<212> TYPE: DNA
<213> ORGANISM: Human papillomavirus

<400> SEQUENCE: 338
agtaactagt gacagtaca                                                19

<210> SEQ ID NO 339
<211> LENGTH: 19
<212> TYPE: DNA
<213> ORGANISM: Human papillomavirus

<400> SEQUENCE: 339
aattgcaaac agtgatact                                                19

<210> SEQ ID NO 340
<211> LENGTH: 19
<212> TYPE: DNA
<213> ORGANISM: Human papillomavirus

<400> SEQUENCE: 340
catatctact tcagaaact                                                19

<210> SEQ ID NO 341
<211> LENGTH: 19
<212> TYPE: DNA
<213> ORGANISM: Human papillomavirus

<400> SEQUENCE: 341
tgtgtctaaa tctgctaca                                                19

<210> SEQ ID NO 342
<211> LENGTH: 19
<212> TYPE: DNA
<213> ORGANISM: Human papillomavirus

<400> SEQUENCE: 342
cgtaactaca tcttccaca                                                19

<210> SEQ ID NO 343
<211> LENGTH: 19
<212> TYPE: DNA
<213> ORGANISM: Human papillomavirus

<400> SEQUENCE: 343
tacacagtct cctgtacct                                                19

<210> SEQ ID NO 344
<211> LENGTH: 19
<212> TYPE: DNA
<213> ORGANISM: Human papillomavirus

<400> SEQUENCE: 344
tacacagtct cctgtacct                                                19

<210> SEQ ID NO 345
<211> LENGTH: 19
<212> TYPE: DNA
<213> ORGANISM: Human papillomavirus

<400> SEQUENCE: 345
tacacaggct agtagctct                                                19
```

-continued

```
<210> SEQ ID NO 346
<211> LENGTH: 19
<212> TYPE: DNA
<213> ORGANISM: Human papillomavirus

<400> SEQUENCE: 346
cacagcgtcc tctgtatca                                                  19

<210> SEQ ID NO 347
<211> LENGTH: 19
<212> TYPE: DNA
<213> ORGANISM: Human papillomavirus

<400> SEQUENCE: 347
tacacaaaat cctgtgcca                                                  19

<210> SEQ ID NO 348
<211> LENGTH: 19
<212> TYPE: DNA
<213> ORGANISM: Human papillomavirus

<400> SEQUENCE: 348
cacacagtcc cccacacca                                                  19

<210> SEQ ID NO 349
<211> LENGTH: 19
<212> TYPE: DNA
<213> ORGANISM: Human papillomavirus

<400> SEQUENCE: 349
agtaactagt gacagtaca                                                  19

<210> SEQ ID NO 350
<211> LENGTH: 19
<212> TYPE: DNA
<213> ORGANISM: Human papillomavirus

<400> SEQUENCE: 350
tacacagtct cctgtacct                                                  19

<210> SEQ ID NO 351
<211> LENGTH: 19
<212> TYPE: DNA
<213> ORGANISM: Human papillomavirus

<400> SEQUENCE: 351
catatctact tcagaaact                                                  19

<210> SEQ ID NO 352
<211> LENGTH: 19
<212> TYPE: DNA
<213> ORGANISM: Human papillomavirus

<400> SEQUENCE: 352
tgtgtctaaa tctgctaca                                                  19

<210> SEQ ID NO 353
<211> LENGTH: 19
<212> TYPE: DNA
<213> ORGANISM: Human papillomavirus

<400> SEQUENCE: 353
cgtaactaca tcttccaca                                                  19
```

<210> SEQ ID NO 354
<211> LENGTH: 19
<212> TYPE: DNA
<213> ORGANISM: Human papillomavirus

<400> SEQUENCE: 354
aattgcaaac agtgatact                                               19

<210> SEQ ID NO 355
<211> LENGTH: 19
<212> TYPE: DNA
<213> ORGANISM: Human papillomavirus

<400> SEQUENCE: 355
aattgcaaac agtgatact                                               19

<210> SEQ ID NO 356
<211> LENGTH: 19
<212> TYPE: DNA
<213> ORGANISM: Human papillomavirus

<400> SEQUENCE: 356
tacacaggct agtagctct                                               19

<210> SEQ ID NO 357
<211> LENGTH: 19
<212> TYPE: DNA
<213> ORGANISM: Human papillomavirus

<400> SEQUENCE: 357
cacagcgtcc tctgtatca                                               19

<210> SEQ ID NO 358
<211> LENGTH: 19
<212> TYPE: DNA
<213> ORGANISM: Human papillomavirus

<400> SEQUENCE: 358
tacacaaaat cctgtgcca                                               19

<210> SEQ ID NO 359
<211> LENGTH: 19
<212> TYPE: DNA
<213> ORGANISM: Human papillomavirus

<400> SEQUENCE: 359
cacacagtcc cccacacca                                               19

<210> SEQ ID NO 360
<211> LENGTH: 19
<212> TYPE: DNA
<213> ORGANISM: Human papillomavirus

<400> SEQUENCE: 360
aattgcaaac agtgatact                                               19

<210> SEQ ID NO 361
<211> LENGTH: 19
<212> TYPE: DNA
<213> ORGANISM: Human papillomavirus

<400> SEQUENCE: 361

-continued tacacagtct cctgtacct    19

<210> SEQ ID NO 362
<211> LENGTH: 19
<212> TYPE: DNA
<213> ORGANISM: Human papillomavirus

<400> SEQUENCE: 362
catatctact tcagaaact    19

<210> SEQ ID NO 363
<211> LENGTH: 19
<212> TYPE: DNA
<213> ORGANISM: Human papillomavirus

<400> SEQUENCE: 363
tgtgtctaaa tctgctaca    19

<210> SEQ ID NO 364
<211> LENGTH: 19
<212> TYPE: DNA
<213> ORGANISM: Human papillomavirus

<400> SEQUENCE: 364
cgtaactaca tcttccaca    19

<210> SEQ ID NO 365
<211> LENGTH: 19
<212> TYPE: DNA
<213> ORGANISM: Human papillomavirus

<400> SEQUENCE: 365
agtaactagt gacagtaca    19

<210> SEQ ID NO 366
<211> LENGTH: 19
<212> TYPE: DNA
<213> ORGANISM: Human papillomavirus

<400> SEQUENCE: 366
agtaactagt gacagtaca    19

<210> SEQ ID NO 367
<211> LENGTH: 19
<212> TYPE: DNA
<213> ORGANISM: Human papillomavirus

<400> SEQUENCE: 367
tacacaggct agtagctct    19

<210> SEQ ID NO 368
<211> LENGTH: 19
<212> TYPE: DNA
<213> ORGANISM: Human papillomavirus

<400> SEQUENCE: 368
cacagcgtcc tctgtatca    19

<210> SEQ ID NO 369
<211> LENGTH: 19
<212> TYPE: DNA
<213> ORGANISM: Human papillomavirus

<400> SEQUENCE: 369

-continued tacacaaaat cctgtgcca				19

<210> SEQ ID NO 370
<211> LENGTH: 19
<212> TYPE: DNA
<213> ORGANISM: Human papillomavirus

<400> SEQUENCE: 370
agtaactagt gacagtaca				19

<210> SEQ ID NO 371
<211> LENGTH: 19
<212> TYPE: DNA
<213> ORGANISM: Human papillomavirus

<400> SEQUENCE: 371
aattgcaaac agtgatact				19

<210> SEQ ID NO 372
<211> LENGTH: 19
<212> TYPE: DNA
<213> ORGANISM: Human papillomavirus

<400> SEQUENCE: 372
tacacagtct cctgtacct				19

<210> SEQ ID NO 373
<211> LENGTH: 19
<212> TYPE: DNA
<213> ORGANISM: Human papillomavirus

<400> SEQUENCE: 373
catatctact tcagaaact				19

<210> SEQ ID NO 374
<211> LENGTH: 19
<212> TYPE: DNA
<213> ORGANISM: Human papillomavirus

<400> SEQUENCE: 374
tgtgtctaaa tctgctaca				19

<210> SEQ ID NO 375
<211> LENGTH: 19
<212> TYPE: DNA
<213> ORGANISM: Human papillomavirus

<400> SEQUENCE: 375
cgtaactaca tcttccaca				19

<210> SEQ ID NO 376
<211> LENGTH: 19
<212> TYPE: DNA
<213> ORGANISM: Human papillomavirus

<400> SEQUENCE: 376
cacacagtcc cccacacca				19

<210> SEQ ID NO 377
<211> LENGTH: 19
<212> TYPE: DNA
<213> ORGANISM: Human papillomavirus

```
<400> SEQUENCE: 377
cacacagtcc cccacacca                                             19

<210> SEQ ID NO 378
<211> LENGTH: 19
<212> TYPE: DNA
<213> ORGANISM: Human papillomavirus

<400> SEQUENCE: 378
tacacaggct agtagctct                                             19

<210> SEQ ID NO 379
<211> LENGTH: 19
<212> TYPE: DNA
<213> ORGANISM: Human papillomavirus

<400> SEQUENCE: 379
cacagcgtcc tctgtatca                                             19

<210> SEQ ID NO 380
<211> LENGTH: 19
<212> TYPE: DNA
<213> ORGANISM: Human papillomavirus

<400> SEQUENCE: 380
cacacagtcc cccacacca                                             19

<210> SEQ ID NO 381
<211> LENGTH: 19
<212> TYPE: DNA
<213> ORGANISM: Human papillomavirus

<400> SEQUENCE: 381
agtaactagt gacagtaca                                             19

<210> SEQ ID NO 382
<211> LENGTH: 19
<212> TYPE: DNA
<213> ORGANISM: Human papillomavirus

<400> SEQUENCE: 382
aattgcaaac agtgatact                                             19

<210> SEQ ID NO 383
<211> LENGTH: 19
<212> TYPE: DNA
<213> ORGANISM: Human papillomavirus

<400> SEQUENCE: 383
tacacagtct cctgtacct                                             19

<210> SEQ ID NO 384
<211> LENGTH: 19
<212> TYPE: DNA
<213> ORGANISM: Human papillomavirus

<400> SEQUENCE: 384
catatctact tcagaaact                                             19

<210> SEQ ID NO 385
<211> LENGTH: 19
<212> TYPE: DNA
<213> ORGANISM: Human papillomavirus
```

-continued

```
<400> SEQUENCE: 385
tgtgtctaaa tctgctaca                                                    19

<210> SEQ ID NO 386
<211> LENGTH: 19
<212> TYPE: DNA
<213> ORGANISM: Human papillomavirus

<400> SEQUENCE: 386
cgtaactaca tcttccaca                                                    19

<210> SEQ ID NO 387
<211> LENGTH: 19
<212> TYPE: DNA
<213> ORGANISM: Human papillomavirus

<400> SEQUENCE: 387
tacacaaaat cctgtgcca                                                    19

<210> SEQ ID NO 388
<211> LENGTH: 19
<212> TYPE: DNA
<213> ORGANISM: Human papillomavirus

<400> SEQUENCE: 388
tacacaaaat cctgtgcca                                                    19

<210> SEQ ID NO 389
<211> LENGTH: 19
<212> TYPE: DNA
<213> ORGANISM: Human papillomavirus

<400> SEQUENCE: 389
tacacaggct agtagctct                                                    19

<210> SEQ ID NO 390
<211> LENGTH: 19
<212> TYPE: DNA
<213> ORGANISM: Human papillomavirus

<400> SEQUENCE: 390
tacacaaaat cctgtgcca                                                    19

<210> SEQ ID NO 391
<211> LENGTH: 19
<212> TYPE: DNA
<213> ORGANISM: Human papillomavirus

<400> SEQUENCE: 391
cacacagtcc cccacacca                                                    19

<210> SEQ ID NO 392
<211> LENGTH: 19
<212> TYPE: DNA
<213> ORGANISM: Human papillomavirus

<400> SEQUENCE: 392
agtaactagt gacagtaca                                                    19

<210> SEQ ID NO 393
<211> LENGTH: 19
<212> TYPE: DNA
```

```
<213> ORGANISM: Human papillomavirus

<400> SEQUENCE: 393
aattgcaaac agtgatact                                              19

<210> SEQ ID NO 394
<211> LENGTH: 19
<212> TYPE: DNA
<213> ORGANISM: Human papillomavirus

<400> SEQUENCE: 394
tacacagtct cctgtacct                                              19

<210> SEQ ID NO 395
<211> LENGTH: 19
<212> TYPE: DNA
<213> ORGANISM: Human papillomavirus

<400> SEQUENCE: 395
catatctact tcagaaact                                              19

<210> SEQ ID NO 396
<211> LENGTH: 19
<212> TYPE: DNA
<213> ORGANISM: Human papillomavirus

<400> SEQUENCE: 396
tgtgtctaaa tctgctaca                                              19

<210> SEQ ID NO 397
<211> LENGTH: 19
<212> TYPE: DNA
<213> ORGANISM: Human papillomavirus

<400> SEQUENCE: 397
cgtaactaca tcttccaca                                              19

<210> SEQ ID NO 398
<211> LENGTH: 19
<212> TYPE: DNA
<213> ORGANISM: Human papillomavirus

<400> SEQUENCE: 398
cacagcgtcc tctgtatca                                              19

<210> SEQ ID NO 399
<211> LENGTH: 19
<212> TYPE: DNA
<213> ORGANISM: Human papillomavirus

<400> SEQUENCE: 399
cacagcgtcc tctgtatca                                              19

<210> SEQ ID NO 400
<211> LENGTH: 19
<212> TYPE: DNA
<213> ORGANISM: Human papillomavirus

<400> SEQUENCE: 400
cacagcgtcc tctgtatca                                              19

<210> SEQ ID NO 401
<211> LENGTH: 19
```

-continued

```
<212> TYPE: DNA
<213> ORGANISM: Human papillomavirus

<400> SEQUENCE: 401
tacacaaaat cctgtgcca                                                 19

<210> SEQ ID NO 402
<211> LENGTH: 19
<212> TYPE: DNA
<213> ORGANISM: Human papillomavirus

<400> SEQUENCE: 402
cacacagtcc cccacacca                                                 19

<210> SEQ ID NO 403
<211> LENGTH: 19
<212> TYPE: DNA
<213> ORGANISM: Human papillomavirus

<400> SEQUENCE: 403
agtaactagt gacagtaca                                                 19

<210> SEQ ID NO 404
<211> LENGTH: 19
<212> TYPE: DNA
<213> ORGANISM: Human papillomavirus

<400> SEQUENCE: 404
aattgcaaac agtgatact                                                 19

<210> SEQ ID NO 405
<211> LENGTH: 19
<212> TYPE: DNA
<213> ORGANISM: Human papillomavirus

<400> SEQUENCE: 405
tacacagtct cctgtacct                                                 19

<210> SEQ ID NO 406
<211> LENGTH: 19
<212> TYPE: DNA
<213> ORGANISM: Human papillomavirus

<400> SEQUENCE: 406
catatctact tcagaaact                                                 19

<210> SEQ ID NO 407
<211> LENGTH: 19
<212> TYPE: DNA
<213> ORGANISM: Human papillomavirus

<400> SEQUENCE: 407
tgtgtctaaa tctgctaca                                                 19

<210> SEQ ID NO 408
<211> LENGTH: 19
<212> TYPE: DNA
<213> ORGANISM: Human papillomavirus

<400> SEQUENCE: 408
cgtaactaca tcttccaca                                                 19

<210> SEQ ID NO 409
```

```
<211> LENGTH: 19
<212> TYPE: DNA
<213> ORGANISM: Human papillomavirus

<400> SEQUENCE: 409
tacacaggct agtagctct                                                  19

<210> SEQ ID NO 410
<211> LENGTH: 19
<212> TYPE: DNA
<213> ORGANISM: Human papillomavirus

<400> SEQUENCE: 410
tacacaggct agtagctct                                                  19

<210> SEQ ID NO 411
<211> LENGTH: 20
<212> TYPE: DNA
<213> ORGANISM: Human papillomavirus

<400> SEQUENCE: 411
tgccaactct aattttaagg                                                 20

<210> SEQ ID NO 412
<211> LENGTH: 20
<212> TYPE: DNA
<213> ORGANISM: Human papillomavirus

<400> SEQUENCE: 412
ttctaatttt cgtgagtatc                                                 20

<210> SEQ ID NO 413
<211> LENGTH: 20
<212> TYPE: DNA
<213> ORGANISM: Human papillomavirus

<400> SEQUENCE: 413
tcctactaag tttaagcact                                                 20

<210> SEQ ID NO 414
<211> LENGTH: 20
<212> TYPE: DNA
<213> ORGANISM: Human papillomavirus

<400> SEQUENCE: 414
taacagtaat ttcaaggaat                                                 20

<210> SEQ ID NO 415
<211> LENGTH: 20
<212> TYPE: DNA
<213> ORGANISM: Human papillomavirus

<400> SEQUENCE: 415
gaattttaaa gaatatataa                                                 20

<210> SEQ ID NO 416
<211> LENGTH: 20
<212> TYPE: DNA
<213> ORGANISM: Human papillomavirus

<400> SEQUENCE: 416
tagtaatttt aaagagtatt                                                 20
```

<210> SEQ ID NO 417
<211> LENGTH: 20
<212> TYPE: DNA
<213> ORGANISM: Human papillomavirus

<400> SEQUENCE: 417
tgctaccaaa tttaagcagt					20

<210> SEQ ID NO 418
<211> LENGTH: 20
<212> TYPE: DNA
<213> ORGANISM: Human papillomavirus

<400> SEQUENCE: 418
tactaacttt aaagagtacc					20

<210> SEQ ID NO 419
<211> LENGTH: 20
<212> TYPE: DNA
<213> ORGANISM: Human papillomavirus

<400> SEQUENCE: 419
agattataag gaatacatgc					20

<210> SEQ ID NO 420
<211> LENGTH: 20
<212> TYPE: DNA
<213> ORGANISM: Human papillomavirus

<400> SEQUENCE: 420
tgattataaa gagtacatgc					20

<210> SEQ ID NO 421
<211> LENGTH: 20
<212> TYPE: DNA
<213> ORGANISM: Human papillomavirus

<400> SEQUENCE: 421
tgattataaa gagtacatgc					20

<210> SEQ ID NO 422
<211> LENGTH: 20
<212> TYPE: DNA
<213> ORGANISM: Human papillomavirus

<400> SEQUENCE: 422
tgccaactct aattttaagg					20

<210> SEQ ID NO 423
<211> LENGTH: 20
<212> TYPE: DNA
<213> ORGANISM: Human papillomavirus

<400> SEQUENCE: 423
ttctaatttt cgtgagtatc					20

<210> SEQ ID NO 424
<211> LENGTH: 20
<212> TYPE: DNA
<213> ORGANISM: Human papillomavirus

<400> SEQUENCE: 424
tcctactaag tttaagcact					20

```
<210> SEQ ID NO 425
<211> LENGTH: 20
<212> TYPE: DNA
<213> ORGANISM: Human papillomavirus

<400> SEQUENCE: 425
taacagtaat ttcaaggaat                                              20

<210> SEQ ID NO 426
<211> LENGTH: 20
<212> TYPE: DNA
<213> ORGANISM: Human papillomavirus

<400> SEQUENCE: 426
gaattttaaa gaatatataa                                              20

<210> SEQ ID NO 427
<211> LENGTH: 20
<212> TYPE: DNA
<213> ORGANISM: Human papillomavirus

<400> SEQUENCE: 427
tagtaatttt aaagagtatt                                              20

<210> SEQ ID NO 428
<211> LENGTH: 20
<212> TYPE: DNA
<213> ORGANISM: Human papillomavirus

<400> SEQUENCE: 428
tgctaccaaa tttaagcagt                                              20

<210> SEQ ID NO 429
<211> LENGTH: 20
<212> TYPE: DNA
<213> ORGANISM: Human papillomavirus

<400> SEQUENCE: 429
tactaacttt aaagagtacc                                              20

<210> SEQ ID NO 430
<211> LENGTH: 20
<212> TYPE: DNA
<213> ORGANISM: Human papillomavirus

<400> SEQUENCE: 430
tgattataaa gagtacatgc                                              20

<210> SEQ ID NO 431
<211> LENGTH: 20
<212> TYPE: DNA
<213> ORGANISM: Human papillomavirus

<400> SEQUENCE: 431
agattataag gaatacatgc                                              20

<210> SEQ ID NO 432
<211> LENGTH: 20
<212> TYPE: DNA
<213> ORGANISM: Human papillomavirus

<400> SEQUENCE: 432
agattataag gaatacatgc                                              20
```

<210> SEQ ID NO 433
<211> LENGTH: 20
<212> TYPE: DNA
<213> ORGANISM: Human papillomavirus

<400> SEQUENCE: 433
tgccaactct aatttttaagg                                              20

<210> SEQ ID NO 434
<211> LENGTH: 20
<212> TYPE: DNA
<213> ORGANISM: Human papillomavirus

<400> SEQUENCE: 434 ttctaattttt cgtgagtatc                                              20

<210> SEQ ID NO 435
<211> LENGTH: 20
<212> TYPE: DNA
<213> ORGANISM: Human papillomavirus

<400> SEQUENCE: 435
tcctactaag tttaagcact                                               20

<210> SEQ ID NO 436
<211> LENGTH: 20
<212> TYPE: DNA
<213> ORGANISM: Human papillomavirus

<400> SEQUENCE: 436
taacagtaat ttcaaggaat                                               20

<210> SEQ ID NO 437
<211> LENGTH: 20
<212> TYPE: DNA
<213> ORGANISM: Human papillomavirus

<400> SEQUENCE: 437 gaatttttaaa gaatatataa                                              20

<210> SEQ ID NO 438
<211> LENGTH: 20
<212> TYPE: DNA
<213> ORGANISM: Human papillomavirus

<400> SEQUENCE: 438 tagtaattttt aaagagtatt                                              20

<210> SEQ ID NO 439
<211> LENGTH: 20
<212> TYPE: DNA
<213> ORGANISM: Human papillomavirus

<400> SEQUENCE: 439
tgctaccaaa tttaagcagt                                               20

<210> SEQ ID NO 440
<211> LENGTH: 20
<212> TYPE: DNA
<213> ORGANISM: Human papillomavirus

<400> SEQUENCE: 440

```
agattataag gaatacatgc                                             20

<210> SEQ ID NO 441
<211> LENGTH: 20
<212> TYPE: DNA
<213> ORGANISM: Human papillomavirus

<400> SEQUENCE: 441
tgattataaa gagtacatgc                                             20

<210> SEQ ID NO 442
<211> LENGTH: 20
<212> TYPE: DNA
<213> ORGANISM: Human papillomavirus

<400> SEQUENCE: 442
tactaacttt aaagagtacc                                             20

<210> SEQ ID NO 443
<211> LENGTH: 20
<212> TYPE: DNA
<213> ORGANISM: Human papillomavirus

<400> SEQUENCE: 443
tactaacttt aaagagtacc                                             20

<210> SEQ ID NO 444
<211> LENGTH: 20
<212> TYPE: DNA
<213> ORGANISM: Human papillomavirus

<400> SEQUENCE: 444
tgccaactct aattttaagg                                             20

<210> SEQ ID NO 445
<211> LENGTH: 20
<212> TYPE: DNA
<213> ORGANISM: Human papillomavirus

<400> SEQUENCE: 445
ttctaatttt cgtgagtatc                                             20

<210> SEQ ID NO 446
<211> LENGTH: 20
<212> TYPE: DNA
<213> ORGANISM: Human papillomavirus

<400> SEQUENCE: 446
tcctactaag tttaagcact                                             20

<210> SEQ ID NO 447
<211> LENGTH: 20
<212> TYPE: DNA
<213> ORGANISM: Human papillomavirus

<400> SEQUENCE: 447
taacagtaat ttcaaggaat                                             20

<210> SEQ ID NO 448
<211> LENGTH: 20
<212> TYPE: DNA
<213> ORGANISM: Human papillomavirus

<400> SEQUENCE: 448
```

-continued

```
gaattttaaa gaatatataa                                          20

<210> SEQ ID NO 449
<211> LENGTH: 20
<212> TYPE: DNA
<213> ORGANISM: Human papillomavirus

<400> SEQUENCE: 449
tagtaatttt aaagagtatt                                          20

<210> SEQ ID NO 450
<211> LENGTH: 20
<212> TYPE: DNA
<213> ORGANISM: Human papillomavirus

<400> SEQUENCE: 450
tactaacttt aaagagtacc                                          20

<210> SEQ ID NO 451
<211> LENGTH: 20
<212> TYPE: DNA
<213> ORGANISM: Human papillomavirus

<400> SEQUENCE: 451
agattataag gaatacatgc                                          20

<210> SEQ ID NO 452
<211> LENGTH: 20
<212> TYPE: DNA
<213> ORGANISM: Human papillomavirus

<400> SEQUENCE: 452
tgattataaa gagtacatgc                                          20

<210> SEQ ID NO 453
<211> LENGTH: 20
<212> TYPE: DNA
<213> ORGANISM: Human papillomavirus

<400> SEQUENCE: 453
tgctaccaaa tttaagcagt                                          20

<210> SEQ ID NO 454
<211> LENGTH: 20
<212> TYPE: DNA
<213> ORGANISM: Human papillomavirus

<400> SEQUENCE: 454
tgctaccaaa tttaagcagt                                          20

<210> SEQ ID NO 455
<211> LENGTH: 20
<212> TYPE: DNA
<213> ORGANISM: Human papillomavirus

<400> SEQUENCE: 455
tgccaactct aattttaagg                                          20

<210> SEQ ID NO 456
<211> LENGTH: 20
<212> TYPE: DNA
<213> ORGANISM: Human papillomavirus
```

```
<400> SEQUENCE: 456 ttctaattttt cgtgagtatc                                              20

<210> SEQ ID NO 457
<211> LENGTH: 20
<212> TYPE: DNA
<213> ORGANISM: Human papillomavirus

<400> SEQUENCE: 457
tcctactaag tttaagcact                                               20

<210> SEQ ID NO 458
<211> LENGTH: 20
<212> TYPE: DNA
<213> ORGANISM: Human papillomavirus

<400> SEQUENCE: 458
taacagtaat ttcaaggaat                                               20

<210> SEQ ID NO 459
<211> LENGTH: 20
<212> TYPE: DNA
<213> ORGANISM: Human papillomavirus

<400> SEQUENCE: 459
gaattttaaa gaatatataa                                               20

<210> SEQ ID NO 460
<211> LENGTH: 20
<212> TYPE: DNA
<213> ORGANISM: Human papillomavirus

<400> SEQUENCE: 460
tgctaccaaa tttaagcagt                                               20

<210> SEQ ID NO 461
<211> LENGTH: 20
<212> TYPE: DNA
<213> ORGANISM: Human papillomavirus

<400> SEQUENCE: 461 tactaactttt aaagagtacc                                              20

<210> SEQ ID NO 462
<211> LENGTH: 20
<212> TYPE: DNA
<213> ORGANISM: Human papillomavirus

<400> SEQUENCE: 462
agattataag gaatacatgc                                               20

<210> SEQ ID NO 463
<211> LENGTH: 20
<212> TYPE: DNA
<213> ORGANISM: Human papillomavirus

<400> SEQUENCE: 463
tgattataaa gagtacatgc                                               20

<210> SEQ ID NO 464
<211> LENGTH: 20
<212> TYPE: DNA
<213> ORGANISM: Human papillomavirus
```

<400> SEQUENCE: 464
tagtaatttt aaagagtatt 20

<210> SEQ ID NO 465
<211> LENGTH: 20
<212> TYPE: DNA
<213> ORGANISM: Human papillomavirus

<400> SEQUENCE: 465
tagtaatttt aaagagtatt 20

<210> SEQ ID NO 466
<211> LENGTH: 20
<212> TYPE: DNA
<213> ORGANISM: Human papillomavirus

<400> SEQUENCE: 466
tgccaactct aattttaagg 20

<210> SEQ ID NO 467
<211> LENGTH: 20
<212> TYPE: DNA
<213> ORGANISM: Human papillomavirus

<400> SEQUENCE: 467
ttctaatttt cgtgagtatc 20

<210> SEQ ID NO 468
<211> LENGTH: 20
<212> TYPE: DNA
<213> ORGANISM: Human papillomavirus

<400> SEQUENCE: 468
tcctactaag tttaagcact 20

<210> SEQ ID NO 469
<211> LENGTH: 20
<212> TYPE: DNA
<213> ORGANISM: Human papillomavirus

<400> SEQUENCE: 469
taacagtaat ttcaaggaat 20

<210> SEQ ID NO 470
<211> LENGTH: 20
<212> TYPE: DNA
<213> ORGANISM: Human papillomavirus

<400> SEQUENCE: 470
tagtaatttt aaagagtatt 20

<210> SEQ ID NO 471
<211> LENGTH: 20
<212> TYPE: DNA
<213> ORGANISM: Human papillomavirus

<400> SEQUENCE: 471
tgctaccaaa tttaagcagt 20

<210> SEQ ID NO 472
<211> LENGTH: 20
<212> TYPE: DNA

```
<213> ORGANISM: Human papillomavirus

<400> SEQUENCE: 472
tactaacttt aaagagtacc                                              20

<210> SEQ ID NO 473
<211> LENGTH: 20
<212> TYPE: DNA
<213> ORGANISM: Human papillomavirus

<400> SEQUENCE: 473
agattataag gaatacatgc                                              20

<210> SEQ ID NO 474
<211> LENGTH: 20
<212> TYPE: DNA
<213> ORGANISM: Human papillomavirus

<400> SEQUENCE: 474
tgattataaa gagtacatgc                                              20

<210> SEQ ID NO 475
<211> LENGTH: 20
<212> TYPE: DNA
<213> ORGANISM: Human papillomavirus

<400> SEQUENCE: 475
gaattttaaa gaatatataa                                              20

<210> SEQ ID NO 476
<211> LENGTH: 20
<212> TYPE: DNA
<213> ORGANISM: Human papillomavirus

<400> SEQUENCE: 476
gaattttaaa gaatatataa                                              20

<210> SEQ ID NO 477
<211> LENGTH: 20
<212> TYPE: DNA
<213> ORGANISM: Human papillomavirus

<400> SEQUENCE: 477
tgccaactct aattttaagg                                              20

<210> SEQ ID NO 478
<211> LENGTH: 20
<212> TYPE: DNA
<213> ORGANISM: Human papillomavirus

<400> SEQUENCE: 478
ttctaatttt cgtgagtatc                                              20

<210> SEQ ID NO 479
<211> LENGTH: 20
<212> TYPE: DNA
<213> ORGANISM: Human papillomavirus

<400> SEQUENCE: 479
tcctactaag tttaagcact                                              20

<210> SEQ ID NO 480
<211> LENGTH: 20
```

```
<212> TYPE: DNA
<213> ORGANISM: Human papillomavirus

<400> SEQUENCE: 480
gaattttaaa gaatatataa                                               20

<210> SEQ ID NO 481
<211> LENGTH: 20
<212> TYPE: DNA
<213> ORGANISM: Human papillomavirus

<400> SEQUENCE: 481 tagtaattt aaagagtatt                                                20

<210> SEQ ID NO 482
<211> LENGTH: 20
<212> TYPE: DNA
<213> ORGANISM: Human papillomavirus

<400> SEQUENCE: 482
tgctaccaaa tttaagcagt                                               20

<210> SEQ ID NO 483
<211> LENGTH: 20
<212> TYPE: DNA
<213> ORGANISM: Human papillomavirus

<400> SEQUENCE: 483
tactaacttt aaagagtacc                                               20

<210> SEQ ID NO 484
<211> LENGTH: 20
<212> TYPE: DNA
<213> ORGANISM: Human papillomavirus

<400> SEQUENCE: 484
agattataag gaatacatgc                                               20

<210> SEQ ID NO 485
<211> LENGTH: 20
<212> TYPE: DNA
<213> ORGANISM: Human papillomavirus

<400> SEQUENCE: 485
tgattataaa gagtacatgc                                               20

<210> SEQ ID NO 486
<211> LENGTH: 20
<212> TYPE: DNA
<213> ORGANISM: Human papillomavirus

<400> SEQUENCE: 486
taacagtaat ttcaaggaat                                               20

<210> SEQ ID NO 487
<211> LENGTH: 20
<212> TYPE: DNA
<213> ORGANISM: Human papillomavirus

<400> SEQUENCE: 487
taacagtaat ttcaaggaat                                               20

<210> SEQ ID NO 488
```

```
<211> LENGTH: 20
<212> TYPE: DNA
<213> ORGANISM: Human papillomavirus

<400> SEQUENCE: 488
tgccaactct aattttaagg                                              20

<210> SEQ ID NO 489
<211> LENGTH: 20
<212> TYPE: DNA
<213> ORGANISM: Human papillomavirus

<400> SEQUENCE: 489
ttctaatttt cgtgagtatc                                              20

<210> SEQ ID NO 490
<211> LENGTH: 20
<212> TYPE: DNA
<213> ORGANISM: Human papillomavirus

<400> SEQUENCE: 490
taacagtaat ttcaaggaat                                              20

<210> SEQ ID NO 491
<211> LENGTH: 20
<212> TYPE: DNA
<213> ORGANISM: Human papillomavirus

<400> SEQUENCE: 491
gaattttaaa gaatatataa                                              20

<210> SEQ ID NO 492
<211> LENGTH: 20
<212> TYPE: DNA
<213> ORGANISM: Human papillomavirus

<400> SEQUENCE: 492
tagtaatttt aaagagtatt                                              20

<210> SEQ ID NO 493
<211> LENGTH: 20
<212> TYPE: DNA
<213> ORGANISM: Human papillomavirus

<400> SEQUENCE: 493
tgctaccaaa tttaagcagt                                              20

<210> SEQ ID NO 494
<211> LENGTH: 20
<212> TYPE: DNA
<213> ORGANISM: Human papillomavirus

<400> SEQUENCE: 494 tactaactttt aaagagtacc                                             20

<210> SEQ ID NO 495
<211> LENGTH: 20
<212> TYPE: DNA
<213> ORGANISM: Human papillomavirus

<400> SEQUENCE: 495
agattataag gaatacatgc                                              20
```

```
<210> SEQ ID NO 496
<211> LENGTH: 20
<212> TYPE: DNA
<213> ORGANISM: Human papillomavirus

<400> SEQUENCE: 496
tgattataaa gagtacatgc                                              20

<210> SEQ ID NO 497
<211> LENGTH: 20
<212> TYPE: DNA
<213> ORGANISM: Human papillomavirus

<400> SEQUENCE: 497
tcctactaag tttaagcact                                              20

<210> SEQ ID NO 498
<211> LENGTH: 20
<212> TYPE: DNA
<213> ORGANISM: Human papillomavirus

<400> SEQUENCE: 498
tcctactaag tttaagcact                                              20

<210> SEQ ID NO 499
<211> LENGTH: 20
<212> TYPE: DNA
<213> ORGANISM: Human papillomavirus

<400> SEQUENCE: 499
tgccaactct aattttaagg                                              20

<210> SEQ ID NO 500
<211> LENGTH: 20
<212> TYPE: DNA
<213> ORGANISM: Human papillomavirus

<400> SEQUENCE: 500
tcctactaag tttaagcact                                              20

<210> SEQ ID NO 501
<211> LENGTH: 20
<212> TYPE: DNA
<213> ORGANISM: Human papillomavirus

<400> SEQUENCE: 501
taacagtaat ttcaaggaat                                              20

<210> SEQ ID NO 502
<211> LENGTH: 20
<212> TYPE: DNA
<213> ORGANISM: Human papillomavirus

<400> SEQUENCE: 502
gaattttaaa gaatatataa                                              20

<210> SEQ ID NO 503
<211> LENGTH: 20
<212> TYPE: DNA
<213> ORGANISM: Human papillomavirus

<400> SEQUENCE: 503
tagtaatttt aaagagtatt                                              20
```

```
<210> SEQ ID NO 504
<211> LENGTH: 20
<212> TYPE: DNA
<213> ORGANISM: Human papillomavirus

<400> SEQUENCE: 504
tgctaccaaa tttaagcagt                                              20

<210> SEQ ID NO 505
<211> LENGTH: 20
<212> TYPE: DNA
<213> ORGANISM: Human papillomavirus

<400> SEQUENCE: 505
tactaacttt aaagagtacc                                              20

<210> SEQ ID NO 506
<211> LENGTH: 20
<212> TYPE: DNA
<213> ORGANISM: Human papillomavirus

<400> SEQUENCE: 506
agattataag gaatacatgc                                              20

<210> SEQ ID NO 507
<211> LENGTH: 20
<212> TYPE: DNA
<213> ORGANISM: Human papillomavirus

<400> SEQUENCE: 507
tgattataaa gagtacatgc                                              20

<210> SEQ ID NO 508
<211> LENGTH: 20
<212> TYPE: DNA
<213> ORGANISM: Human papillomavirus

<400> SEQUENCE: 508
ttctaatttt cgtgagtatc                                              20

<210> SEQ ID NO 509
<211> LENGTH: 20
<212> TYPE: DNA
<213> ORGANISM: Human papillomavirus

<400> SEQUENCE: 509
ttctaatttt cgtgagtatc                                              20

<210> SEQ ID NO 510
<211> LENGTH: 20
<212> TYPE: DNA
<213> ORGANISM: Human papillomavirus

<400> SEQUENCE: 510
ttctaatttt cgtgagtatc                                              20

<210> SEQ ID NO 511
<211> LENGTH: 20
<212> TYPE: DNA
<213> ORGANISM: Human papillomavirus

<400> SEQUENCE: 511
tcctactaag tttaagcact                                              20
```

-continued

<210> SEQ ID NO 512
<211> LENGTH: 20
<212> TYPE: DNA
<213> ORGANISM: Human papillomavirus

<400> SEQUENCE: 512
taacagtaat ttcaaggaat                                              20

<210> SEQ ID NO 513
<211> LENGTH: 20
<212> TYPE: DNA
<213> ORGANISM: Human papillomavirus

<400> SEQUENCE: 513
gaattttaaa gaatatataa                                              20

<210> SEQ ID NO 514
<211> LENGTH: 20
<212> TYPE: DNA
<213> ORGANISM: Human papillomavirus

<400> SEQUENCE: 514
tagtaatttt aaagagtatt                                              20

<210> SEQ ID NO 515
<211> LENGTH: 20
<212> TYPE: DNA
<213> ORGANISM: Human papillomavirus

<400> SEQUENCE: 515
tgctaccaaa tttaagcagt                                              20

<210> SEQ ID NO 516
<211> LENGTH: 20
<212> TYPE: DNA
<213> ORGANISM: Human papillomavirus

<400> SEQUENCE: 516 tactaactttt aaagagtacc                                             20

<210> SEQ ID NO 517
<211> LENGTH: 20
<212> TYPE: DNA
<213> ORGANISM: Human papillomavirus

<400> SEQUENCE: 517
agattataag gaatacatgc                                              20

<210> SEQ ID NO 518
<211> LENGTH: 20
<212> TYPE: DNA
<213> ORGANISM: Human papillomavirus

<400> SEQUENCE: 518
tgattataaa gagtacatgc                                              20

<210> SEQ ID NO 519
<211> LENGTH: 20
<212> TYPE: DNA
<213> ORGANISM: Human papillomavirus

<400> SEQUENCE: 519

```
tgccaactct aattttaagg                                         20

<210> SEQ ID NO 520
<211> LENGTH: 20
<212> TYPE: DNA
<213> ORGANISM: Human papillomavirus

<400> SEQUENCE: 520
tgccaactct aattttaagg                                         20
```

ALLELE-SPECIFIC MUTATION DETECTION ASSAY USING AN ENZYME-DISABLING AGENT

CROSS-REFERENCE TO RELATED APPLICATIONS

This application is a continuation of International Application PCT/GB2004/001766 filed Apr. 26, 2004, the entire content of which is expressly incorporated herein by reference thereto.

FIELD OF THE INVENTION

The present invention relates to an improved assay for detecting mutations and genetic variations based upon the use of allele-specific or type-specific probes or primers (i. e. allele-specific oligomers), or more generally, oligomers specific for particular target or variant bases in a target sequence to be analysed.

BACKGROUND OF THE INVENTION

Single nucleotide changes in human genes and surrounding DNA may cause genetic disorders and are currently believed to reveal the cause of individual susceptibility to different diseases. The most common type of genetic diversity is single nucleotide polymorphism (SNP). Therefore, accurate and sensitive analysis of SNPs may play a central role in DNA diagnostics. Analysis of SNPs is useful in applications including mapping, linkage studies and pharmacogenoics.

A number of new methods are now available for rapid automated scoring of SNPs (A. Ahmadian and J. Lundeberg, 2002, Biotechniques, 1122-1137). Many methods originate from hybridization techniques to discriminate between allelic variants. The use of microarrays with oligonucleotide reagents immobilized on small surfaces in miniaturized assays is a frequently proposed approach for large-scale mutation analysis and high-throughput genotyping of SNPs (D. Wang et al, 1998, Science, 1077-1082). Microarray hybridization of PCR fragments to allele-specific oligonucleotide probes (ASO) relies on the thermal stability of the PCR fragment and the short probe and has been used in large-scale SNP genotyping. However, the limitation of this technique lies in the fact that there are extremely small differences in the duplex stability between a perfect match and a mismatch at one base and therefore, for accurate analysis this approach requires redundant probes. To enhance the discrimination power of microarray based mutation/polymorphism analysis, enzymatic reactions have been performed on the oligonucleotide arrays (J. Hirschhorn et al, 2000 PNAS, 12164-12169 and T. Pastinen et al, 2000, Genome Research, 1031-1042).

Other technologies which have been shown to be useful for SNP genotyping are minisequencing (Pastinen et al. (1997) Genome Res. 7: 606), mass spectrometry (Laken et al. (1998) Nat. Biotechnol. 16: 1352) and Pyrosequencing (Ahmadian et al. (2000) Anal. Biochem. 280: 103), the latter relying on incorporation of nucleotides by DNA polymerase with an enzymatic cascade converting the released pyrophosphate (PPi) into detectable light.

The use of pairs of allele-specific primers with alternative bases at the 3' end has been used to identify single base variations. Higgins et al. (1997) Biotechniques 23: 710; Newton et al. (1989) Lancet 2: 1481; and Goergen et al. (1994) J. Med. Virol. 43: 97. This method exploits the difference in primer extension efficiency catalysed by a DNA polymerase of a matched over a mismatched primer 3'-end. Generally, a sample is divided into two extension reaction mixtures that contain the same reagents except for the primers, which differ at the 3'-end. The alternating primer is designed to match one allele perfectly but mismatch the other allele at the 3'-end. Because the polymerase differs in extension efficiency for matched versus mismatched 3'-ends, the allele-specific extension reaction thus provides information on the presence or absence of one allele.

Allele-specific extension has traditionally been applied in the context of genetic variation such as allelism where a given DNA sequence (e.g., a gene) occupying a particular locus on a chromosome or linkage structure may occur in two or more alternate and different forms (typically biallelic variation where two alternate alleles exist, but occasionally there may be three or four or more (where more than single base changes are concerned) different allelic forms). Similarly, the same principle may be used to distinguish different mutations or base changes which may occur at a given locus or target site (i.e. "mutation-specific" primers, by analogy).

It will be appreciated from this, therefore, that the basic principle of "allele-specific" discrimination by "allele-specific" primer extension can be applied to any situation where genetic variation can occur at a given locus or target site, and that such variants or differences can be discriminated by using primers designed to be specific for the particular variations (variants) or base differences concerned. Thus, for example, in the case of genotyping applications, where it may be desired to detect or determine what base(s) is (are) present at a particular location(s), it will be seen that not all organisms (e.g. viruses) may exhibit allelism (i.e. carry two or more alleles), but different forms or strains (types) thereof may be distinguished (or "typed") using this general principle, namely the use of different specific primers, each specific for a particular "type", or variant base which may occur (i.e. "type"- or "variant"-specific primers). "Allele-specific" extension may thus be recognised as extending to any situation where a polymerase enzyme, for example DNA or RNA polymerase or reverse transcriptase, is used to extend a primer which is matched, but not a primer which is mismatched, in the context of any given base change or genetic variation, where a primer may "match" one of the variants which may occur, and hence "mismatch" the other.

Allele-specific primer extension takes advantage of the discrimination properties of a polymerase in extension of a 3'-end matched primer. This method has been employed previously to identify single base variations (C. Newton et al, 1989, Nucleic Acids Research, 2503-2516) but it is generally acknowledged that certain mismatches, such as G:T or C:A are poorly discriminated by the employed polymerase enzyme. This poor discrimination property of the polymerase has consistently been observed in applications of this technique (S. Ayyadevara et al, 2000, Analytical Biochemistry, 11-18, J. Day et al, 1999, Nucleic Acids Research, 1810-1818 and S. Kwok et al, 1990, Nucleic Acids Research, 999-1005). In these cases, the polymerase extends the mismatched primer-templates in the presence of nucleotides.

The applicants have previously shown that the discriminatory ability of the polymerase enzyme in the context of "allele-specific" extension assays depends upon relative reaction kinetics. Extension of mismatched primer-template configurations occurs with slower reaction kinetics in comparison to the faster extension of matched primer-template configurations. The kinetic difference is usually not distinguishable in end-point analysis, such as in allele-specific PCR, because extension of a single mismatched substrate in the first cycle will lead to perfectly matched primer-templates in subsequent cycles, yielding comparable amounts of end products for both matched and mismatched configurations.

The applicants have further previously demonstrated that the use of a nucleotide-degrading enzyme (particularly apyrase) during the assay improves discrimination in allele-specific extension assays by exploiting this difference in the relative kinetics (A. Ahmadian et al, 2001, Nucleic Acids Research, Volume 29, No. 24 e121 and D. O'Meara et al, 2002, Nucleic Acids Research, Volume 30 No. 15 e75 and WO 02/068684 of Pyrosequencing AB. In apyrase-mediated allele-specific extension (AMASE), when the reaction kinetics are fast (i.e. with a matched primer) the primer-template is extended by the polymerase before the apyrase (or other nucleotide-degrading enzyme(s)) degrades the nucleotides. However, when the reaction kinetics are slow, due to the mismatched primer, apyrase degrades the nucleotides before they can be incorporated and prevents or hinders extension of the mismatched primer-template.

Although the use of apyrase (or other nucleotide-degrading enzyme) has circumvented some of the main difficulties of allele-specific primer extension assays, there are some disadvantages related to this technique. Primarily, apyrase degrades the nucleoside triphosphates to nucleoside diphosphates and there can be a problem with contamination with kinases in the reaction mixture that are able to convert any nucleoside diphosphates back to nucleoside triphosphates. These nucleoside triphosphates may then be used by the polymerase to extend a mismatched primer-template. One solution to this problem may be to use an additional enzyme that is able to degrade the nucleoside diphosphates to nucleoside monophosphates. This, however, has the disadvantage of proliferating reagents. Secondly, there is evidence available that apyrase binds to DNA templates and primers (M. Ronaghi, 2000, Analytical Biochemistry, 282-288). The binding of apyrase to DNA makes the enzyme unavailable in the reaction mixture, particularly when the quantity of DNA to be analysed is high. One solution to this problem is to use additional protein in the assay. This protein may be single-stranded DNA binding protein (SSB). SSB binds to single-stranded DNA and releases apyrase into the reaction mixture. Again, however, this entails the use of further reagents. Thirdly, apyrase is not a thermostable enzyme and is inactive at higher temperatures, which is a considerable disadvantage when more stringent temperature conditions are required. It is well-known in molecular biotechnology that at lower temperatures the DNA forms different secondary structure, including loop formation. In addition to DNA loops, lower temperature is the major cause of non-specific hybridization. These aspects can cause problems in the AMASE assay which requires lower temperatures to allow the apyrase to perform the degradation of nucleotide triphosphates. Formation of DNA loops on mismatched oligonucleotide primers gives rise to self-extension of the primers leading to incorrect results. Non-specific hybridization is a major problem especially in multiplex genotyping assays (e.g. where multiple primers are present), giving rise to false signals. This problem can in most cases be circumvented by using higher and more stringent temperature conditions. However, the stringent temperature conditions cannot be achieved by the AMASE assay without significant loss of apyrase activity.

There is thus a continuing need in the art for improved methods of allele-specific extension analysis and the present invention addresses this need.

The method of the present invention solves the deficiencies of the prior art methods by providing a method of allele-specific or type-specific extension that allows more accurate discrimination between matched and mismatched configurations. The present methods are useful for any type of genetic analysis based on detecting or identifying particular or specific base changes, for example high throughput SNP analysis and genotyping assays. The present methods may be used also for detecting or screening for mutations (such as substitutions, insertions and deletions) and genomic variations, and particularly single nucleotide polymorphisms (SNPs), and may be used with single stranded or double stranded DNA targets.

BRIEF SUMMARY OF THE INVENTION

In other words, the present invention provides a method of allele-specific or type-specific primer extension useful for accurate analysis of any mutation(s) and/or genetic variation(s) (i.e. single nucleotide polymorphisms), or indeed any base change it is desired to detect and/or identify.

The method of the invention again takes advantage of the fact that polymerase enzymes extend mismatched primer-templates with slower reaction kinetics compared to matched primer-template. However, rather than removing nucleotides before they can be incorporated in the slow (mismatched) reaction situation, the present invention relies instead on inactivating, or disabling, the polymerase in such a manner that permits extension in reactions having fast kinetics (i.e. matched primer to target) but wherein the polymerase is inactivated or disabled before extension can take place in reactions having slow kinetics (i.e. mismatched primers).

Although the present invention was initially developed as an improvement to the technique of "allele-specific" primer extension, the inventors believe that the basic principles of improving "allele-specific" discrimination by improving the discriminating properties of the enzyme used (e.g. polymerase) may be applied to any situation which relies upon the use of an allele-specific primer or probe (i.e. any allele-specific oligomer) which is subjected to an enzymatic reaction as part of the detection strategy. In other words, the basic principles of the present invention may be applied to any method which uses an allele-specific oligonucleotide reagent (e.g. such as a probe or primer) i.e. an "allele-specific" oligomer.

A number of such "allele-specific" methods are known in the art. In addition to "allele-specific" primer extension, an "allele-specific" ligation-based assay may be performed wherein the probes used for ligation are "allele-specific". Thus, analogously to the polymerase primer extension system, the probes for ligation may be designed to be "allele-specific" (or more particularly "variant-base specific") such that ligation will only occur (or will occur with greater efficiency or at higher rate) when the probe is "matched" to the base it is desired to detect. Since ligation of two (or more) oligonucleotide probes by ligase leads to a single longer oligo- or poly-nucleotide molecule, it may be viewed as a method of "oligonucleotide elongation" analogous to primer extension (wherein a primer oligonucleotide is extended, or elongated, by incorporation of nucleotides). Thus, both ligation assays and primer extension assays may be viewed as examples of "oligomer elongation" assays, and more particularly, enzyme-catalysed oligomer elongation assays.

DETAILED DESCRIPTION OF THE INVENTION

However, as discussed further below, not all ligation assays rely on the use of two or more probes which are ligated together, and in some cases a single probe may be used, wherein the two ends of the probe are ligated together (e.g. a "padlock probe" as described further below). In this case, although a formal "elongation" by addition of additional components does not take place, in one sense the probe can be viewed as being "elongated" at its end (e.g. at its 3' end) by ligation to the other end (i.e. the "3' end" is elongated). Thus, all ligation assays whether involving one probe or multiple probes (i.e. 2 or more probes) are viewed herein as an "oligomer elongation" assay.

Particularly, in one embodiment, an oligonucleotide ligation assay (OLA) can be used to detect alleles, and relies upon an enzymatic oligomer elongation step wherein the ligase covalently joins two oligonucleotide probes (oligomers) bound to the target nucleic acid. The two oligonuleotide probes are constructed to hybridize to adjacent sequences in the target nucleic acid, the join site sited at the position which is allele/type-specific. The ligase should only covalently join the two oligonucleotide probes if they are perfectly hybridized, however the technique is not completely reliable, and the ligase enzyme may link two oligonucleotide probes where at least one probe is mismatched to the "allele specific" or type-specific site in the target. In a preferred embodiment one probe is mismatched. However, it is possible to perform the assay using a second probe which is also mismatched to the template or target sequence. The present inventors believe that ligation of a mismatched probe occurs with slower reaction kinetics than ligation of a matched probe, which may be exploited using the method of the invention in order to more precisely define the base present at the target site of the target nucleic acid—e.g. the allele-specific or type-specific base.

Thus, analogously to the disablement of the polymerase enzyme in primer-extension reactions, in the ligase-elongation reaction, the enzyme, namely ligase, may likewise be disabled in such a manner that permits ligation (e.g. elongation) in reactions having fast kinetics (i.e. matched oligomer (probe) to target) but wherein the enzyme is inactivated or disabled before the reaction (i.e. ligation) can take place in reactions having slow kinetics (i.e. mismatched oligomers). In this embodiment, the method of the invention, therefore, again also takes advantage of the fact that ligase enzymes ligate mismatched probe-templates with slower reaction kinetics compared to matched probe-templates. Generally, therefore, the invention takes advantage of the principle of slower reaction kinetics of an enzyme reaction on an oligomer, when the oligomer(s) (e.g. a probe or primer) is mismatched to the "allele-specific" (or "variant" or "type") site, as compared to when the oligomer is matched.

Thus, specific oligomers (e.g. probes or primers) are used, which are designed to be specific (or selective) for a particular base at a predetermined position which it is desired to detect; a given oligomer will thus either "match" a particular base which may occur at the base or "mismatch" it. (Conveniently, but as explained further below, not necessarily, the oligomer will "match" the selected target base by comprising a 3' terminal base which is complementary to the target base, as in conventional allele-specific technology, and will "mismatch" other bases which may occur by having a non-complementary (3' terminal base). Such oligomers are allowed to bind (or hybridise or anneal to) the target or template nucleic acid and an enzymatic detection reaction (specifically in the case of an elongation assay, an oligomer elongation reaction) is performed (e.g. polymerase-catalysed elongation of a primer or ligase-catalysed elongation of a probe).

Depending upon which base is present at the target position, an oligomer (e.g. primer or probe) will be a match or mismatch for the target. The enzyme discriminates between a match and mismatch, and exhibits faster reaction kinetics when the oligomer matches the template. Thus, by comparing the respective oligomer enzymatic detection reactions (i.e. elongation reactions) using the matched and mismatched oligomers, for example by comparing the respective reaction (i.e. elongation) efficiencies (e.g. by measuring the difference in primer extension efficiency by the DNA polymerase of a matched over a mismatched primer or by measuring the difference in ligation efficiency by the DNA ligase of a matched over a mismatched probe) the presence or absence of a particular target base may be determined. In accordance with the present invention, it has been found that disabling the enzyme in the reaction mixture minimizes the reaction (i.e. elongation) of mismatched oligomer (e.g. primer/probe) configurations by removal of enzymatic activity before the reaction (i.e. elongation) can take place but allows the enzymatic reaction to take place (i.e. elongation) when reaction kinetics are fast, i.e. in a matched configuration. The present invention thus reduces or eliminates false positive results seen in prior art methods, and allows higher stringency conditions to be used.

Thus, in one aspect, the invention provides a method of detecting a base at a pre-determined position in a nucleic acid molecule, said method comprising:

performing enzymatic oligomer elongation reactions using base-specific detection oligomers, each oligomer being specific for a particular base at said predetermined position, and comparing said enzymatic oligomer elongation reactions to determine which base is present at said position, wherein an enzyme-disabling agent is present during the enzymatic oligomer elongation reaction.

As explained above, this method of the invention may be used to detect a base change at a particular pre-determined position, by determining which base is present at that position. The method may thus be used to detect mutations, or any genetic variation (e.g. different genotypes, allelic variation, SNPs etc.) based on base changes. The base detected may thus be allele-specific. The method has particular utility in the detection of single base changes or single nucleotide polymorphisms (SNPs). The oligomers (e.g. primer or probe) used may thus be allele-specific. The method may also be used to detect which bases are present in a given position (e.g. in a target nucleotide sequence) in a typing (i.e. genotyping) procedure. The method may thus be used to distinguish individuals or target sequences, e.g. in a typing procedure. The target base and the oligomer may thus be "type-specific". The method may be used to detect base changes (e.g. polymorphisms or mutations or base differences between individuals) which are known or unknown. Thus known or unknown base changes may be identified. It will be seen therefore that the "base-specific" oligomer may be specific for any given base change, e.g. allele, mutation, genetic variant, type etc., it is desired to detect. Such a base-specific oligomer may thus also be viewed as a "variant-specific" oligomer, i.e. a oligomer specific for a particular or given variant base which it is desired to detect, namely a base which may be variant at any given or specified particular or predetermined position.

As discussed above, allele-specific assays based on the use of allele-specific primers and probes are well known in the art and widely described in the literature. Any such "allele-specific" primers or probes may be used as the "base-specific" oligomers in the method of the invention. Thus, the base-specific oligomer is designed to be specific for, or selective for, a particular base, for example a base the presence or absence of which it is desired to detect. Such a oligomer will only be elongated (e.g. detectably elongated) or will have a greater elongation efficiency (or higher rate of elongation) in the presence of that base in the target (i.e. pre-determined) position in the target nucleic acid molecule which acts as template in the enzymatic oligomer elongation reaction, and will not be elongated (or will be elongated at a lower rate or with reduced efficiency) in the absence of that base. Such oligomers therefore "match" or "mismatch" the particular base for which they are selective or specific.

Such oligomers are thus specific or selective for a particular variant base and as explained above may be regarded as "variant-specific" oligomers. As used herein, the term "oligomer" refers to a nucleic acid fragment (e.g. oligonucleotide) which can anneal to the target oligonucleotide, and which can be detected in an enzymatic detection reaction (e.g. elongated in an enzymatic elongation reaction). An oligomer may thus be any "base-specific" oligonucleotide. It may thus be viewed as any oligonucleotide reagent which may be detected (i.e. a "detection oligomer") in a "base-specific" manner in an enzymatic assay. The term includes primers, probes and any short (e.g. up to 40 nucleotides in length) nucleic acid sequence which can anneal to the target and undergo enzymatic elongation. The oligomer may be any convenient length, (i.e. 5 to 40 nucleotides, 5 to 30 nucleotides, 5 to 20 nucleotides) and may be composed of any nucleic acid residue type i.e. RNA, DNA, or PNA (peptide nucleic acid) or any derivative or modification thereof, as long as it can be subjected to an enzymatic detection (e.g. elongation) reaction. Thus, as used herein, the term "oligomer" can refer to a primer or a probe. A primer is a short nucleic acid sequences (e.g. up to 40 nucleotides), which is often synthetic, which binds specifically to a single strand of a target nucleic acid sequence and is capable of initiating synthesis of a complementary strand, using a suitable polymerase enzyme. The primer is thus elongated using an enzyme, in a reaction generally referred to as primer-extension.

Probes are nucleic acid fragments, which optionally may be labelled and are used in hybridization assays. Any suitable probes well known in the art may be used in the detection of allele-specific or type-specific bases etc. As discussed above, a probe may be an oligonucleotide or fragment used in a ligation assay, i.e. for ligation by a ligase enzyme. Therefore, mention can be made of padlock probes, which are linear nucleic acid probes which can be hybridised on the target sequence so that the two ends are close to or next to each other. The two ends can be covalently joined by DNA or RNA ligase forming a circularized probe. Thus a circularized probe is obtained, and the 3' end of the probe is "elongated" in the reaction.

The base to be detected at the pre-determined position (i.e. the target base) may be any base which may occur at that position. Thus, for example, in the context of allelic variation, it may be a base corresponding to one of the alleles which may occur. In the case of a mutation, it may be a non-mutated (e.g. wild-type) base or any mutated base which is known to occur. In the case of an unknown mutation, the target base may be any base other than the non-mutated base. In the case of a single nucleotide polymorphism, it may be any of the bases known or suspected to occur at that position and so on. In genotyping, where known genotypes are concerned, the target base may be any of the known variant bases which may occur at the particular position in question, or where determining unknown genotypes it may of course be any base.

Most conveniently, as discussed above, such base-specific oligomers may be designed to comprise a "match" or "mismatch" for the target base at their 3' end (i.e. at the 3' terminus). Thus the 3' base (i.e. the base at the 3' terminus) of the oligomer is designed either to match (i.e. to be complementary) to a particular base (e.g. a particular allele, or mutation or variant base) or mismatch it (i.e. be non-complementary). As explained above, in the context of a mutation, in one oligomer the 3' base may be complementary to the non-mutated (e.g. wild-type) base and in a second oligomer i.e. may be complementary to a mutated base (e.g. the mutation it is desired to detect). In the case of elongation of the oligomer via ligase enzymes, the 5' base of the oligomer can be designed to either match to a particular base or mismatch it. However, it is preferred that the oligomer has an allele- or base-specific residue at the 3' end.

Thus, in the context of a known mutation or biallelic variation (e.g. SNP), for example, two oligomers may be used, the first "matched" to the one base which may occur, and the second "matched" to the other base which may occur. Where more than one base may occur (e.g. where more than one mutant base or alternative allele exists or in other contexts where more than two different bases may occur (e.g. in genotyping)), more than two base-specific oligomers may be used, each specific for (or "matched to") each of the bases which may occur.

The method of the invention thus comprises the use of at least two (or two or more) base-specific oligomers, e.g. 2, 3 or 4 oligomers. As discussed further below, the method of the invention may be adapted to the detection of unknown mutations, simply by providing oligomers specific for each of the 4 bases (A, T, C or G) which may occur at a particular, (i.e. pre-determined) position (FIG. 4). Thus, each position in a target sequence may be "scanned" for mutations. All positions in a target template may be sequenced and possible mutations can be identified by using an overlapping set of oligomers (FIG. 5).

Although, as mentioned above, the use of base-specific oligomers which differ at their 3' terminus, or 5' terminus in the case of probes for a ligation-elongation assay, represents one way of performing the method, the method of the invention is not so limited, and alternative oligomer designs are also possible, as again is well known and widely described in the art. Thus, base-specific oligomers according to the present invention may comprise a match (or mismatch) for the target base at other positions, for example at the 3' −1 position of the oligomer (i.e. the penultimate base of the oligomer). Thus the "base-specific" (or "variant-specific") base in the oligomer need not be the 3' base, but it may be present at other positions e.g. the −1 or −2 (ante-penultimate) position. In addition, the oligomer may also comprise other modifications (e.g. other mismatches) at other positions to aid or improve "base-specificity" (i.e. discrimination between the "matched" and "mismatched" situation). Again, such principles of oligomer design are also discussed in the literature. Such modifications to the oligomer are more relevant to primer design than probe design.

In the method of the invention, an enzyme-catalyzed oligomer elongation reaction is used to detect mutations and genetic variations. Any suitable oligomer elongation reaction catalyzed by an enzyme may be used. As used herein, an "enzymatic oligomer elongation reaction" refers to a reaction wherein the oligomer (or more particularly an end of an oligomer) hybridized to the target nucleic acid is elongated, e.g. lengthened or enlarged or extended by means of one or more nucleotides or an oligonucleotide or further oligomer. Thus, in addition to incorporation of additional nucleotides or oligomer/oligonucleotide molecules, also encompassed, as explained above, is elongation wherein an end of an oligomer is elongated by ligation to the other end of a single oligomer molecule.

In a more general sense, the invention may thus be alternatively, or more broadly, viewed as providing a method of detecting a base at a pre-determined position in a nucleic acid molecule, said method comprising:

performing enzymatic detection reactions using base-specific detection oligomers, each oligomer being specific for a particular base at said predetermined position, and comparing said enzymatic detection reactions to determine which base is present at said position, wherein an enzyme-disabling agent is present during the enzymatic detection reaction.

The enzymatic detection reaction may be any enzyme-catalysed reaction involving a base-specific detection oligomer. It may advantageously be an enzymatic oligomer elongation reaction as described herein, above and below. The detection reaction may thus be any polymerase- or ligase-catalysed reaction. In the method of the invention, an enzyme-disabling agent may be used to improve discrimination between matched and unmatched base-specific oligomers in any enzymatic reaction involving said oligomers, and hence to improve specificity of said enzymatic reaction, wherein the non-specificity arises from the enzyme (e.g. wherein the enzyme used is not totally reliable in discriminating matches from mismatches).

In one embodiment of the invention, the oligomer used is a primer, and the primer is elongated via the addition of nucleotides, which is catalysed by a suitable polymerase enzyme. Primer elongation is more generally known as primer extension. Primer elongation (or extension) occurs when the primer is hybridized to the target nucleic acid and additional nucleotides are added to the 3' end of the primer in a reaction catalyzed by a polymerase enzyme or active subunit thereof. Any polymerase enzyme or active subunit thereof capable of primer extension may be used. Mention can be made of DNA polymerase, RNA polymerase, DNA dependent RNA polymerase (also known as reverse transcriptase) and active subunits thereof, such as the Klenow fragment of DNA polymerase.

The primer extension reactions may be performed in any convenient or desired way, as known in the art and described in the literature, for example as disclosed by Higgins et al. (1997) Biotechniques 23:710; Newton et al. (1989) Lancet 2:1481; Goergen et al. (1994) J. Med. Virol. 43:97; and Newton et al. (1989) Nucleic Acids Res. 17:2503. For example, the target nucleic acid molecule may be contacted with said base-specific primer in conditions under which hybridisation (or annealing) of the primers, and subsequently primer extension, may occur. Conveniently, "hybridization mixtures" comprising template (i.e. target nucleic molecule) and primer may be prepared or provided (i.e. 1 to 4 hybridisation mixtures depending on the number of primers used). Polymerase (e.g. DNA, RNA or DNA dependent RNA polymerase) and one or more nucleotides for the performance of the primer extension reaction may then be added. The enzyme-disabling agent (which in this case may be viewed as a polymerase-disabling reagent) may be included in the primer extension reaction mixture, or added separately.

An alternative embodiment of this invention involves the elongation of a base-specific oligomer by virtue of ligation to a "further" oligomer which hybridises to the target nucleic acid directly adjacent to the base-specific oligomer. A "further" or second oligomer is provided which hybridizes next (e.g. directly next) to the base-specific oligomer, at a position adjacent or substantially adjacent to the base of interest. Such a second/further oligomer is generally complementary to the target nucleic acid, e.g. it matches the target nucleic acid. However, as mentioned above, it may also mismatch the target nucleic acid, so long as the mismatch(es) do not compromise its ability to hybridise to the target and be subjected to a ligase reaction.

Further alternatively, in the case of a ligase assay based on a "padlock probe", only one base-specific oligomer is provided, and the two ends of the oligomer (i.e. padlock probe) hybridize next to each other on the target sequence. A 'padlock probe' thus provides the base-specific oligomer and the "further" oligomer with which to elongate the base-specific oligomer in one nucleic acid molecule.

With respect to the base-specific oligomers used in the "ligase" embodiments of the method of the invention, the base-specific position may be at the 3' or 5' end of the oligomers, as discussed previously. However, the presence of base-specific position at other positions e.g. 3'-1, 3'-2 etc. is not precluded. The elongation oligomer (defined herein as the "other" end of a single oligomer for a ligation assay e.g. a padlock probe, or a further/second probe) binds to the target immediately adjacent to the base-specific oligomer, at the base-specific position. The 'join' between the two oligomers is thus sited at the position of interest. In the assay, the join between the two oligomers is covalently joined in a ligation reaction catalysed by a suitable enzyme. Such enzymes include DNA and RNA ligase. The ligase enzyme should only ligate the oligomers if they are both perfectly complementary (matched) to the target at the join site. However, ligases have been known to covalently join oligomers where the base-specific oligomer is mismatched to the template, and the present invention seeks to reduce such errors.

The oligomer (probe) elongation reaction (ligation) may be performed in any convenient or desired way. For example, the target nucleic acid molecule may be contacted with said base-specific oligomer (or probe) in conditions under which hybridisation (or annealing) of the oligomers, and subsequent oligomer elongation (e.g. via ligation to a further oligomer or to the other end of the base-specific oligomer), may occur. Conveniently "hybridization mixtures" comprising template (i.e. target nucleic acid molecule) and base-specific oligomer may be prepared or provided (i.e. 1 to 4 hybridisation mixtures depending on the number of base-specific oligomers used). Ligase (DNA or RNA ligase) and optionally a further oligomer (in the case where multiple (i.e. two or more) probes are used) for the performance of the base-specific oligomer elongation reaction may then be added. The enzyme (i.e. ligase) disabling agent may be included in the elongation reaction mixture, or added separately.

Generally speaking, in all embodiments of the invention the enzyme disabling agent is preferably added after oligomer hybridization and preferably with the elongation (detection) reaction mixture (enzyme and optionally one or more nucleotides or second/further oligomers). The term "enzyme-disabling agent" as used herein includes any agent (e.g. all means and entities) capable of directly or indirectly preventing, reducing or removing the enzymatic catalytic activity. The enzyme disabling agent may thus be an agent which would "disable" any enzyme: (i.e. acts non-specifically, irrespective of the type of enzyme) or it may be an agent specific for the type of activity concerned, e.g. oligomer elongation activity, or more specifically polymerase and/or ligase activity. All that is required is that the "detection" enzyme (e.g. elongation enzyme) may be disabled. The "enzyme disabling agent" may thus be a functional inhibitor of enzyme action. It may function in any way to inactivate the enzyme activity, or prevent or hinder it from functioning in any way. It may thus be any enzyme inactivating agent. The disabling agent may thus, directly or via an interaction with another entity, degrade, inhibit, hinder or significantly reduce (i.e. reduced to 50%, 45%, 40%, 35%, 30%, 25%, 20%, 15%, 10%, 7%, 5%, 2% or 1% normal activity) enzyme activity. Several agents are known that will inhibit any enzyme activity, including high salt concentration (for example sodium or potassium chloride) or a protease capable of degrading the enzyme, as discussed in more detail below. Antibodies raised against the enzyme may also be used as inhibitors. Polymerase and/or ligase inhibitors may thus be used as the disabling agent in the method of the present invention.

When the oligomer elongation assay performed is a primer extension assay it may be catalysed by DNA, RNA or DNA dependent RNA polymerase (reverse transcriptase), as discussed previously.

Any suitable polymerase inhibitor well known in the art may be used in the method of the invention including, but not restricted to, phenol, salts such as sodium chloride and potassium chloride, heparin, ionic detergents such as SDS and sarkosyl, chloroform, xylene cyanol, bromophenol blue and inosine.

Agents that indirectly inhibit polymerase may also be used, for example agents that bind, chelate or otherwise reduce free $Mg^{2+}$ (magnesium ion) levels in the reaction mixture. $Mg^{2+}$ is a critical component required by polymerase, and thus reducing/removing $Mg^{2+}$ from the reaction mixture inhibits DNA polymerase. Suitable agents include EDTA (ethylene diamine tetracetic acid), EGTA (ethylenebis [oxyethylene trinitrilo]tetraacetic acid), flavanols and crown-flavanols and other chelators, although EDTA is the preferred agent. Alternatively, an antibody may be used that neutralises polymerase activity, for example via binding to the active site. Suitable antibodies that bind DNA polymerase have been described (see for example U.S. Pat. Nos. 5,338,671 and 5,565,340).

Where the elongation (detection reaction) is catalyzed by ligase, e.g. DNA ligase, any known inhibitor may be used, or an antibody raised to said enzyme may inhibit catalytic activity. Known inhibitors of human DNA ligase include arsolic and oleanolic acids from *Tricalysia niamniamensis* and other tritepenes such as aleuritolic acid. Certain flavonoids disrupt the activity also (Tan et al, Biochem J., 1996, 314, 993-1000). If *E. Coli* DNA ligase is used, this enzyme uses NAD as a cofactor, whereas the T4 bacteriophage DNA ligase requires ATP as a cofactor. Removal of these co-factors from the reaction mix via binding or enzyme-catalyzed means will inhibit the activity of the DNA ligase.

Preferably, the disabling agent is an enzyme that targets the enzyme used for elongation (detection), such as a protein-digesting enzyme. Such an enzyme can cleave proteins (peptide bonds) at specific or non-specific peptide bonds in the polypeptide chain. Any enzyme or combination of enzymes that are capable of specifically or non-specifically cleaving or damaging the polypeptide backbone of the enzyme and destroying or reducing the activity of the elongation/detection enzyme may be used. Such enzymes are described in the literature and many of them are commercially available. The disabling enzyme is preferably thermostable to allow the reaction to occur at the elevated reaction temperatures. Any suitable protein-degrading enzyme may be used, including, but not limited to serine proteases (trypsin, chymotrypsin, elastase), aspartate proteases (pepsin, lysozymes, renin), metalloproteases (carboxypeptidases, matrix metallopeptidases and cysteine proteases (papain, caspases and cathepsins). Preferably, the enzyme used is Proteinase K, and more preferably, the Proteinase K is thermostable.

Any suitable combination of one or more (i.e. 2, 3, 4, 5, 6, 7, 8, 9 or 10 or more) enzyme disabling agent(s) may be used. Thus, for example, a degrading enzyme may be used together with a direct enzyme inhibitor, or a chelator etc.

It will be understood that the amount, quantity or concentration of enzyme disabling agent, either alone or in combination with one or more further enzyme disabling agent(s), will be such that the enzyme is able to catalyse the detection reaction using a matched oligomer (e.g. elongation of a matched oligomer), i.e. perform the reaction (e.g. elongation) of the fast reaction situation (e.g. 3'-end matched oligomer-template). However, the concentration/amount of the agent(s) is such that the enzyme is inhibited, degraded, disabled or inactivated prior to catalysing reaction (e.g. elongation) of a mismatched oligomer, i.e. perform the reaction (e.g. elongation) of the slow reaction kinetics (e.g. 3'-end mismatched oligomer-template). Thus, an optimal amount of enzyme disabling agent will be used in the method of the invention, and this can vary dependent upon precise reaction conditions, nature of the oligomer, template enzyme etc. and may readily be determined by routine experimentation.

The enzyme disabling agent is preferably added with the oligomer elongation reaction mixture (i.e. the polymerase reaction mixture or the ligase reaction mixture) or reaction reagents after oligomer hybridization. Generally, the primer elongation mixture contains a polymerase, optionally means for detecting nucleotide incorporation and optionally nucleotides for incorporation. Normally, the probe ligation mixture contains a ligase and optionally a second probe which binds to the target nucleic acid directly adjacent to the base-specific probe, next to or close to the "variant"-specific base. Generally, the disabling agent is included during the elongation (detection) reaction step. It may thus be added with any or all of the elongation (detection) reaction reagents, or after they have been added, as long as it is present when the reaction is initiated (e.g. after the addition of the polymerase and together with the nucleotides or after the addition of the ligase and together with the further/second probe). In one embodiment, this may be achieved by adding a pre-heated (50 to 70° C.) mixture of primed-template, nucleotides and disabling agent to the polymerase.

Alternatively, as mentioned above, since it is required only that the enzyme disabling agent(s) is included during the elongation (detection) reaction step, this may be achieved simply by adding the agent(s) to the elongation (detection) reaction mixture prior to or simultaneously with the elongation (detection) reaction (i.e. the chain extension, nucleotide incorporation, probe incorporation or chain elongation etc.), e.g. prior to or simultaneously with, the addition of the enzyme, and/or substrates for elongation (or the detection reaction) (e.g. nucleotides or further/second probe) to the sample/primer.

In one embodiment, the enzyme disabling agent(s) may simply be included in solution in a reaction mix for the elongation (detection) reaction, which may be initiated by addition of the enzyme or any substrates for elongation (or for the detection reaction), for example nucleotides or a further/second oligomer, if appropriate.

In a preferred embodiment of the present method, the enzyme disabling agent is a protein-degrading enzyme.

Generally speaking, when the disabling agent is a protein-degrading enzyme, it is selected to have kinetic characteristics relative to the elongation or detection enzyme to allow the enzyme to catalyse (reaction (e.g. elongation) of the matched oligomer(e.g. 3'-match) but not catalyse reaction (e.g. elongation) of the mismatched oligomer (e.g. 3'-mismatch). Thus, the protein-degrading enzyme is chosen preferably such that the Km may be higher than that of the detection/elongation enzyme, if desired. Thus, the protein-degrading enzyme(s) is(are) simply included in the reaction mixture. The amount of protein-degrading enzyme to be used may be readily determined for each particular system, depending on the reactants selected, reaction conditions etc.

In a further preferred embodiment of the present method, the protein-degrading enzyme is Proteinase K (Boehringer Mannheim GmbH, Germany). An appropriate amount of Proteinase K can be determined and be added to the enzyme reaction mixture. Those of ordinary skill in the art can determine a suitable amount of protein degrading enzyme, particularly proteinase K, to degrade the enzyme in elongation/detection reactions having slow kinetics due to a mismatched oligomer, e.g. a mismatch at the 3' terminus (or 3'-1 position) of the oligomer. In the Examples appended hereto, 0.024 mg of proteinase K is utilized for every 10-15 U of Klenow polymerase.

The oligomer elongation (detection) reactions performed using the different base-specific oligomers are then compared. More particularly, in this comparison step, the rates of reaction (e.g. elongation) may be compared (e.g. the respective or relative rates). Thus, efficiencies of the oligomer detection reactions (e.g. elongation reactions) may be compared.

The respective rates, or efficiencies, of the oligomer (e.g. elongation) reactions may be determined for each of the different oligomers and compared. A greater efficiency, or higher reaction (e.g elongation) rate, is indicative of the presence of the base for which the oligomer is specific (i.e. "matched"). Thus, if a detection (i.e. base-specific) oligomer matches the template (i.e. the target base) a high reaction (e.g. elongation) rate (or efficiency) will be observed. If the oligomer is not a matched oligomer, the reaction (e.g. elongation) rate (or efficiency) will be lower. The addition of the enzyme disabling agent to the reaction mixture ensures that the non-matched oligomer is not reacted (e.g. elongated) or is reacted (e.g. elongated) with reduced or lower efficacy or at a reduced or lower rate, and thus allows discrimination between the matched and mismatched situations. In the matched oligomer situation, reaction (e.g. elongation) takes place before the enzyme disabling agent disables the enzyme. The difference in oligomer reaction (elongation) rate (or efficiency) over a matched or mismatched oligomer can be used for discrimination between bases, and thus to determine which base is present at said pre-determined position. In certain cases, depending on reaction conditions, reagents used etc., it may suffice simply to determine whether or not reaction (e.g. elongation) has taken place (i.e. the presence or absence of oligomer elongation) the presence of oligomer reaction (e.g. elongation) indicating the presence at the target (i.e. predetermined) position of the base to which the oligomer in question is matched.

Thus, the comparison step (i.e. the step of "comparing the enzymatic detection reactions") can be seen to include a step of simply determining whether or not an enzymatic detection reaction has taken place, e.g. determining whether an enzymatic detection reaction using a given base-specific detection oligomer has taken place.

In such a situation, it may suffice to use only a single base-specific detection oligomer, and determine whether or not the reaction has taken place. Thus, the comparison step may include a step of evaluating an enzymatic detection reaction using a base-specific detection oligomer, e.g. to see if it has taken place. The method of the invention may thus be performed using one or more base-specific detection-oligomers. More particularly, the method may comprise performing one or more enzymatic detection reactions using a base-specific detection oligomer, each oligomer being specific for a particular base at said predetermined position, and determining whether said enzymatic detection reaction has taken place, or comparing said enzymatic detection reactions, to determine which base is present at said position, wherein an enzyme-disabling agent is present during the enzymatic detection reaction.

The method of the invention is advantageously performed by elongating a base-specific oligomer by any suitable means. One embodiment of the invention is to hybridize a base-specific primer to the target nucleic acid and perform a primer-extension reaction.

In the present invention, primer extension can be detected or measured by any suitable means, and thus the ratio of extension using a matched primer and extension using a mismatched primer determined, by methods known in the art. If the base-specific primers are used in different reactions, PCR products may be generated and the amount of amplified DNA from each reaction can be determined.

Methods of determining or measuring primer extension include mass spectroscopy (Higgins et al. (1997) Biotechniques 23:710), luminometric assays, in which incorporation of nucleotides is monitored in real-time using an enzymatic cascade, (Nyren et al. (1997) Anal. Biochem. 244:367), or mass spectrometry or dye technology, fluorescent assays using dye-labelled nucleotides, or Pyrosequencing™ as described by Ronaghi et al. (1998) Science 281:363, and Ahmadian et al. (2000) Anal. Biochem. 280:103.

Pyrosequencing™ technology is further described in detail in WO 98/13523, WO 98/28440 and WO 00/43540 of Pyrosequencing AB and any method described therein may be used to detect or monitor or assess the primer extension reactions according to the present invention. Generally speaking, Pyrosequencing™ involves detecting nucleotide incorporation in a primer extension reaction by detecting pyrophosphate release. Thus, methods of detecting the primer extension reaction by detecting or monitoring pyrophosphate release represent one way of carrying out the comparison step of the present invention.

Pyrophosphate can be determined or detected by many different methods and a number of enzymatic methods have been described in the literature. It is preferred to use a luciferase-based (e.g. a luciferin/luciferase) light generating reaction to detect the release of pyrophosphate since the amount of light generated is substantially proportional to the amount of pyrophosphate released which, in turn, is directly proportional to the number of bases incorporated. The amount of light can readily be estimated by a suitable light sensitive device such as a luminometer. Thus, a bioluminometric assay for pyrophosphate release is preferred.

Pyrosequencing™ Technology is principally based on a method for detecting pyrophosphate release termed ELIDA and based on the enzymes ATP sulphurylase (which converts pyrophosphate and adenosine 5'-phosphosulphate (APS) to ATP and $SO^{2-}$) and luciferase (which converts ATP and luciferin in the presence of oxygen to AMP, pyrophosphate, oxyluciferin, $CO_2$ and light) (Nyrén and Lundin, Anal. Biochem., 151, 504-509, 1985).

In its preferred embodiment, Pyrosequencing™ involves the use of an ELIDA reaction performed in real-time with nucleotide incorporation (i.e. pyrophosphate is detected as it is released). This involves the use of an dATPαS analogue of the nucleotide dATP in place of dATP for incorporation (as described in detail in WO 98/13523), and preferably also the use of a nucleotide degrading enzyme to degrade unincorporated nucleotides (as described in WO 98/28440).

It has been found that the method of the invention may advantageously be performed using labelled nucleotides in the primer extension reactions to provide a convenient way of monitoring (e.g. detecting or measuring) the primer extension reactions; it may be detected whether or not incorporation has taken place by detecting the label carried on the nucleotide, or the relative or respective rates (or efficiencies) of nucleotide incorporation.

Thus, the use of labelled nucleotides represents a particularly advantageous way of detecting, and comparing, the primer extension reactions. Thus, the nucleotides used for incorporation in the primer extension reaction may carry a label, preferably a detectable label, which may be used to detect whether or not the nucleotide has been incorporated, or to follow or monitor the primer extension reaction to detect the rate or efficiency of nucleotide incorporation. Such a label may be any label giving or leading to a detectable signal (which may be directly or indirectly detectable, for example a moiety which takes part in a reaction (e.g. an enzymic or antibody-based reaction) which generates a detectable signal). Directly detectable labels are preferred, and especially labels based on dyes which may be spectrophotometrically or fluorescently detectable. Fluorescent labels are especially preferred.

Labelled nucleotides for use in sequencing are well known in the art and widely described in the literature and any of these may be used. WO 00/53812, for example, describes, inter alia, methods of sequencing based on dye-labelled (particularly fluorescently labelled) nucleotides, which may be used according to the present invention. See also U.S. Pat. No. 6,087,095.

In preferred embodiments, the label, for example the dye (e.g. fluorophore), may be attached to the nucleotide via a cleavable linker which can be cleaved to remove the label from the nucleotide when desired. Cleavage may be accomplished, for example, by chemical reaction (e.g. acid or base treatment) or by oxidation or reduction of the linkage or by light treatment, or enzymatically, depending on the nature of the linkage. Such cleavable linkages are described in detail in WO 00/53812. A preferred example is a disulphide linkage which may be cleaved by reduction, e.g. with a reducing agent such as dithiothreitol. Dyes, for example fluorophores, e.g. cyanine fluorophores (e.g. cyanine 3 or cyanine 5 fluorophores) may be conjugated via disulphide bonds to a nucleotide as described in WO 00/53812. Advantageously the label may be attached to the 3' moiety of the deoxyribose group of a nucleotide, such that cleavage and removal of the label group from the nucleotide generates a 3' OH group. Modified labelled nucleotides known as "false terminators" where a blocking group may be removed from the modified nucleotide are also described in EP-A-0745688 and U.S. Pat. No. 5,302,509.

Alternatively, the dye labelling may be performed indirectly, in which the label is not directly attached to the nucleotide at the time of "incorporation" into the elongated chain, and the dye is attached via a chemical coupling reaction performed after any enzymatic reactions. Indirect labelling requires the use of an intermediary nucleotide to which the label is attached later. Generally, the intermediary nucleotides are amine-modified NTPs (nucleotide triphosphates), such as amino allyl-dUTP/UTP. Amino allyl-dUTP contains a reactive amino group on a 2-carbon spacer attached to the methyl group on the base portion of dUTP. After incorporation into cDNA or RNA and/or use in chain elongation, the amino group may be reacted with the NHS ester of a monoreactive Cy (i.e. Cy™3 or Cy™5 Amersham Biosciences) dye. Such indirect labelling is described in Hoen et al, Nucleic Acids Research, Vol 31, No. 5, e20, 2003).

An alternative intermediary nucleotide is biotin-dUTP, which can be labelled using fluorescein-streptavidin, or digoxygenin dUTP labelled using fluorescein-anti-digoxygenin. Any suitable intermediary nucleic acid may be used that can be labelled once the chain elongation reaction has taken place.

An alternative embodiment of the invention is to hybridize a base-specific oligomer (or probe) to the target nucleic acid and elongate this oligomer via ligation to itself or another (second/further) oligomer probe. The ligation of the base specific oligomer to itself (e.g. padlock probe) or to another oligomer probe can be detected or measured by any suitable means, and thus the ratio of ligation using a matched oligomer and ligation using a mismatched oligomer determined, by methods known in the art.

Methods of determining or measuring oligomer ligation are well known, and depend upon whether a padlock probe oligomer is used (i.e. the probe ligates to itself) or whether a further probe is ligated to the base-specific oligomer. In the latter case, ligation of two oligomers (one of which is base-specific) may be detected using a variety of platforms. The ligase detection reaction as described below may be detected on a plate reader, capillary electrophoresis system, mass spectrometer, or a microchip. In the assay, the base-specific oligomer anneals to the target nucleic acid directly adjacent to the second/further oligomer resulting in the formation of a short duplex of oligomer-target containing a nick at the site of the junction between the oligomers, and this site is preferably at the allele-specific or type specific base. In the method of the invention, the base-specific oligomer that has perfect complementary (match) to the target/template will be ligated to the second/further oligomer. In the case of a base-specific oligomer which does not match (mismatch), the ligation will not be allowed to take place since the disabling agent will prevent the ligase from catalysing ligation of the mismatched oligomer by virtue of the slower reaction kinetics involved, as explained earlier. In the case of a matched base-specific oligomer, the junction between the oligomers will be covalently linked by the ligase enzyme to generate a uniquely sized ligation product. Using a method of the invention, a base mismatch at the junction together with the ligase disabling agent inhibits ligation, and thus the base-specific oligomer is not elongated. The ligase detection reaction can therefore be based on detecting the size of the oligomer by denaturing the template/oligomer duplex (e.g. via heating) and subsequently detecting the size of the oligomer via any suitable means e.g. mass spectrometry i.e. MALDI-TOF, capillary electrophoresis or gel electrophoresis.

Alternatively, tags such as barcodes may be used as the detection strategy, for example as described further below. In particular, a padlock probe containing or carrying a barcode may be used on tag (barcode)—micro arrays.

Further alternatively, one oligomer is tagged with a 'hook', i.e. with a chemical component that can be captured using a suitable partner (e.g. using biotin, a sequence tag, or any binding means). Thus the hook may be one of a pair of binding partners (e.g. affinity binding partners). Preferably it is the second/further oligomer which is provided with a 'hook'. The oligomer (not tagged with a hook) is tagged with a label, that can be detected by suitable means. Such labels are fluorescent labels, colourimetric labels, or reporter molecule such as an enzyme that can catalyze a reaction leading to a detectable signal, such as digoxygenin. The presence of digoxygenin would be detected by an alkaline-phosphatase-conjugated antibody with a chromogenic substrate. Once the oligomer-elongation (ligation) reaction has taken place, the oligomer/template duplex is contacted with the immobilized binding partner to the 'hook'—e.g. to streptavidin-coated wells, and thus the oligomer with a hook is immobilized to a solid surface, such as a well, glass slide, array or bead. The oligomer/template duplex is denatured (i.e. via heat or chemical denaturing agents) and the template and non-ligated labelled oligomers are washed away. If ligation has occurred, the labelled oligomer will be ligated to the oligomer attached to the solid support, and thus the label or reporter will be present after the washing step. If no ligation has occurred, the label or reporter will not be ligated to the oligomer attached to the solid support, and will thus be lost in the washing step. The label or reporter entity can then be detected by well known means.

The present method may be performed in a solid phase microarray format, (for example on a chip or slide or any solid support or phase used in the art for microarrays), whereby samples are reacted (e.g. elongated) in a liquid-phase format (e.g. in solution) followed by hybridization to a microarray. (By "solution" or "liquid-phase" here is meant a non-microarray format; immobilisation of the target or template sequence on a particulate support (e.g. beads) which may be dispersed or suspended in solution (or in a liquid-phase) is encompassed.) Such an embodiment is a preferred embodiment of the invention. Alternatively, the method may be performed in a microarray format in which the oligomers or samples (templates) are immobilised in the array (see FIGS. 3 to 8). Allele-specific primer extension on microarrays is known in the art and described for example by Pastinen et al. (2000) Genome Research 10:1031 and O'Meara supra et al.

Thus in addition to simple reactions (e.g. elongation reactions) where one oligomer/template is reacted (elongated) at one time, or in one given reaction (i.e. a simplex reaction), multiplex oligomer (elongation) reactions may be carried out, where a number of different (elongation) reactions (e.g. with different oligomers and/or templates (targets) are carried out simultaneously or in parallel. Most conveniently such a multiplex assay is performed in a microarray format. "Multiplex" as used herein thus means that multiple (i.e. two or more, e.g. 3, 4, 5, 6, 7, 8, 9, 10, 20, 50 or more reactions (i.e. oligomer elongation reactions) are carried out simultaneously or in parallel.

In one embodiment of the present invention wherein primer extension is performed, the immobilized oligonucleotides on the microarray are complementary to the 5'-end of the base-specific primers. Simplex or multiplex base-specific primer extensions in the presence of a polymerase disabling agent may be performed in different tubes (where two different primers are used, this would be two different tubes etc.) and the extension products can be hybridized to the immobilized oligonucleotides on different microarrays (e.g. slides), if the extension reactions are performed using nucleotides labelled with the same label (e.g. dye) in the different tubes (for example Cy5-labelled nucleotide(s)), or on one array (e.g. slide), if different (e.g. two different) labelled nucleotide(s) are used in the extension reactions (for example Cy5-labelled nucleotide(s) in one reaction and Cy3-labelled nucleotide(s) in the other reaction).

The same principle applies to oligomer elongation by ligation wherein the further/second oligomer is provided with the hook or tag and the base-specific oligomers are differentially labelled.

With regard to the primer-extension embodiment, this may readily be achieved by incorporating a tag at the 5' end of the primer, which is recognised by (or which may bind to) a corresponding or complementary tag immobilised on the array. Such a tag may conveniently be a barcode. The use of barcodes as tags has been described in the art, e.g. on the 5'-ends of type- or allele-specific primers as described by Fan et al. (2000) Genome Res. 10:853 and Hirschorn et al. (2000, PNAS, 12164-12169). By using barcodes, a liquid-phase multiplex base-specific extension of a set of SNPs (or other variant or target bases) may be performed in a single tube (if the barcodes on the matched and mismatched primers are different) or in two or more tubes (if the barcodes on the matched and mismatched primers are identical). After primer extension, the extension products can be hybridized to barcodes on the array. A modular probe as described by O'Meara et al. (1998) Anal. Biochem. 255:195 and O'Meara et al. (1998) J. Clin. Microbiol. 36:2454 may be utilized to improve the hybridization efficiency. The modular probe hybridizes to its complementary segment on the immobilized oligonucleotide and improves the hybridization of a barcode that is immediately downstream.

In the methods utilizing barcodes, it is preferred to wash excess extension primers away after primer annealing has taken place. Such a step may be achieved by immobilising the template on a said support such as magnetic beads and washing away the excess, unbound primer. Since the primers have the barcodes present it is preferable to remove the unbound primers since they can hybridise to the complementary tags on the chip/array. Since the primers cannot be extended, no labelled nucleotides can be incorporated, thus no false signals are generated if the unbound primers are retained. However, their inclusion on the array can contribute significantly to the decrease in signal intensities. Thus, removal of the unbound primers via washing leads to higher signals, and is thus desirable.

Thus the method of the invention can be performed in a liquid-phase multiplex fashion by using barcodes (FIG. 9).

In another embodiment, the immobilized oligonucleotides on the microarray are complementary to the extended product of the base-specific primers (i.e. to the "non-primer" portion of the extension reaction product) (see FIG. 10) or alternatively to the second/further oligomer in the oligomer ligation assay. Liquid-phase simplex or multiplex base-specific elongation is performed in a single tube or in separate tubes (e.g. two, three or four tubes) as discussed above. In the case of an unknown target base or where more than two alleles or mutations or other variants may occur, the method may utilize 3 or more oligomers and thus 3 or-more tubes will be required if the same labelled nucleotide is used in the elongation reactions. When single tube base-specific elongation is performed, the 5'-end of the base-specific oligomers is labelled with different dyes, for example one base-specific oligomer is 5'-end labelled with Cy5 and the other base-specific oligomer is 5'-end labelled with Cy3. In one embodiment, the primer extension is carried out with non-labelled (e.g. native) nucleotides and the extension product (the 3'-sequence of the extended primer(s)) is hybridized to the immobilized oligonucleotides on the microarray. In an alternative embodiment, oligomer elongation is carried out using non-labelled second/further oligomers and the elongation product (the base-specific oligomer ligated to the further/second oligomer) is hybridised to the immobilized oligonucleotides on the microarray. The immobilized oligonucleotides are specific for the second/further oligomer and thus non-ligated second/further oligomer may be removed from the reaction mixture prior to immobilization on the array, e.g. via washing.

In accordance with the general principles of the invention discussed above, the oligomer elongation reaction conditions are such that matched oligomers are allowed to elongate. and the "elongated" (e.g. 3'-sequence) of the matched oligomer can be hybridized and detected while mismatched oligomers do not elongate and thus lack the "elongated" or 3'-sequence that can be hybridized to the immobilized oligonucleotides on the array. The 5'-end labelling of the base-specific oligomers may be performed directly, for example the synthesized base-specific oligomer is labelled at the 5'-end, or indirectly. The direct approach may be expensive and thus, the indirect labelling is generally preferred. In the indirect labelling approach (FIG. 10) the pair of base-specific oligomers comprise a sequence tag at the 5'-end. The sequence tag between base-specific oligomers of one position differ from each other but the sequence tags for different positions are the same (meaning that only two, three or four tags are needed to be designed for all variant or target base positions. In the case of SNPs or biallelic variants where only two variant or different bases may occur only two tags will be needed). After base-specific elongation, the elongation products are mixed and hybridized to labeled and complementary oligonucleotides to the tags. The complementary oligonucleotides to the base-specific oligomer tags are labelled with different dyes. This mixture is then hybridized to the immobilized oligonucleotides on the microarray, which are complementary to the elongated products. The 3'-sequence of the matched oligomer will hybridize to the corresponding immobilized oligonucleotide on the array and will be indirectly detected through the dye-labeled oligonucleotide, which is hybridized to the tag. Mismatched oligomers do not elongate using the method of the invention and consequently lack the 3'-sequence that hybridizes to the immobilized oligonucleotides on the array.

Particularly preferred embodiments of the invention are described in Examples 3 and 4 (see particularly Example 4). The methods comprise multiplex DNA polymerase-directed extension in liquid-phase on a single-stranded DNA template or target (which preferably may be captured or immobilised on a particulate solid support (e.g. beads)) in the presence of a polymerase disabling agent, wherein the primer(s) are tagged at the 5' end with an oligonucleotide tag (e.g. a barcode tag). Following extension (matched primer) or non-extension (mismatched primer), the primer extension product is released and hybridized to a microarray by virtue of the 5' oligonucleotide tag at the end of the primer. Carrying out the primer extension reaction with labelled nucleotides permits the hybridised extension products on the array to be detected in a ready and simple manner, although as described above, other methods of labelling, including indirect labelling may also be employed.

Analogous ligation reactions may be performed using ligase, and a ligase disabling agent.

Conveniently, the target or template nucleic acid molecule (i.e. the nucleic acid molecule to be analysed or tested) is provided in single stranded form immobilised (or captured) on a solid support capable of suspension or dispersion in a liquid-phase, e.g. a particulate solid support, preferably beads and especially preferably magnetic beads.

Advantageously, the target/template nucleic acid molecule may be provided as an amplicon (i.e. a product of an in vitro amplification procedure, e.g. a PCR product), and conveniently may be immobilised through the use of an amplification primer carrying means for immobilisation, e.g. an affinity binding partner such as biotin, binding to its corresponding binding partner (in the case of biotin, streptavidin or avidin) attached to a solid support. Thus following amplification, the amplification product may be immobilised on a solid support by means of the affinity binding e.g. the biotin (incorporated via the amplification primer) binding to the streptavidin/avidin on the solid support.

The non-immobilised and complementary strand, if present, may then be removed, e.g. by elevating the temperature or via alkali elution. The captured single strands may then be used as the template/target in the primer extension reactions according to the present invention. As mentioned above, the base-specific oligomers (e.g. primers) are provided at the 5' end with unique or specific oligonucleotide sequence tags. These sequence tags are complementary to corresponding tags provided on a microarray (e.g. generic tag arrays). Multiple (i.e. two or more, e.g. 2-50, 2-40, 2-30, 2-20, or 3, 4, 5, 6, 7, 8 or 9 to 20) base-specific oligomers are added to the captured target nucleic acid molecule, and are annealed or hybridised thereto. However, it will be recognized by those skilled in the art that there is no "upper limit" for the number of entities in the array, and may be up to 10,000 or above.

After the annealing step, any excess or unbound oligomers may be removed (e.g. by washing) and enzyme catalysed oligomer elongation reactions are performed in the presence of an enzyme disabling agent. Thus, enzyme and oligomer elongation means (i.e. nucleotides or second/further oligomer) for incorporation are provided, or added to the oligomer-template mixture, in the presence of an enzyme disabling agent, as discussed above.

Advantageously, for the primer-extension embodiment, labelled nucleotides (or intermediary nucleotides which can be labelled after use) are utilized in the primer-extension reaction, and these are incorporated into the 3' end of the primer in the case of a matched-primer situation. One or more, i.e. 1, 2, 3 or 4 labelled or intermediary nucleotides may be used. The polymerase disabling agent prevents or hinders the mis-matched primer from being extended. After primer extension, the captured nucleic acid molecule may be washed to remove enzymes, disabling agent and unused labelled nucleotides.

Further, for the oligomer ligation assay, a labelled (directly or indirectly) second or further oligomer is utilized in the oligomer elongation reaction, and this is ligated to the 3' end of the base-specific oligomer in the case of a matched base-specific oligomer-primer situation. The ligase disabling agent prevents or hinders the mismatched base-specific oligomer from being elongated via ligation. After oligomer elongation, the captured nucleic acid molecule may be washed to remove enzymes, disabling agent and unused second or further oligomers.

The oligomer elongation product (i.e. extended primer or elongated oligomer) is then released, and hybridized to an array via the specific unique oligonucleotide tag at the 5' terminus. The array is then analysed for the presence of the incorporated labelled nucleotides/oligomers e.g. by scanning the array for the presence of label.

Thus, in one preferred embodiment, the invention provides a modified method of detecting a base at a predetermined position in a nucleic acid molecule, said method comprising the additional steps of using oligomers carrying an oligonucleotide tag at their 5' ends, which tags are complementary to corresponding tags provided on an array; performing said oligomer elongation reactions using labelled nucleotides or oligomers; and hybridising the products of the said oligomer elongation reactions to said array by means of the 5' oligonucleotide tags, wherein the comparison of said oligomer elongation reactions takes place (i.e. is achieved or performed) by detecting the label from said labelled nucleotides/oligomers on the array.

Thus, by detecting the presence or absence or amount of incorporated nucleotides/oligomers on the array it may be determined whether or not an oligomer elongation reaction has taken place, or which oligomers have been elongated with greater efficiency or at a higher rate.

Since each primer is base-specific, by determining whether or not a given oligomer has been elongated in the elongation reaction (i.e. by detecting the presence or absence of label) it may be determined which base is present at said predetermined (i.e. target) position. Similarly, by determining the amount of label incorporated for a given oligomer on said array it may be determined which base-specific oligomers have been elongated with greater efficiency (or at a higher rate) to determine or indicate which base is present at the target or predetermined position.

The assay format lends itself particularly well to a multiplex approach for analysing multiple different nucleic acid molecules at once. Thus, the method may be performed using multiple i.e. two or more nucleic acid molecules (e.g. 2, 3, 4, 5, 6, 7, 8, 9, 10, 12, 15, 20, 25, 30, 100, 1000, 10,000 or more nucleic acid molecules).

Advantageously, it has been found that by designing the annealing conditions in the base-specific oligomer binding step, a greater level of specificity may be achieved. Thus, by utilizing competitive oligomer annealing wherein specific oligomers for each "base-specific" position or target base (e.g. for each type) are competing for the same target site, no stringent hybridization temperatures are required. The matched and mismatched oligomers compete to hybridise to the target/template nucleic acid molecules in conditions (i.e. high temperature) in which the matched oligomers have favourable hybridisation kinetics as compared to the mismatched oligomers. The mismatched oligomers are thus out-competed. Thus, the use of competing (or competitive) oligomers represents one particularly favoured embodiment. In practice this may be achieved by selecting and/or designing the oligomers and the target template to provide competitive conditions. Thus, rather than using e.g. a pair of primers specific for each template provided (as described in Example 3 for example, in the context of multiple different templates wherein different templates having different predetermined or target positions are used together) where the primer hybridisation conditions are non-competitive because each primer pair used is designed with a specific template in mind and each template is present, a single or a restricted number of templates is (are) used (e.g. 1, 2, 3 or 4 templates) in conjunction with different base-specific primers, i.e. which are specific for different "types" or "variants" which might be present in the target template (i.e. which potentially, may be present, but not necessarily are, in the reaction mixture). This "competitive" approach is described in Example 4. By way of example, the sample template preparation (e.g. target nucleic molecule) may contain a target molecule of e.g. unknown type or containing a particular variant (e.g. mutation) to be identified. A range of possible oligomers (e.g. primers) are used, each specific for a particular type or variant (e.g. mutation) which might occur. Such oligomers will compete for binding to the template/target molecule, and the conditions are such to favour binding of the "matched" oligomer (i.e. that "corresponding" to the type or variant etc. present) This thus introduces a first level of specificity. This is then built on, by carrying out the oligomer detection (elongation) reactions using an enzyme-disabling reagent according to the present invention to further enhance the likelihood that only a matched oligomer is reacted (e.g. elongated) and hence detected. In a multiplex approach in such a "competitive" assay, a number of different templates/target molecules may be used together (e.g. from different sources or samples) with a series of different base-specific oligomers. For example such a series of oligomers may be designed with respect to particular variants or types etc. which may occur in a particular region of the template.

The first step in the annealing reaction serves as a nucleic acid denaturing step and may be performed at 50-95° C. After the nucleic acid denaturing step, the temperature is allowed to fall (either quickly or slowly but preferably slowly by simply placing the heated tube at room temperature or controlling the drop of temperature by a thermal controller) to the desired temperature (15-50° C.). Thus no precise annealing conditions are required, and in practice the solution may be heated (50-95° C.) and then cooled. However, during the second step (decreasing of temperature) the competitive hybridization occurs (as the temperature decreases and the oligomers with favourable hybridization kinetics (the completely matched oligomers) hybridize first (at a higher temperature). By occupying the target hybridization site, the matched oligomers prevent the non-specific hybridization of other (non-matched) oligomers at lower temperature.

Although such particular base-specific oligomer annealing conditions may advantageously be employed in the context of the micro-array hybridisation assay format as discussed above and in Example 4, it will be appreciated that the favourable hybridisation reaction kinetics arriving therefrom may also be applied in the context of any embodiment of the method of the invention and thus have general application. Thus, at its most general (e.g. as defined generally above) in the method of the invention, the base-specific oligomers in the oligomer elongation reactions may be bound to or annealed to the target nucleic acid molecules under competitive conditions wherein all the base-specific oligomers are competing to bind (anneal) to the same target sequence as described above.

The present invention therefore provides a reliable multiplex assay for the genotyping of individuals, such as HPV as exemplified in Example 4 herein.

The present method may also be used in a "Taq Man®" assay" also known as the 5'-nuclease assay. In the "Taq Man assay", probes that are labelled with donor-acceptor dye pairs are used. The donor-acceptor dye pairs are functioning via fluorescence resonance energy transfer (FRET) and the technique is described by Livak et al. (1995) PCR Methods Appl. 4:357. In this prior art assay, PCR is performed with a common pair of PCR primers and two allele-specific TaqMan probes. When the TaqMan probes are hybridized to the target polymorphic position, the fluorescence of the 5'-donor fluorophore is quenched by the 3'-acceptor. At the extension steps, the polymerase degrades the perfectly hybridized probes by its 5'-nuclease activity. When degraded, the 5'-donor dye of the probe dissociates from the 3'-quencher, leading to an increase of donor fluorescence. In the case of mismatched probe, the probe does not form a hybrid with the target sequence, and the fluorophores remain quenched. In the present method however, after PCR amplification, only one Taq Man probe is used, and is hybridized 1 to 20 bases downstream of the 3'-end of the base-specific primers. A base-specific extension reaction in the presence of a polymerase disabling agent with matched and mismatched (1, 2, or 3) primers to the template is performed. When the primer is matched to the template the polymerase extends the matched primer and degrades the Taq Man probe with its 5'-nuclease activity and this leads to increased donor fluorescence. However, when the primer is mismatched to the template, polymerase disabling agent inactivates or disables the polymerase before extension and the fluorescence level remains constant. Because the Taq Man probe in this assay does not hybridize to the variant (i.e. predetermined target) position but hybridizes downstream of the target position, then it only serves as a real-time detection probe and thus the genotyping is dependent on the accuracy of the base-specific extension technique.

In the method of the present invention, the elongation products may also be detected by the use of a mass spectrometer. Matched oligomers that have been elongated will have higher mass compared to mismatched oligomers that have not been allowed to elongate. In addition, the products may be distinguished by the use of double-strand-specific intercalating dye.

In another embodiment of the present invention, allele specific oligomer elongation with an enzyme disabling agent is performed using a double stranded DNA template. If double stranded DNA is generated by PCR, the excess of primers, nucleotides and other reagents must first be removed by methods known in the art such as treatment with alkaline phosphatase and exonuclease I. Two pairs of base-specific oligomers are used. One pair is complementary to the forward strand and one to the reverse strand. Base-specific elongation is performed on both strands of the double-stranded DNA. If the target base is unknown, it will be necessary to provide oligomers that cover the possibility of any one of four bases being present.

As mentioned above, in one embodiment, the present invention provides a method of detecting a mutation in a DNA molecule. In this method, the mutation is not pre-defined, as in a SNP (i.e. it is unknown) i.e. the base alteration is not known. The method utilizes enzyme catalysed oligomer elongation (or any detection reaction). Four oligomers are designed that each comprise a region that is specific for (i.e., complementary to) a target nucleic acid of interest (e.g. see FIGS. 4 to 8) or to a region of interest in a target nucleic acid, e.g. a particular stretch of nucleotides, but that differ (e.g. at the 3'-terminus) such that primer has a different nucleotide base (A, C, G or T) at a "base specific" (or "allele-specific" or "type-specific" position), for example at the 3'-terminus. As mentioned above, alternatively the "base-specific" base or different nucleotide in the oligomer may be present at another position, e.g. the 3'-1 position. The oligomers are used in separate elongation (detection) reactions of the same sample or target nucleic acid. Depending upon which base is present in the target nucleic acid at the position corresponding to the 3'-terminus of the oligomer (or any other "base-specific" position), only one of the oligomers will match the target. The elongation (detection) enzyme discriminates between a match and mismatch, and exhibits faster reaction kinetics when the base-specific base of the oligomer matches the template. Thus measurement of the difference in oligomer elongation (reaction) efficiency by the enzyme of the matched over the three mismatched oligomers allows determination of the base at the position in the target nucleic acid that corresponds to the 3'-terminus of the oligomer (or analogously, at any other "base-specific" position). Accordingly, if a previously unknown mutation is present in the target nucleic acid, the mutation is detected by virtue of one of the four oligomers "matching" the mutated target, and that oligomer exhibiting the greatest elongation (reaction) efficiency (or highest elongation (reaction) rate). Thus, the identity of the target base may be determined by determining which oligomer is elongated (reacted) (e.g. which base or second/further oligomer is incorporated) with the greatest rate or efficiency (or highest elongation (reaction) rate). In accordance with the present invention it has been found that the addition of an enzyme disabling agent in the (elongation) reaction minimizes the elongation (reaction) of mismatched oligomer configurations by disabling or inactivating the enzyme before catalysing mismatched oligomer elongation (reaction) but allows elongation (reaction) when reaction kinetics are fast, i.e., in a matched configuration, thereby reducing or eliminating false positive results.

Accordingly, when an unknown mutation is present in the target DNA sample, one of the three mismatching oligomers (that corresponds to the mutated base) will exhibit elongation (reaction). However, if the mutated sample is heterogeneous (both wild type and mutated alleles are present), both the wild type (matching) and mutated (one of the three mismatching) base-specific oligomers will be elongated (reacted) with the same efficiency (see FIG. 8). Nevertheless, if the mutation is homogeneous, only the base-specific oligomer that corresponds to the mutation will be elongated (reacted).

Samples may be prepared, primers and probes (oligomers) synthesized, and oligomer elongation (detection) reactions conducted by methods known in the art as described herein. Oligomers may be immobilized. Samples of target nucleic acids may be amplified prior to analysis, for example by PCR, including nested and multiplex PCR. Target nucleic acids may be immobilized.

In a preferred embodiment of such a mutation-detection method, each position in a target nucleic acid (or in a selected or target region) may be evaluated by using overlapping sets of oligomers (FIGS. 5 to 8). Thus, each position in a target region may be scanned for mutations using this method of the invention, simply by appropriately selecting or designing a detection oligomer such that the base at the selected "allele-specific" position in the oligomer (e.g. the 3'-terminus) corresponds to, or is complementary to the base to be scanned, i.e. the target base at the desired position. The oligomers may be spotted onto a surface to provide an array or micro array, followed by hybridization to target nucleic acid, detection reaction (e.g. elongation), measurement of reaction (e.g. elongation), and comparison of reactions (e.g. elongations).

The target nucleic acid (i.e. the target nucleic acid to be analysed or the "template" for the oligomer elongation (detection) reactions) may be any polynucleotide sequence it is desirable to obtain the target base detection or identification information about. Thus, it may be any polynucleotide, or indeed oligonucleotide sequence. The nucleic acid may be DNA or RNA, and may be natural or synthetic. Thus, the target nucleic acid may be genomic DNA, cDNA, RNA or a PCR product or other amplicon etc. The target (sample) nucleic acid may be used in any convenient form, according to techniques known in the art e.g. isolated, cloned, amplified etc., and may be prepared for the target base detection reaction, as desired, according to techniques known in the art. The target nucleic acid acts as a template for possible polymerase- or ligase-based extension or elongation of the primer/probe (oligomer) and thus may conveniently be referred to as "template" or "nucleic acid template". The DNA may also be single or double-stranded—whilst a single-stranded DNA template has traditionally been used in sequencing reactions, or indeed in any primer-extension reaction, it is possible to use a double-stranded template; strand displacement, or a localised opening-up of the two DNA strands may take place to allow primer hybridisation and enzyme (e.g. polymerase or ligase) action to occur.

As described in relation to certain particular embodiments above, in order to aid separation of a single stranded target DNA from its complementary strand, the target DNA may optionally be immobilised or provided with means for immobilisation or attachment to a solid support.

Moreover, the amount of DNA present in a sample to be analysed may be small and it may therefore be desirable to amplify the DNA prior to analysis. As mentioned above the target DNA may thus be an amplicon.

Any desired method of in vitro or in vivo amplification may be used, e.g. PCR (or a variant or modification thereof) or Self Sustained Sequence Replication (3SR) or the ligase chain reaction (LCR) etc. Whichever method of amplification is used, it may be convenient to immobilise the amplified DNA, or provide it with means for attachment to a solid support. For example, a PCR primer may be immobilised or be provided with means for attachment to a solid support.

Immobilisation of the amplified DNA may take place as part of PCR amplification itself, as where one or more primers are attached to a support, or alternatively one or more of the PCR primers may carry a functional group permitting subsequent immobilisation, e.g. a biotin or thiol group. Immobilisation by the 5' end of a primer allows the strand of DNA emanating from that primer to be attached to a solid support and have its 3' end remote from the support and available for subsequent hybridisation with the oligomer and chain elongation.

The solid support may conveniently take the form of microtitre wells. However, any solid support may conveniently be used, including any of the vast number described in the art, e.g. for separation/immobilisation reactions or solid phase assays. Thus, the support may also comprise particles (e.g. beads), fibres or capillaries made, for example, of agarose, cellulose, alginate, Teflon or polystyrene. Magnetic beads or particles, e.g. the superparamagnetic beads produced by Dynal Biotech ASA (Oslo, Norway) may be used as a suitable support.

The solid support may carry functional groups such as hydroxyl, carboxyl, aldehyde or amino groups, or other moieties such as avidin or streptavidin, for the attachment of nucleic acid molecules e.g primers. These may in general be provided by treating the support to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings.

In the primer extension reaction embodiment, any convenient polymerase enzyme may be used according to choice, e.g. T7 polymerase, Klenow or Sequenase Ver. 2.0 (USB U.S.A.). Any suitable polymerase may conveniently be used and many are known in the art and reported in the literature. In the case of a RNA template, such a polymerase enzyme may be a reverse transcriptase enzyme. However, it is known that many polymerases have a proof-reading or error checking ability and that 3' ends available for chain extension are sometimes digested by one or more nucleotides. If such digestion occurs in the method according to the invention the level of background noise increases. In order to avoid this problem, a nonproof-reading polymerase, e.g. exonuclease deficient (exo$^-$) Klenow polymerase may be used and this is preferred according to the present invention. Alternatively, substances which suppress 3' digestion by polymerase, such as fluoride ions or nucleotide monophosphates, may be used. The precise reaction conditions, concentrations of reactants etc. may readily be determined for each system according to choice. However, it may be advantageous to use an excess of polymerase over primer/template to ensure that all free 3' ends are extended.

Preferably however, the polymerase enzyme used is thermostable. Suitable thermostable polymerases include Ampli Taq DNA polymerase and Doffel fragment (truncated Taq DNA polymerase lacking 5' to 3' exonuclease activity). Performing the primer extension reaction at higher temperatures has the additional advantage that higher stringency is obtained (i.e. correct primer binding etc.).

The method of the present invention can conveniently be automated, by any suitable means, including robotic systems. One preferred system is the Magnetic Biosolution Robotic technology (Magnetrix 1200 system). Such a system can be used to handle all post-PCR procedures (e.g. immobilisation to magnetic beads, elution (separation) of non-biotinylated strand, annealing of the multiplexed extension primers by raising the temperature to 70-72° C. and then cooling to room temperature (or 20-40° C.), performing the reaction at 50-60° C., separation of products and re-use of the magnetic beads. WO 02/061428 describes a method of reversibly releasing bound biotin from a biotin-binding compound such as streptavidin (avidin). Essentially, such a method can be utilised to regenerate magnetic beads after use allowing them to be re-used.

The components and reagents for carrying out the methods of the invention may conveniently be supplied in kit form. Thus, in a further aspect, the present invention also provides a kit for use in the methods of the invention which includes at least the following components:

(a) two or more base-specific oligomers, optionally provided with 5' end oligonucleotide tags or "hooks";

(b) an enzyme disabling agent;

(c) optionally, an enzyme which catalyses oligomer elongation;

(d) optionally one or more nucleotides for incorporation, preferably labelled nucleotides;

(e) optionally a second oligomer for incorporation, preferably a labelled second oligomer;

(f) optionally means for comparing said oligomer elongation reactions.

The means for comparing said oligomer elongation reaction when said reactions are primer extension reactions may comprise the reagents and/or apparatus appropriate for the selected primer extension reaction detection modality (i.e. means for detecting the primer extension reactions). Such means may comprise for example, means for bioluminometric detection of primer extension (e.g. the ELIDA enzymes, ATP sulphurylase and luciferase, optionally with a nucleotide-degrading enzyme (e.g. apyrase) and/or one or more α-thio-modified nucleotides (e.g. dATPαS) for carrying out Pyrosequencing™ Technology), or a generic-tag array (i.e. an array carrying tags complementary to the 5' tags carried by the base-specific primers), a Taq man probe etc.

Other possible components may include reagents and/or detection by mass spectrometry, for example by MALDI-TOF.

As mentioned above, the specific base-detection methods of the present invention find utility in a number of areas, including allele-specific assays, SNP detection and analysis, mutation detection and screening and genotyping as previously discussed.

Methods of genotyping are useful not only in basic research and analysis, characterisation and identification of individuals etc., but also in many clinical applications. This is particularly so in the area of microbial identification and characterisation, for example for diagnostic applications.

For a diagnostic purpose, it is frequently desirable to be able to detect or determine not only the species or genus of a given pathogen or infecting microorganism (e.g. bacteria or virus) but also its particular genotype (e.g. type or strain). Many viruses, for example, are known to occur with multiple genotypes (e.g. HPV as discussed in detail in Example 4 below). In many cases, particular genotypes may be associated with higher virulence or risk (e.g. in viruses associated with the development of particular pathologies (as in the case, for example, of HPV and cervical cancer). It is thus important in such cases to be able to determine what particular microbial strain or genotype is present. Such genotype analysis of clinical samples may thus be of importance also in epidemiological studies etc.

The present invention provides methods of genotyping (and other forms of mutation or variant-base analysis) which are extremely accurate, cost effective and robust. Advantageously, the methods may also be presented in formats which are readily automated and suitable for high throughput multiplex analysis.

BRIEF DESCRIPTION OF THE DRAWINGS

The present invention is exemplified by the following non-limiting Examples and Figures, the figures depicting:

FIG. 6A shows the pattern of spotted allele-specific primers for codons 12 and 13 (exon 1) (upper square) and codon 61 (exon 2) (lower square) of the N-ras gene. For each base position, one matched 3'-terminus (first spot) and three mismatched 3'-terminus (the spots underneath) are spotted on the microarray chip. FIG. 6B shows the ASE assay on the chip. As shown some of the 3'-terminus mismatched primers to the target template exhibit such high non-specific extension that the typing is incorrect. FIG. 6C shows that inclusion of a DNA disabling agent, e.g. a protein digesting enzyme (such as Proteinase K) in the allele-specific extension reactions circumvents the problems associated with ASE and acquires correct results.

FIG. 7A shows the pattern of spotted allele-specific primers for a selected region of exon 5 of the p53 gene. FIGS. 7B and 7C compares the ASE and present invention assays. As shown in 7B (the ASE assay), some of the 3'-terminus mismatched primers give rise to non-specific extensions while these problems do not appear in the assay of the invention.

FIG. 11A shows the pattern of spotted tags on the microarray chip. Each tag on the chip has a complementary sequence to a tag on an allele-specific primer. A pair of allele-specific primers is used, thus two tags on the microarray chip are devoted to analysis of one SNP (one tag for allele-specific primer 1 (P1) and one tag for allele-specific primer 2 (P2)). SNPs 1-13 correspond to SNPs 24 (G/A), 155 (A/G), 2384 (G/A), 5175 (G/A), 3288 (G/A), TSC0140687 (T/C), TSC0105540 (G/A), TSC0139938 (T/C), TSC0009926 (G/A), TSC0110127 (G/A), TSC0100056 (T/C), TSC0125096 (T/C) and TSC0105206 (T/C) respectively (the bases indicated for each SNP are the bases on the 3'-terminus of the allele-specific primers and the first base here corresponds to P1 (primer 1) and the second base corresponds to P2 (primer 2)). FIG. 11B shows the microarray raw-data results for conventional ASE for samples 13 and 36. FIG. 11C shows the microarray raw-data results obtained from the assay of the present invention performed on the same samples. Notice that in these two samples, the PCR for SNP 6 has failed.

FIG. 14, Part 1-3—Simulation of results obtained by the method depicted in FIG. 13.

FIG. 15 shows three MCTSH-PrASE genotyping examples for typing of HPV 16, 18 and 33. The results show the possibility of typing multiple HPV infections. PCR products of 4 different HPV plasmids were mixed and genotyped without the need for optimization or modification.

EXAMPLES

Example 1

Figure 1:
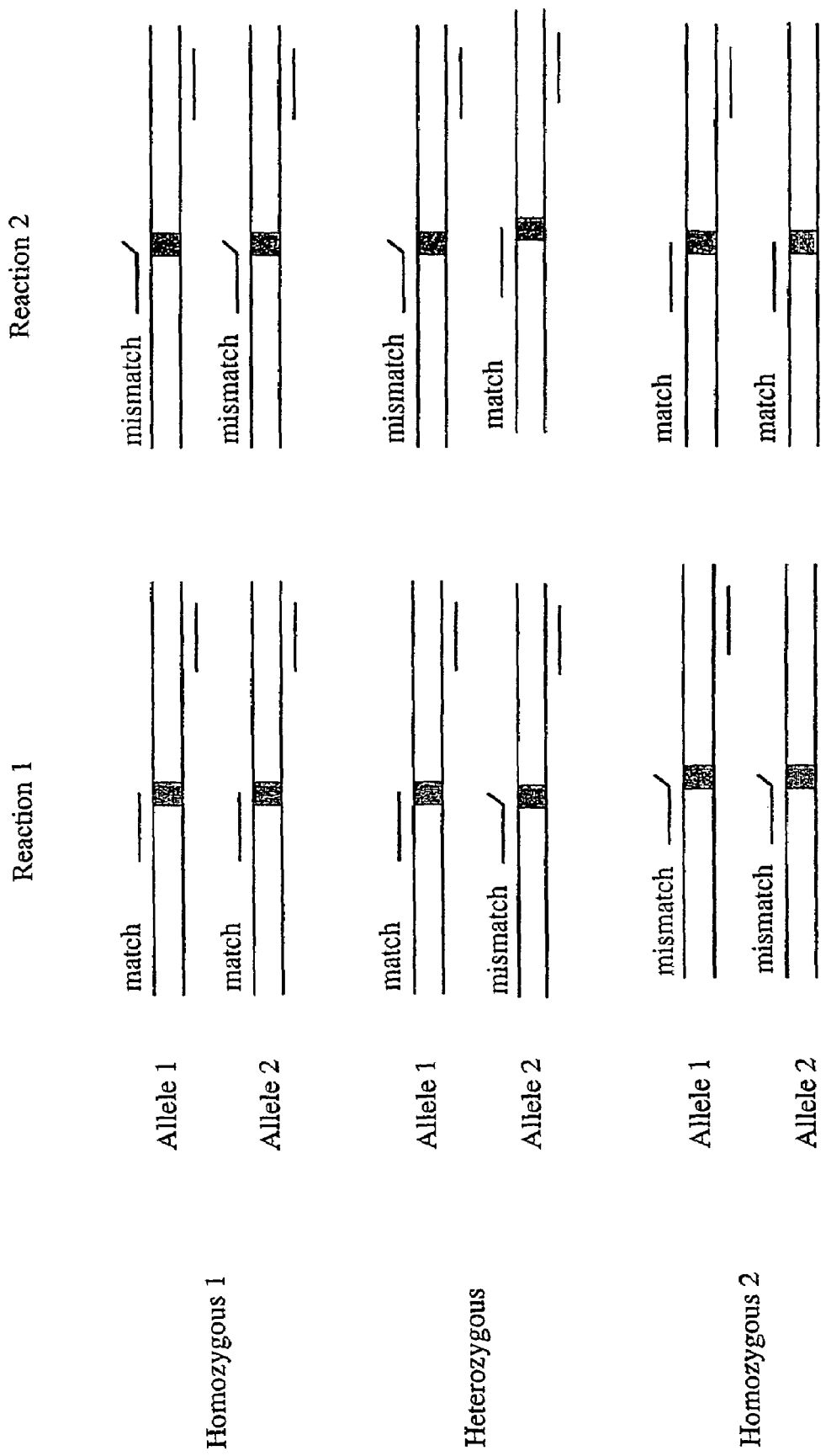
FIG. 1—The principle of base-specific extension. A sample is divided into two extension reactions that consist of exactly same reagents with one exception, the 3'-end of one of the primers. Each primer is designed to match one allele perfectly but mismatch the other allele at the 3'-end. In this way, each allele-specific extension reaction provides information about the presence or absence of one allele. In the case of homozygous DNA, one extension reaction results in detectable product while poor amplification of the other reaction is obtained due to 3'-end mismatch between the primer and the target DNA. A heterozygous sample ends up with equal extension in both reactions because half of the target template is perfectly complementary to the allele-specific primer in each reaction.
Figure 2:
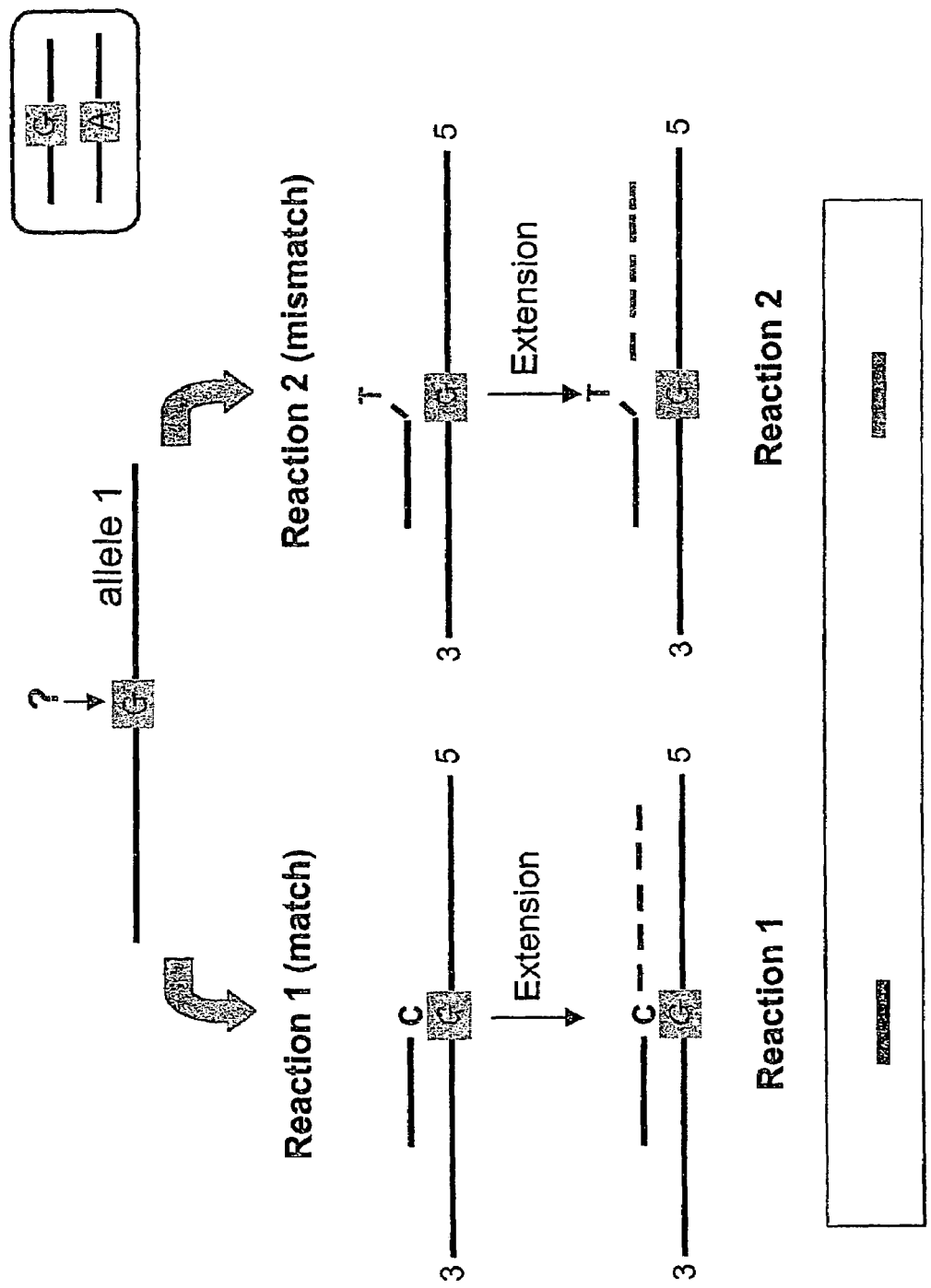
FIG. 2—Problems associated with current type- or allele-specific extension assays. The poor discrimination property of the DNA polymerases leads to extension of some primer/template mismatches such as G/T and A/C, giving rise to false positive results.
Figure 3:
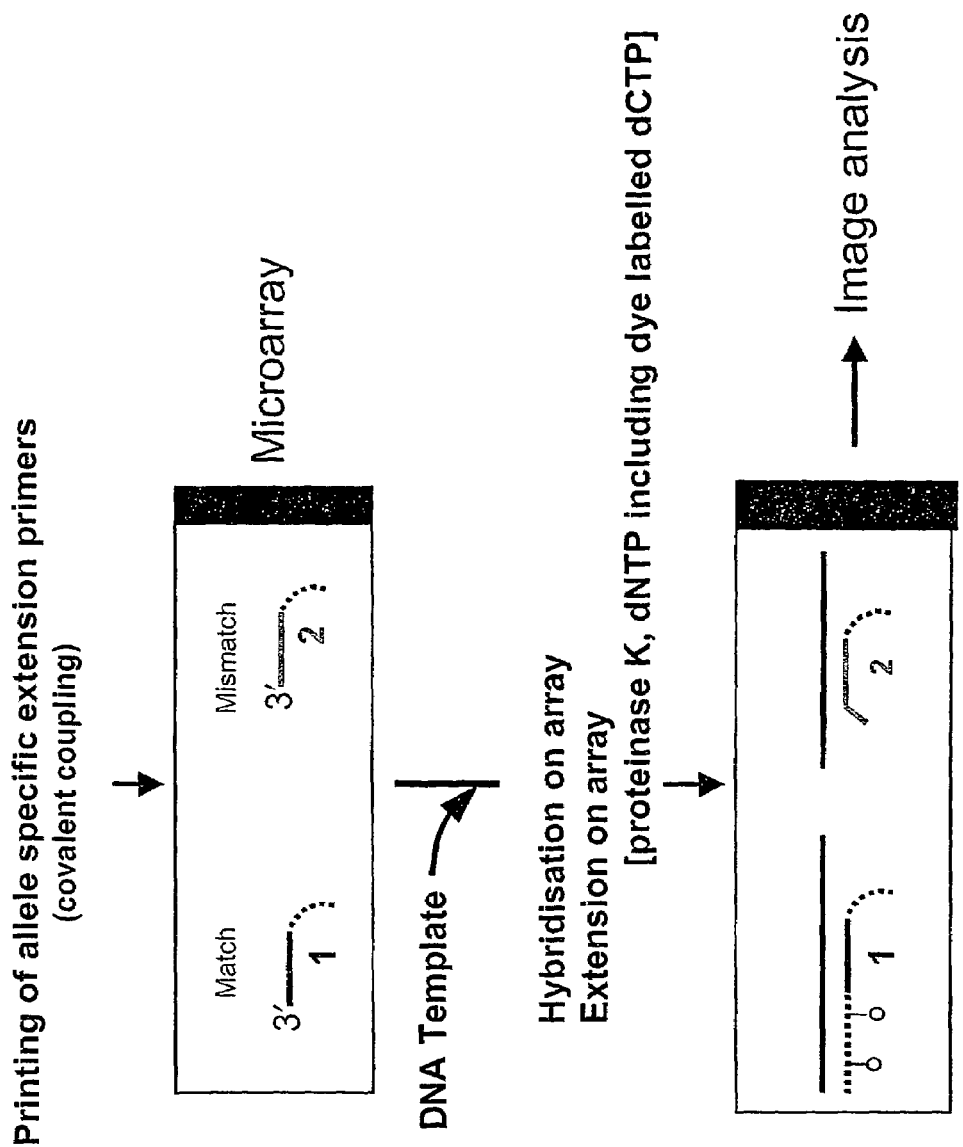
FIG. 3—Schematic illustration of the method of the invention on an oligonucleotide microarray. DNA is hybridized to a microarray of allele-specific or type-specific extension primers whose 3'-terminus is positioned at the variable locus, which in this case is an SNP. Hybridization of homogeneous template generates a perfectly matched and 3'-terminus mismatched duplexes, which are then subjected to extension with labelled nucleotide(s). In the presence of a DNA disabling agent, herein a protein-degrading enzyme, extension of the mismatched primer-template is prevented resulting in the variable site being correctly genotyped.
Figure 4:
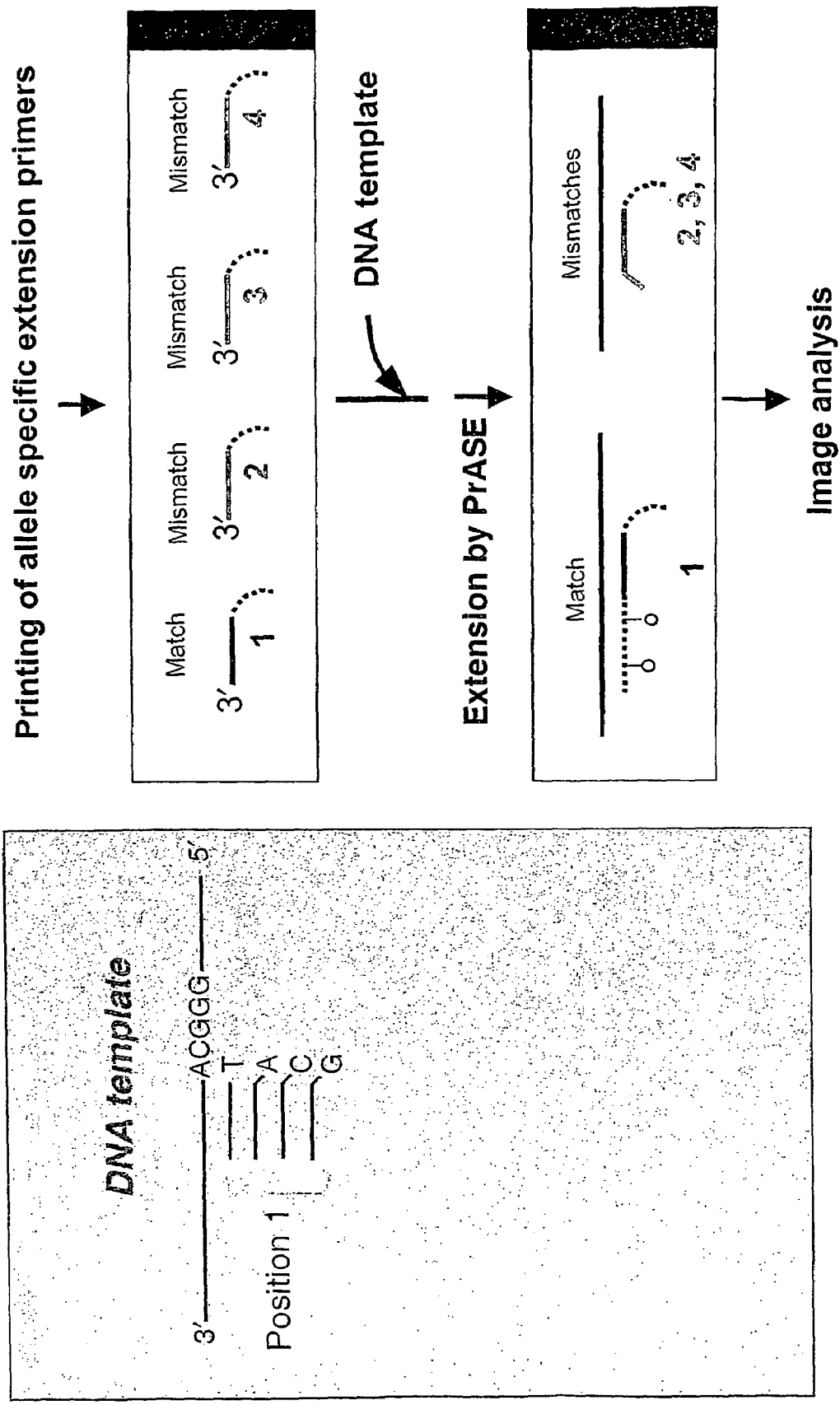
FIG. 4—Schematic illustration of the method of the present invention for detection of variable bases. DNA is hybridized to a microarray of four base-specific extension primers whose 3'-terminus have different nucleotide base (A, C, G, and T) at the base specific position. In the case of wild type sequence, depending upon which base is present in the target nucleic acid (base A here), only one of the primers will match the target (the primer with T here). When extension is performed in the presence of a polymerase disabling agent, only this primer will be extended. When an unknown variable base is present in the target DNA, one of the three 3'-terminus mismatching primers (corresponding to the variable base) will exhibit extension.
Figure 5:
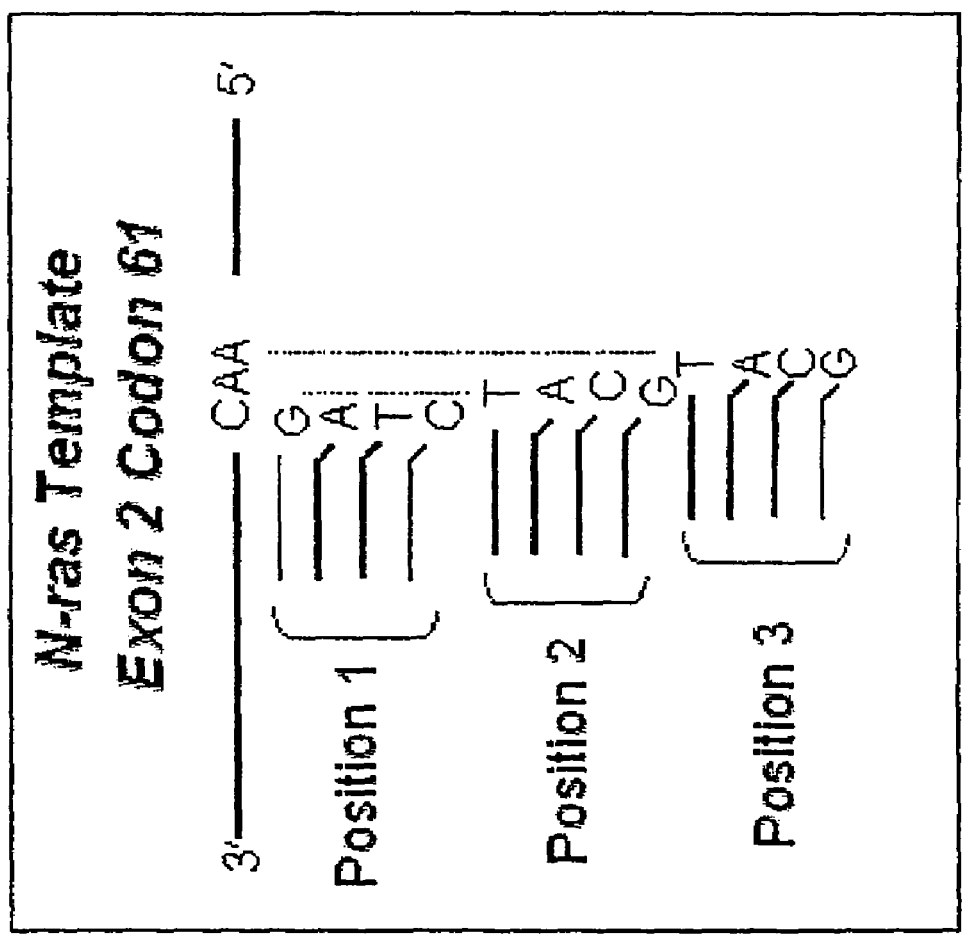
FIG. 5—An overlapping set of extension primers may be used to sequence a target template and to identify all possible unknown mutations. In this example, codon 61 of the N-ras gene is shown.

Proteinase-Mediated Allele-Specific Primer Extension (PrASE) on DNA Microarrays

Sequencing and Mutation Detection of the N-ras Gene

A single step genotyping method has been developed to determine genetic variations (mutations) in two hot spot mutation regions in the N-ras gene. The specificity of DNA polymerase in allele specific extension can be enhanced by temporal limitation of the reaction with Proteinase K. These results demonstrate the utility of proteinase-mediated allele-specific extension ("PrASE") as a method suitable for high throughput re-sequencing and mutation detection in oncogenes. In the experimental setup, primers complementary to codons 12-13 and codon 61 of the N-ras gene were spotted onto a solid phase. The primers (sense and anti-sense) were designed so that complementary primers for all four genotypes in the nine base positions were present. The extension reaction was performed in a single step following hybridization of target DNA sequences to the immobilized primers on the array surface.

Materials and Methods

Templates

In order to evaluate the PrASE technology, oligonucleotides with the same sequence composition as exon 1 and exon 2 of the N-ras gene were designed to be used as template. These oligonucleotides were as follow:

```
Forward-exon1-wt

TGACTGAGTACAAACTGGTGGTGGTTGGAGCA GGTGGTGTTGGGAAAAGCGCACTGACAA and

Forward-exon2-wt

CTGTTTGTTGGACATACTGGATACAGCTGGACAAGAAGAGTACAGTGCCATGAGAG
```

In the above sequences, the underlined bases correspond to the wild type sequence of codons 12 and 13 (in exon 1) and codon 61 (in exon 2) of the N-ras gene. An oligonucleotide with a sequence corresponding a mutated base was designed as follow:

Forward-exon1-mutation-in-position1-G/T

TGACTGAGTACAAACTGGTGGTGGTTGGAGCA TGTGGTGTTGGGAAAAGCGCACTGACAA

The underlined bases correspond to codons 12 and 13 of the N-ras gene and the base indicated in italics (base T) is a substitution for the wild type (base G).

Primers and Microarray Design

The position discriminating primers were synthesized with a 5' amino modification to allow for immobilization. Each primer had a 5'-terminus comprising a 15 poly-T sequence (serving as spacer). The primers were designed to have a Tm (melting temperature) within 52-54° C. to the template.

20 µM solutions of the 72 different oligonucleotides (see Table 1) were spotted on Motorola slides (Motorola life sciences, Ill., USA) using a GMS 417 arrayer (Affymetrix, USA) and immobilized according to the manufacturers instructions. 0.06% sarkosyl detergent was added to improve spot uniformity. The primers were printed in 16 clusters on the microscope slide each cluster containing one of each primer, and each primer was duplicated, making a total of 144 spots. The distance between the spots were 250 µM and the spot diameter approximately 200 µM. The 16 clusters were positioned in two columns of eight rows each with a 9 mm distance between cluster centres. The primers were synthesized by MWG-biotech, Germany.

TABLE 1

List of the allele-specific primers spotted on the microarray

5'->3'

Exon 1 Forward Primers

FRasE1K12P1G  TTTTTTTTTTTTTTTCTGGTGGTGGTTGGAGCAG
FRasE1K12P1A  TTTTTTTTTTTTTTTCTGGTGGTGGTTGGAGCAA
FRasE1K12P1C  TTTTTTTTTTTTTTTCTGGTGGTGGTTGGAGCAC
FRasE1K12P1T  TTTTTTTTTTTTTTTCTGGTGGTGGTTGGAGCAT

FRasE1K12P2G  TTTTTTTTTTTTTTTGGTGGTGGTTGGAGCAGG
FRasE1K12P2A  TTTTTTTTTTTTTTTGGTGGTGGTTGGAGCAGA
FRasE1K12P2C  TTTTTTTTTTTTTTTGGTGGTGGTTGGAGCAGC
FRasE1K12P2T  TTTTTTTTTTTTTTTGGTGGTGGTTGGAGCAGT

FRasE1K12P3T  TTTTTTTTTTTTTTGGTGGTGGTTGGAGCAGGT
FRasE1K12P3A  TTTTTTTTTTTTTTGGTGGTGGTTGGAGCAGGA
FRasE1K12P3C  TTTTTTTTTTTTTTGGTGGTGGTTGGAGCAGGC
FRasE1K12P3G  TTTTTTTTTTTTTTGGTGGTGGTTGGAGCAGGG

FRasE1K13P1G  TTTTTTTTTTTTTTGTGGTGGTTGGAGCAGGTG
FRasE1K13P1A  TTTTTTTTTTTTTTGTGGTGGTTGGAGCAGGTA
FRasE1K13P1C  TTTTTTTTTTTTTTGTGGTGGTTGGAGCAGGTC
FRasE1K13P1T  TTTTTTTTTTTTTTGTGGTGGTTGGAGCAGGTT

FRasE1K13P2G  TTTTTTTTTTTTTTTGGTGGTTGGAGCAGGTGG
FRasE1K13P2A  TTTTTTTTTTTTTTTGGTGGTTGGAGCAGGTGA
FRasE1K13P2C  TTTTTTTTTTTTTTTGGTGGTTGGAGCAGGTGC
FRasE1K13P2T  TTTTTTTTTTTTTTTGGTGGTTGGAGCAGGTGT

FRasE1K13P3T  TTTTTTTTTTTTTTTGGTGGTGGAGCAGGTGGT
FRasE1K13P3A  TTTTTTTTTTTTTTTGGTGGTGGAGCAGGTGGA
FRasE1K13P3C  TTTTTTTTTTTTTTTGGTGGTGGAGCAGGTGGC
FRasE1K13P3G  TTTTTTTTTTTTTTTGGTGGTGGAGCAGGTGGG

TABLE 1-continued

List of the allele-specific primers spotted on the microarray

5'->3'

Exon 1 Reverse primers

RRasE1K12P1C  TTTTTTTTTTTTTTT CGCTTTTCCCAACACCACC
RRasE1K12P1A  TTTTTTTTTTTTTTT CGCTTTTCCCAACACCACA
RRasE1K12P1G  TTTTTTTTTTTTTTT CGCTTTTCCCAACACCACG
RRasE1K12P1T  TTTTTTTTTTTTTTT CGCTTTTCCCAACACCACT

RRasE1K12P2C  TTTTTTTTTTTTTTTG CGCTTTTCCCAACACCAC
RRasE1K12P2A  TTTTTTTTTTTTTTTG CGCTTTTCCCAACACCAA
RRasE1K12P2G  TTTTTTTTTTTTTTTG CGCTTTTCCCAACACCAG
RRasE1K12P2T  TTTTTTTTTTTTTTTG CGCTTTTCCCAACACCAT

RRasE1K12P3A  TTTTTTTTTTTTTTTTG CGCTTTTCCCAACACCA
RRasE1K12P3C  TTTTTTTTTTTTTTTTG CGCTTTTCCCAACACCC
RRasE1K12P3G  TTTTTTTTTTTTTTTTG CGCTTTTCCCAACACCG
RRasE1K12P3T  TTTTTTTTTTTTTTTTG CGCTTTTCCCAACACCT

RRasE1K13P1C  TTTTTTTTTTTTTTGTG CGCTTTTCCCAACACC
RRasE1K13P1A  TTTTTTTTTTTTTTGTG CGCTTTTCCCAACACA
RRasE1K13P1G  TTTTTTTTTTTTTTGTG CGCTTTTCCCAACACG
RRasE1K13P1T  TTTTTTTTTTTTTTGTG CGCTTTTCCCAACACT

RRasE1K13P2C  TTTTTTTTTTTTTAGTG CGCTTTTCCCAACAC
RRasE1K13P2A  TTTTTTTTTTTTTAGTG CGCTTTTCCCAACAA
RRasE1K13P2G  TTTTTTTTTTTTTAGTG CGCTTTTCCCAACAG
RRasE1K13P2T  TTTTTTTTTTTTTAGTG CGCTTTTCCCAACAT

RRasE1K13P3A  TTTTTTTTTTTTTTCAGTG CGCTTTTCCCAACA
RRasE1K13P3C  TTTTTTTTTTTTTTCAGTG CGCTTTTCCCAACC
RRasE1K13P3G  TTTTTTTTTTTTTTCAGTG CGCTTTTCCCAACG
RRasE1K13P3T  TTTTTTTTTTTTTTCAGTG CGCTTTTCCCAACT

Exon 2 Forward Primers

FRasE2K61P1C  TTTTTTTTTTTTTTTCATACTGGATACAGCTGGAC
FRasE2K61P1A  TTTTTTTTTTTTTTTCATACTGGATACAGCTGGAA
FRasE2K61P1G  TTTTTTTTTTTTTTTCATACTGGATACAGCTGGAG
FRasE2K61P1T  TTTTTTTTTTTTTTTCATACTGGATACAGCTGGAT

FRasE2K61P2A  TTTTTTTTTTTTTTTATACTGGATACAGCTGGACA
FRasE2K61P2C  TTTTTTTTTTTTTTTATACTGGATACAGCTGGACC
FRasE2K61P2G  TTTTTTTTTTTTTTTATACTGGATACAGCTGGACG
FRasE2K61P2T  TTTTTTTTTTTTTTTATACTGGATACAGCTGGACT

FRasE2K61P3A  TTTTTTTTTTTTTTTTACTGGATACAGCTGGACAA
FRasE2K61P3C  TTTTTTTTTTTTTTTTACTGGATACAGCTGGACAC
FRasE2K61P3G  TTTTTTTTTTTTTTTTACTGGATACAGCTGGACAG
FRasE2K61P3T  TTTTTTTTTTTTTTTTACTGGATACAGCTGGACAT

Exon 2 Reverse primers

RRasE2K61P1G  TTTTTTTTTTTTTTT CATGGCACTGTACTCTTCTTG
RRasE2K61P1A  TTTTTTTTTTTTTTT CATGGCACTGTACTCTTCTTA
RRasE2K61P1C  TTTTTTTTTTTTTTT CATGGCACTGTACTCTTCTTC
RRasE2K61P1T  TTTTTTTTTTTTTTT CATGGCACTGTACTCTTCTTT

RRasE2K61P2T  TTTTTTTTTTTTTTT CATGGCACTGTACTCTTCTT
RRasE2K61P2A  TTTTTTTTTTTTTTT CATGGCACTGTACTCTTCTA
RRasE2K61P2C  TTTTTTTTTTTTTTT CATGGCACTGTACTCTTCTC
RRasE2K61P2G  TTTTTTTTTTTTTTT CATGGCACTGTACTCTTCTG

TABLE 1-continued

List of the allele-specific primers spotted on the microarray

5'->3'

RRasE2K61P3T  TTTTTTTTTTTTTTCT CATGGCACTGTACTCTTCT
RRasE2K61P3A  TTTTTTTTTTTTTTCT CATGGCACTGTACTCTTCA
RRasE2K61P3C  TTTTTTTTTTTTTTCT CATGGCACTGTACTCTTCC
RRasE2K61P3G  TTTTTTTTTTTTTTCT CATGGCACTGTACTCTTCG

Spatial Separation of Samples

The 16 clusters on the microarray slide were separated during hybridization and extension using a silicone mask (Elastosile 601 A/B Wacker Chemie GmbH, Munich, Germany) molded in a 96 well plate and excised to fit the slide. A Custom made rack was used to press the silicone firmly to the slide and keep it in place during the reactions.

Hybridization

Five pmol of synthetic oligonucleotides were hybridized in 5×SSC 0.2% SDS and 0.5 µg single strand binding protein (SSB) (in house produced) for about one hour in a final volume of 60 µl/well. The slides were washed in 2×SSC 0.1% SDS at 50° C. for 10 min and then rinsed in 0.1×SSC and dried by a modified table centrifuge.

Extension

The extension reaction was prepared so that a pre-heated (65° C.) mixture (50 µl) of Proteinase K and dNTP's was included to a well containing a mixture (10 µl) of Klenow fragment (room temperature). The final extension mixture contained 8 U Klenow (in house produced), 0.5 µM dNTP (50% Cy5 labeled dCTP) (Amersham Pharmacia Biotech), 0.25% BSA, 1 mM DTT, 5 mM $MgCl_2$ and 24 µg of Proteinase K (Boehringer Mannheim GmbH, Germany) with a final volume of 60 µl/well. When conventional allele-specific primer extension was performed, a 60 µl extension mixture was prepared and added to the well. This extension mixture comprised of 8 U Klenow (in house produced), 0.5 µM dNTP (50% Cy5 labeled dCTP) (Amersham Pharmacia Biotech), 0.25% BSA, 1 mM DTT and 5 mM $MgCl_2$ and the reaction was carried on at 37° C. After extension reaction, the slide was washed in 2×SSC 0.1% SDS at 50° C. for 10 min and then rinsed in first 0.2×SSC followed by 0.1×SSC and dried by centrifugation on a modified table centrifuge.

Data Acquisition

Following the extension data was obtained by scanning slides with a GMS 428 scanner (Affymetrix, USA). Data was extracted into a TIFF file and analyzed in GenePix 4.0, (Axon instruments, USA). All spots were manually inspected prior to data extraction.

Results and Discussions

The genome is located in the nucleus of the eukaryotic cell in two copies, one maternal and one paternal. Normally all somatic cells contain exactly the same genetic material. In pathological conditions such as cancer divergence often occurs. Genetic alterations in tumor suppressor genes and oncogenes are very frequent in cancer and interfere with signal cascades regulating apoptosis and mitosis. The types of genetic alterations vary between cancers but are almost always present. The form of genetic alterations can vary from gross translocations to single nucleotide mutations, deletions or insertions. Gross genetic alterations such as chromosomal translocations or duplications can be detected by cytogenetics, however for more subtle alterations other methods are required. Efforts are made to isolate prognostic mutations i.e. mutations which are associated with the development of a specific pathological phenotype e.g. malignancy and metastases. Prognostic mutations can then be used as indications for medical treatment and patient status.

Individuals can differ from each other genetically by large repeat-associated polymorphisms, and variations due to replication errors. Large repeat-associated polymorphisms occur due to intra-chromosomal duplication. Variation due to replication errors includes short tandem repeats, where especially micro satellites are highly polymorphic, and single nucleotide polymorphisms (SNPs). Microsatellites are believed to expand and contract due to replication slippage or un-equal crossing over. SNPs are mutations where one nucleotide has been replaced by another nucleotide. According to the definition each allele must be present in more then 1% of the population. Variants present in less then 1% are referred to as mutations or variants of the locus. The SNP is the dominant variation within the human genome. The distribution of SNPs varies non-randomly in the genomic sequence and the frequency tends to be lowest in coding sequences and highest in non-coding sequences.

The objective of these examples is to demonstrate the Proteinase-Mediated Allele-Specific Primer Extension (PrASE) protocol of the present invention is a robust and accurate method for re-sequencing and genotype determination. We have chosen the N-ras gene as a model gene for examination of hot spot regions. The screened N-ras gene positions have been demonstrated to display high frequency of mutations in cutaneous melanoma. Elucidating the mechanisms behind the melanoma is a highly relevant quest because the incidence of melanoma is increasing worldwide. The key factors influencing Melanomas are genetic predisposition and exposure to sunlight. The proto-oncogene N-ras belong to the GTP-binding G-proteins, and have a key role in intracellular signaling and signal transduction. We have investigated two regions in the N-ras gene, one region containing codons 12 and 13 (exon 1) and another containing codon 61 (exon 2). The investigation of hot spot regions reduce the amount of amplified genomic fragments compared to SNP analysis but is based on the exact same methodology.

Figure 6:
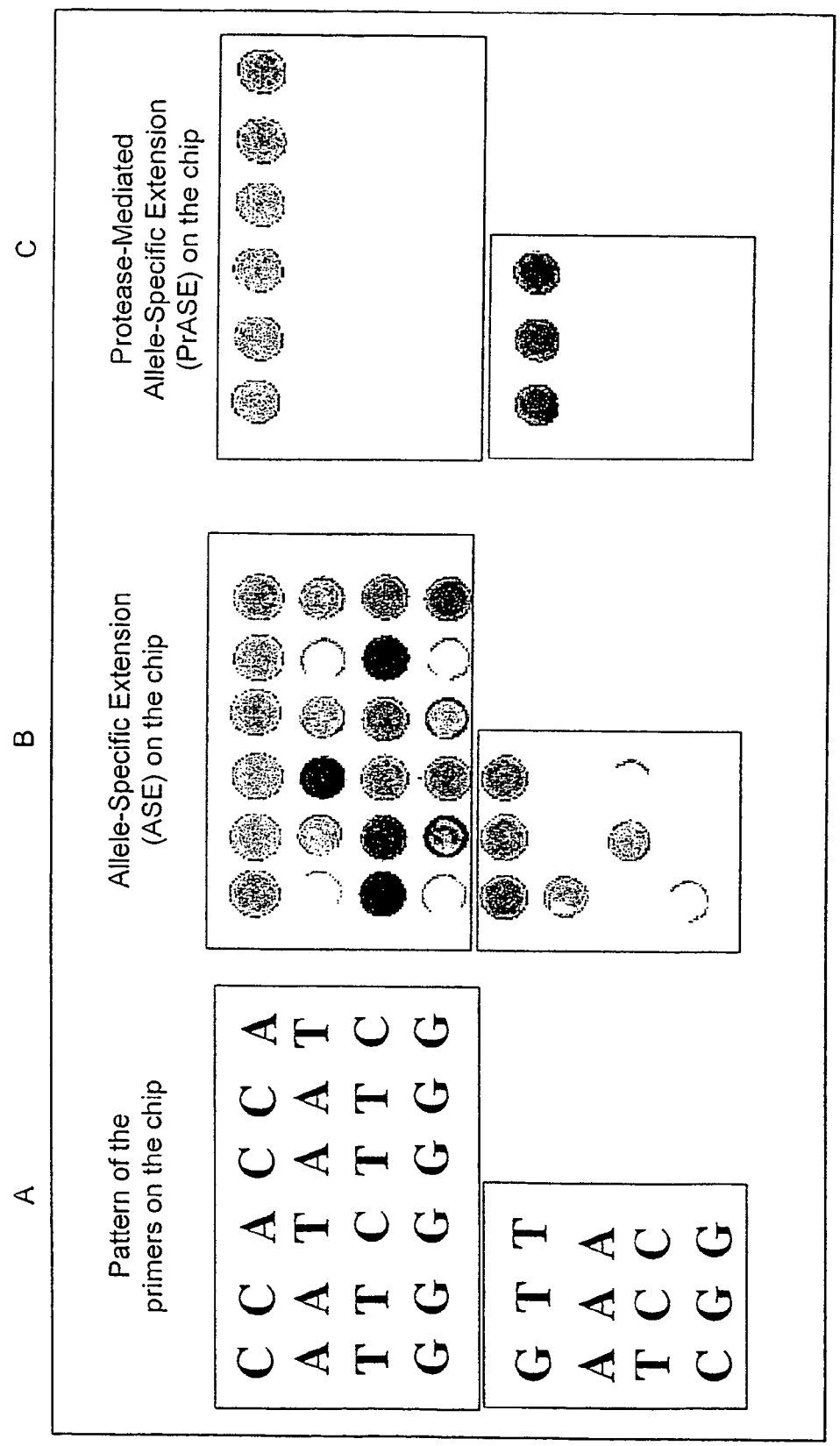
FIG. 6—Comparison of conventional Allele-Specific Extension (ASE) assays to the assay of the present invention using the N-ras gene.

In the experimental setup, conventional Allele-Specific Primer Extension (ASE) was compared to Proteinase-Mediated Allele-Specific Primer Extension (PrASE). As shown in FIG. 6B (in which ASE has been performed) some of the mismatched primer template duplexes exhibit such high extension rates that the typing results generated are incorrect. Examples of such incorrect mismatched primer/template extensions (3'-terminus mismatched primer to template) are T to G, C to T and G to T. FIG. 6C shows that inclusion of the thermo-stable protein digesting (degrading) enzyme, Proteinase K, in the allele-specific extension reactions avoids the problems associated with ASE and the correct results are obtained. Table 2 shows a summary of results (match to mismatch ratios) obtained with ASE and PrASE. In Table 2, the first column shows the name of allele-specific oligonucleotides (spotted on the microarry) and the following column shows the sequence of these allele-specific oligonucleotides. For each base position, one oligonucleotide is 3'-matched (i.e. is complementary to) the target template (always the first oligonucleotide) and three oligonucleotides are 3'-mismatched (i.e. one base mismatched) (the three oligonucleotides beneath the first one) to the target template. There are nine base positions corresponding to the three investigated codons in the N-ras gene and thus in Table 2 the allele-specific oligonucleotides for each base position are clustered. The third column in Table 2 shows the ratios of results obtained from the ASE assay: matched (signal that was obtained from the first oliginucleotide) to mismatched (signal obtained from the other oligonucleotides). The ratio for the matched signal to each of the mismatched signals is indicated in the same row as the mismatched oligonucleotide. For example, in the first allele-specific oligonucleotide cluster, the target template has base G in the position of interest and therefore the first oligonucleotide will be perfectly matched (base C in the 3'-terminus), thus giving high levels of signal (obtained from the labelled and incorporated nucleotide). However, the second oligonucleotide in this cluster has an A at the 3'-terminus which is mismatched to base G in target template and therefore gives a low signal. The ratio of matched signal to mismatched signal in this example is 31 and is indicated in the same row as the mismatched oligonucleotide with the base A in the 3'-terminus. In a previous study we performed a statistical calculation (A. Ahmadian et al, 2001, Nucleic Acids Research, e121, supra) and concluded that ratios equal or below 2 are definitely heterozygous, and for an allelic sample to be considered as homozygous this ratio has to be more than 4. As shown in the ASE column (ratios for the ASE assay), some of the ratios are incorrect and indicate a heterozygous (mutated) target DNA template when the target DNA template was homozygous (wild type sequence). Examples of these poor results (which are due to high extension signals from the mismatched primer hybridized to template) are the ratios: 1.6 (C to T mismatch), 2.2 (G to T mismatch), 2.1 (T to G mismatch), 1.4 (C to T mismatch) and 2.3 (G to T mismatch). However, when the method of the invention, particularly PrASE, was performed, the PrASE ratios (see PrASE column in Table 2) were higher than the ASE ratios. In the PrASE assay, the low ratios that were obtained by the ASE assay, became 32, 33, 130, 40 and 63, respectively when performed with PrASE. Thus, in cases where low ratios are obtained by the ASE assay, at least 15 fold greater match to mismatch ratio is achieved by the PrASE assay. The last column in Table 2 shows that without exception, greater match to mismatch ratios are obtained by the PrASE assay. The ratio data presented in Table 2 is result of mean value of four replicates for each spot.

TABLE 2

|  |  | ASE | PrASE | PrASE/ASE |
|---|---|---|---|---|
| Exon 1 Reverse |  |  |  |  |
| RRasE1K12P1C | $(T)_{15}$ CGCTTTTCCCAACACCACC |  |  |  |
| RRasE1K12P1A | $(T)_{15}$ CGCTTTTCCCAACACCACA | 31 | 77 | 2.48 |
| RRasE1K12P1T | $(T)_{15}$ CGCTTTTCCCAACACCACT | 4.8 | 95 | 19.79 |
| RRasE1K12P1G | $(T)_{15}$ CGCTTTTCCCAACACCACG | 25 | 89 | 3.56 |
| RRasE1K12P2C | $(T)_{15}$ GCGCTTTTCCCAACACCAC |  |  |  |
| RRasE1K12P2A | $(T)_{15}$ GCGCTTTTCCCAACACCAA | 19 | 58 | 3.05 |
| RRasE1K12P2T | $(T)_{15}$ GCGCTTTTCCCAACACCAT | 4 | 116 | 29 |
| RRasE1K12P2G | $(T)_{15}$ GCGCTTTTCCCAACACCAG | 12.5 | 41 | 3.28 |
| RRasE1K12P3A | $(T)_{15}$ TGCGCTTTTCCCAACACCA |  |  |  |
| RRasE1K12P3T | $(T)_{15}$ TGCGCTTTTCCCAACACCT | 10.5 | 84 | 8 |
| RRasE1K12P3C | $(T)_{15}$ TGCGCTTTTCCCAACACCC | 1.6 | 32 | 20 |
| RRasE1K12P3G | $(T)_{15}$ TGCGCTTTTCCCAACACCG | 2.2 | 33 | 15 |
| RRasE1K13P1C | $(T)_{15}$ GTGCGCTTTTCCCAACACC |  |  |  |
| RRasE1K13P1A | $(T)_{15}$ GTGCGCTTTTCCCAACACA | 14 | 84 | 6 |
| RRasE1K13P1T | $(T)_{15}$ GTGCGCTTTTCCCAACACT | 2.1 | 130 | 61.9 |
| RRasE1K13P1G | $(T)_{15}$ GTGCGCTTTTCCCAACACG | 13 | 117 | 9 |
| RRasE1K13P2C | $(T)_{15}$ AGTGCGCTTTTCCCAACAC |  |  |  |
| RRasE1K13P2A | $(T)_{15}$ AGTGCGCTTTTCCCAACAA | 22 | 91 | 4.14 |
| RRasE1K13P2T | $(T)_{15}$ AGTGCGCTTTTCCCAACAT | 4 | 199 | 49.75 |
| RRasE1K13P2G | $(T)_{15}$ AGTGCGCTTTTCCCAACAG | 23 | 132 | 5.74 |
| RRasE1K13P3A | $(T)_{15}$ CAGTGCGCTTTTCCCAACA |  |  |  |
| RRasE1K13P3T | $(T)_{15}$ CAGTGCGCTTTTCCCAACT | 13 | 270 | 20.77 |
| RRasE1K13P3C | $(T)_{15}$ CAGTGCGCTTTTCCCAACC | 1.4 | 40 | 28.57 |
| RRasE1K13P3G | $(T)_{15}$ CAGTGCGCTTTTCCCAACG | 2.3 | 63 | 27.39 |
| Exon 2 Reverse |  |  |  |  |
| RRasE2K61P1G | $(T)_{15}$ CATGGCACTGTACTCTTCTTG |  |  |  |
| RRasE2K61P1A | $(T)_{15}$ CATGGCACTGTACTCTTCTTA | 7.5 | 52 | 6.93 |
| RRasE2K61P1T | $(T)_{15}$ CATGGCACTGTACTCTTCTTT | 16 | 77 | 4.81 |
| RRasE2K61P1C | $(T)_{15}$ CATGGCACTGTACTCTTCTTC | 10 | 30 | 3 |
| RRasE2K61P2T | $(T)_{15}$ TCATGGCACTGTACTCTTCTT |  |  |  |
| RRasE2K61P2A | $(T)_{15}$ TCATGGCACTGTACTCTTCTA | 17 | 92 | 5.4 |
| RRasE2K61P2C | $(T)_{15}$ TCATGGCACTGTACTCTTCTC | 7 | 41 | 5.86 |
| RRasE2K61P2G | $(T)_{15}$ TCATGGCACTGTACTCTTCTG | 32 | 128 | 4 |

TABLE 2-continued

|   | | ASE | PrASE | PrASE/ASE |
|---|---|---|---|---|
| RRasE2K61P3T | (T)$_{15}$ CTCATGGCACTGTACTCTTCT | | | |
| RRasE2K61P3A | (T)$_{15}$ CTCATGGCACTGTACTCTTCA | 17 | 48 | 2.82 |
| RRasE2K61P3C | (T)$_{15}$ CTCATGGCACTGTACTCTTCC | 10 | 36 | 3.6 |
| RRasE2K61P3G | (T)$_{15}$ CTCATGGCACTGTACTCTTCG | 31 | 112 | 3.61 |

Figure 8:
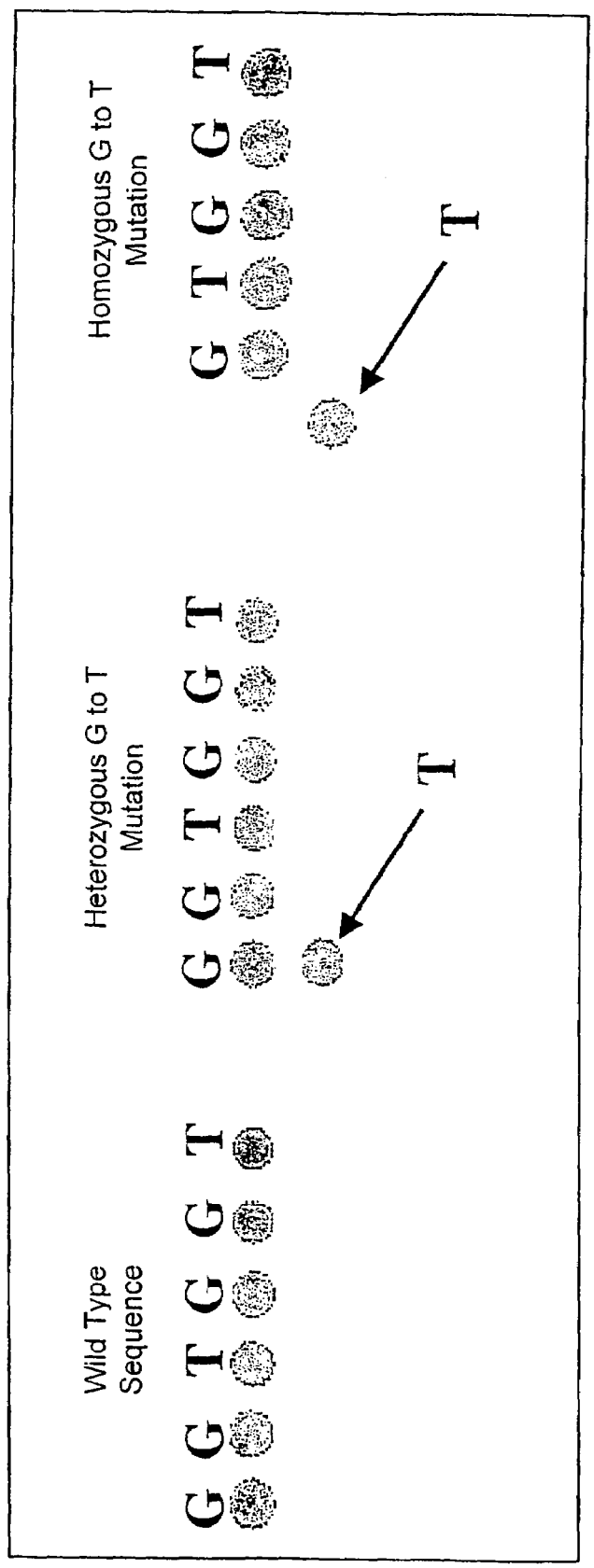
FIG. 8—Detection of mutations in exon 1 of the N-ras gene by the assay of the present invention.

FIG. 8 shows the use of the PrASE technology to detect mutations. The mutation in this case is a G to T substitution. As shown in FIG. 8A, in the wild type sequence, no signal is indicated when the oligonucleotides are mismatched to the template. However, in the heterozygous case (50% wild type and 50% mutation) (FIG. 8B) the mismatched primer (the oligonucleotide with the base A in the 3'-terminus) hybridized to the template results in a signal as high as the matched primer hybridized to the template signal. In the homozygous mutation case (FIG. 8C) (e.g. 100% T mutation), only the signal from the oligonucleotide with the base A in the 3'-terminus is detected.

In conclusion, this investigation shows the possibility of accurately detecting mutations in disease related genes by PrASE, however, it also shows the possibility to score SNPs since the SNP analysis is based on the same methodology.

Example 2

Proteinase-Mediated Allele-Specific Primer Extension (PrASE) on DNA Microarrays—Re-Sequencing of Part of the p53 Tumor Suppressor Gene In this Example, the microarray assay has been used to re-sequence a 7-base stretch in exon 5 of the p53 tumour suppresser gene. Partially overlapping extension primers were designed, but instead of two variants differing only in the 3'-terminus nucleotides as for SNPs, all four possible variants of 3'-terminus were used. Thus, four primers were designed, each with a different base at the 3' end. The use of all four possible variants of 3'-terminus allele-specific primers allows detection of all possible mutations instead of two allelic variants. To perform detection and characterization of mutations in these 7 bases, 28 partially overlapping oligonucleotides were spotted on the chip. These extension primers were then allowed to hybridize to a synthetic 60-mer oligonucleotide template, followed by extension in situ using fluorescent labelled nucleotides. After the extension, the microarray was scanned and fluorescent intensities were measured and compared. In this study, two base-specific primer extension assays were compared. In one assay, conventional allele-specific primer extension (ASE) was used and the results showed that in the ASE assay some mismatched primers to the template give such high rates of extension that the allocated genotype is incorrect. In the second assay a thermo-stable protein degrading (digesting) enzyme, Proteinase K, was included in the base-specific extension reaction and this modification resulted in only the correct extension products being produced, from only the matched primer-template duplex.

Materials and Methods

Oligonucleotides

The allele specific extension primers were synthesized with a 5' amino group, which facilitates covalent immobilization on the glass slide. A spacer sequence of 15 poly-T bases was included at the 5' end of the gene specific sequence that contained 18 nucleotides (Table 3). The gene specific sequences of the extension primers were designed to have a Tm of 62-64° C. with the 3'-nucleotide hybridizing at the variant position. A synthetic oligonucleotide of 60-mers (nucleotides 13205-19 of exon 5 of the p53 gene, accession number U94788) was used to hybridize to the allele specific extension primers (Table 3). The oligonucleotides were synthesized by MWG-Biotech, Germany.

TABLE 3

Gene specific extension primers.

| 3'-position | Sequence 5'->3' |
|---|---|
| 205T | (T)$_{15}$CGGAGGTTGTGAGGCGCT |
| 205A | (T)$_{15}$CGGAGGTTGTGAGGCGCA |
| 205C | (T)$_{15}$CGGAGGTTGTGAGGCGCC |
| 205G | (T)$_{15}$CGGAGGTTGTGAGGCGCG |
| 206G | (T)$_{15}$GGAGGTTGTGAGGCGCTG |
| 206A | (T)$_{15}$GGAGGTTGTGAGGCGCTA |
| 206C | (T)$_{15}$GGAGGTTGTGAGGCGCTC |
| 206T | (T)$_{15}$GGAGGTTGTGAGGCGCTT |
| 207C | (T)$_{15}$GAGGTTGTGAGGCGCTGC |
| 207A | (T)$_{15}$GAGGTTGTGAGGCGCTGA |
| 207G | (T)$_{15}$GAGGTTGTGAGGCGCTGG |
| 207T | (T)$_{15}$GAGGTTGTGAGGCGCTGT |
| 208C | (T)$_{15}$AGGTTGTGAGGCGCTGCC |
| 208A | (T)$_{15}$AGGTTGTGAGGCGCTGCA |
| 208G | (T)$_{15}$AGGTTGTGAGGCGCTGCG |
| 208T | (T)$_{15}$AGGTTGTGAGGCGCTGCT |
| 209C | (T)$_{15}$GGTTGTGAGGCGCTGCCC |
| 209A | (T)$_{15}$GGTTGTGAGGCGCTGCCA |
| 209G | (T)$_{15}$GGTTGTGAGGCGCTGCCG |
| 209T | (T)$_{15}$GGTTGTGAGGCGCTGCCT |
| 210C | (T)$_{15}$GTTGTGAGGCGCTGCCCC |
| 210A | (T)$_{15}$GTTGTGAGGCGCTGCCCA |
| 210G | (T)$_{15}$GTTGTGAGGCGCTGCCCG |
| 210T | (T)$_{15}$GTTGTGAGGCGCTGCCCT |
| 211C | (T)$_{15}$TTGTGAGGCGCTGCCCCC |
| 211A | (T)$_{15}$TTGTGAGGCGCTGCCCCA |

TABLE 3-continued

Gene specific extension primers.

| 3'-position | Sequence 5'->3' |
|---|---|
| 211G | (T)₁₅TTGTGAGGCGCTGCCCCG |
| 211T | (T)₁₅TTGTGAGGCGCTGCCCCT |

TABLE 4

Hybridized oligonucleotide

Sequence 5'->3'

ACCATCGCTATCTGAGCAGCGCTCATGGTGGGGGCAGCGCCTCACAACCTCCGTCATGTG

Microarray Preparation

Amino linked oligonucleotide capture probes suspended at a concentration of 20 µM in 150 mM sodium phosphate pH 8.5 and 0.06% sarkosyl were spotted using a GMS 417 arrayer (Affymetrix, USA) on 3D-link activated slides (Motorola Life Sciences, IL, USA). Sarkosyl was added to the spotting solution as it improved spot uniformity. The primers were printed in 16 clusters on the microscope slide and each primer was duplicated. The distance between the spots was 250 µM and the spot diameter was approximately 200 µM. The clusters were positioned in two columns of eight rows each with a 9 mm distance between cluster centres. After printing, the arrays were incubated overnight in a humid chamber followed by post coupling as outlined by the manufacturer. Briefly the slides were incubated at 50° C. for 15 minutes in blocking solution (50 mM ethanol amine, 0.1M Tris pH 9 and 0.1% SDS), rinsed twice in dH₂O and washed with 4×SSC/0.1% SDS (pre-warmed to 50° C.) for 15 to 60 minutes. The arrays were then rinsed in H₂O and dried by centrifugation for 3 minutes at 800 rpm.

Spatial Separation of Samples

The 16 clusters on the microarray slide were separated during hybridization and extension using a silicone mask (Elastosile 601 A/B Wacker Chemie GmbH, Munich, Germany) molded in a 96 well plate and excised to fit the slide. A Custom made rack was used to press the silicone firmly to the slide and keep it in place during the reactions.

Hybridization and Allele Specific Extension

Five pmol of the synthetic oligonucleotide (s/s 60-mer), was hybridized in 5×SSC 0.2% SDS and 0.5 µg single strand Binding protein (SSB) (in house produced) for about one hour in a final volume of 60 µl/well. The slides were washed in 2×SSC 0.1% SDS at 50° C. for 10 min and then rinsed in 0.1×SSC and dried by a modified table centrifuge.

The primer extension reaction was prepared so that a pre-heated (65° C.) mixture (50 µl) of Proteinase K and dNTP's was added to a well containing a mixture (10 µl) of Klenow fragment (room temperature). The final extension mixture contained 8U Klenow (in house produced), 0.5 µM dNTP (50% Cy5 labeled dCTP) (Amersham Pharmacia Biotech), 0.25% BSA, 1 mM DTT, 5 mM MgCl₂ and 24 µg of Proteinase K (Boehringer Mannheim GmbH, Germany) with a final volume of 60 µl/well. When conventional allele-specific primer extension was performed, a 60 µl extension mixture was prepared and added to the well. This extension mixture comprised of 8 U Klenow (in house produced), 0.5µM dNTP (50% Cy5 labeled dCTP) (Amersham Pharmacia Biotech), 0.25% BSA, 1 mM DTT and 5 mM MgCl₂ and the reaction was carried on at 37° C. After extension reaction, the slide was washed in 2×SSC 0.1% SDS at 50° C. for 10 min and then rinsed in first 0.2×SSC followed by 0.1×SSC and dried by centrifugation on a modified table centrifuge.

Data Acquisition

Following the extension data was obtained by scanning slides with a GMS 428 scanner (Affymetrix, USA). Data was analyzed in GenePix 4.0, (Axon instruments, USA). All spots were manually inspected prior to data extraction.

Results and Discussion

Allele-specific extension is traditionally thought of as a tool for detection of mutations in pre-defined positions such as single nucleotide polymorphisms (SNPs). The technique uses the discriminatory property of DNA polymerase to extend a 3'-matched but not a 3'-mismatched primer. The weakness of this technology is the non-specific extension of 3'-mismatched primers. However, in this Example, by exploiting the protein digesting (degrading) property of Proteinase K, an error rate of zero was achieved. This Proteinase-mediated allele-specific Primer extension (PrASE) was performed in a microarray format to re-sequence and detect unknown mutations in a 7-base stretch in the p53 tumour suppresser gene. In this study, conventional allele-specific primer extension (ASE) assay was compared to Proteinase-mediated allele-specific Primer extension (PrASE). In the ASE assay the results showed extension of 3'-mismatched primer hybridized to the template leading to incorrect interpretation of genotypes. In the PrASE assay, the inclusion of the thermo-stable protein degrading (digesting) enzyme, Proteinase K, resulted in correct and specific extension products, and thus, correct genotype allocation.

Figure 7:
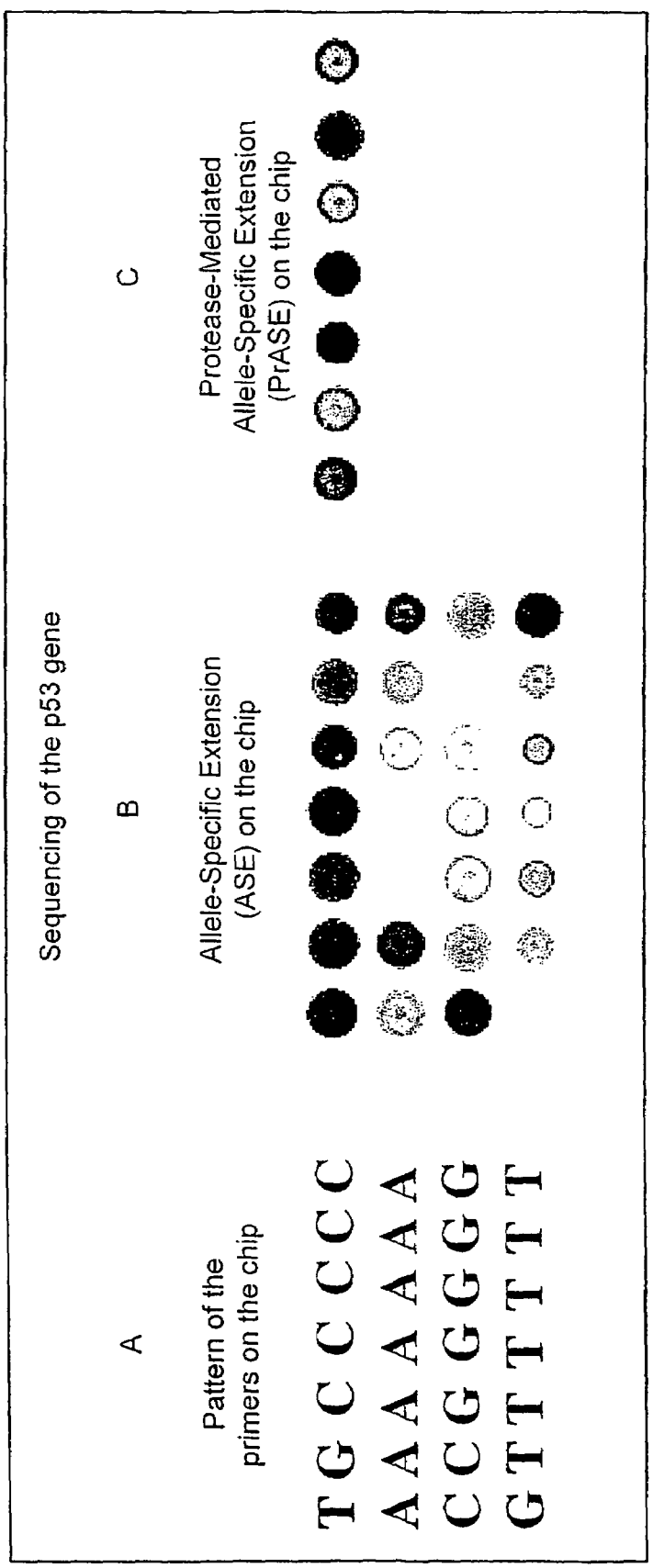
FIG. 7—Comparison of conventional Allele-Specific Extension (ASE) assays to the assay of the present invention using the p53 gene.

As mentioned above, in the experimental setup, conventional Allele-Specific Primer Extension (ASE) was compared to Proteinase-Mediated Allele-Specific Primer Extension (PrASE). As shown in FIG. 7B (in which ASE has been performed) some of the 3'-mismatched primers hybridized to the target template exhibit such high levels of extension that the typing results obtained are incorrect. Examples of such non-specific mismatched extensions are C to A (ratio of 2.21), A to C (ratio of 2.13), T to G (ratio of 2.01), A to G (ratio of 1.66) and T to G (ratio of 1.02) (for ratios see Table 5). FIG. 6C shows that inclusion of the thermo-stable protein digesting (degrading) enzyme, Proteinase K, in the allele-specific extension reactions avoids the problems associated with ASE and results in the correct sequencing results. Using the PrASE assay, the poor ratios obtained by ASE are found to be 21.45, 15.77, 5.41, 16.71 and 34.97, respectively.

Table 5 depicts a summary of the results obtained (match to mismatch ratios) obtained with ASE and PrASE. In Table 5, the first column shows the name of allele-specific oligonucleotides (spotted on the microarray) and the following column shows the sequence of these allele-specific oligonucleotides. For each base position, one oligonucleotide is 3'-terminus matched to the target template (always the first oligonucleotide) and three oligonucleotides are 3'-mismatched to the target template (the three oligonucleotides beneath the first one). The allele-specific oligonucleotides for each base position are clustered. The third column in Table 5 shows the results obtained from the ASE assay for matched signal (signal that was obtained from the first oliginucleotide) to the mismatched signals as a ratio. The ratio for the matched signal to each of the mismatched signals is indicated in the same row as the mismatched oligonucleotide. For example, in the first allele-specific oligonucleotide cluster, the target template has the base A in the position to be sequenced and therefore the first oligonucleotide will be matched to the base T at the 3'-terminus and thus giving high levels of signal (obtained from the labeled and incorporated nucleotide). However, the second oligonucleotide in this cluster has an A at the 3'-terminus which is mismatched to the base T in the target template and therefore gives a low signal. The ratio of matched signal to mismatched signal in this example is 5.86 and is indicated in the same row as the mismatched oligonucleotide with the base A in the 3'-terminus. In a previous study we performed a statistical calculation (A. Ahmadian et al, 2001, Nucleic Acids Research, supra) and concluded that ratios equal or below 2 are definitely heterozygous, and for an allelic sample to be considered as homozygous this ratio has to be more than 4. As shown in the ASE column (ratios for the ASE assay), some of the ratios are incorrect and indicating a heterozygous (mutated) target DNA template when the target DNA template was actually homozygous (wild type sequence). Nevertheless, when PrASE was performed the PrASE ratios (see PrASE column in Table 5) were far greater than the ASE ratios. The ratio data presented in Table 5 is result of mean value of two replicates for each spot.

TABLE 5

| 3'-position | Sequence 5'->3' | ASE | PrASE |
|---|---|---|---|
| 205T | (T)$_{15}$CGGAGGTTGTGAGGCGCT | | |
| 205A | (T)$_{15}$CGGAGGTTGTGAGGCGCA | 7.22 | 12.94 |
| 205C | (T)$_{15}$CGGAGGTTGTGAGGCGCC | 2.21 | 21.45 |
| 205G | (T)$_{15}$CGGAGGTTGTGAGGCGCG | 63.45 | 56.58 |
| 206G | (T)$_{15}$GGAGGTTGTGAGGCGCTG | | |
| 206A | (T)$_{15}$GGAGGTTGTGAGGCGCTA | 2.13 | 15.77 |
| 206C | (T)$_{15}$GGAGGTTGTGAGGCGCTC | 5.61 | 18.87 |
| 206T | (T)$_{15}$GGAGGTTGTGAGGCGCTT | 6.73 | 42.21 |
| 207C | (T)$_{15}$GAGGTTGTGAGGCGCTGC | | |
| 207A | (T)$_{15}$GAGGTTGTGAGGCGCTGA | 27.66 | 50.73 |
| 207G | (T)$_{15}$GAGGTTGTGAGGCGCTGG | 15.17 | 43.43 |
| 207T | (T)$_{15}$GAGGTTGTGAGGCGCTGT | 7.83 | 10.53 |
| 208C | (T)$_{15}$AGGTTGTGAGGCGCTGCC | | |
| 208A | (T)$_{15}$AGGTTGTGAGGCGCTGCA | 15.40 | 82.67 |
| 208G | (T)$_{15}$AGGTTGTGAGGCGCTGCG | 9.53 | 37.98 |
| 208T | (T)$_{15}$AGGTTGTGAGGCGCTGCT | 12.11 | 37.52 |
| 209C | (T)$_{15}$GGTTGTGAGGCGCTGCCC | | |
| 209A | (T)$_{15}$GGTTGTGAGGCGCTGCCA | 6.16 | 23.53 |
| 209G | (T)$_{15}$GGTTGTGAGGCGCTGCCG | 6.15 | 35.82 |
| 209T | (T)$_{15}$GGTTGTGAGGCGCTGCCT | 2.01 | 5.41 |
| 210C | (T)$_{15}$GTTGTGAGGCGCTGCCCC | | |
| 210A | (T)$_{15}$GTTGTGAGGCGCTGCCCA | 23.43 | 85.73 |
| 210G | (T)$_{15}$GTTGTGAGGCGCTGCCCG | 152.59 | 221.64 |
| 210T | (T)$_{15}$GTTGTGAGGCGCTGCCCT | 20.87 | 75.40 |

TABLE 5-continued

| 3'-position | Sequence 5'->3' | ASE | PrASE |
|---|---|---|---|
| 211C | (T)$_{15}$TTGTGAGGCGCTGCCCCC | | |
| 211A | (T)$_{15}$TTGTGAGGCGCTGCCCCA | 1.66 | 16.71 |
| 211G | (T)$_{15}$TTGTGAGGCGCTGCCCCG | 4.08 | 26.26 |
| 211T | (T)$_{15}$TTGTGAGGCGCTGCCCCT | 1.02 | 34.97 |

In conclusion, this study demonstrates the possibility of accurately re-sequencing and consequently detecting mutations in the p53 gene and other disease related genes by PrASE. This investigation also shows the possibility to score SNPs by PrASE as the SNP analysis is based on the exact same methodology.

Example 3

SNP Genotyping by Multiplex Liquid-Phase Proteinase-Mediated Allele-Specific Primer Extension (PrASE) by Using Generic Oligonucleotide Arrays The results presented here provide a solution to one of the major obstacles in allele-specific primer extensions: to accurately score single nucleotide polymorphisms (SNPs). Certain mismatched configurations are known to yield extension products and hinder proper discrimination between genotypes, and consequently limiting the use of this very convenient approach. This Example describes an accurate single step extension approach suitable for high-throughput SNP typing applications. The method relies on multiplex SNP analysis by extension of paired allele-specific primers for each SNP position. In addition, in order to obtain accurate genotyping data, the method relies on the use of a thermostable protein degrading (digesting) enzyme, Proteinase K, in the extension reactions. In this method, we have taken advantage of the fact that DNA polymerase extends 3'-end mismatched primer-templates with slower reaction kinetics compared to 3'-end matched primer-template. Inclusion of Proteinase K in the extension reaction results in digestion of the DNA polymerase before extension in reactions having slow kinetics due to 3'-end mismatched primer to the allelic target but allows extension in reactions having fast kinetics due to 3'-end matched primer to the allelic target. To facilitate multiplex (i.e. multiple) SNP typing, each allele-specific extension primer was designed and synthesized with a specific tag. A generic tag-array on glass slides was prepared and the product of multiplexed Proteinase K mediated allele-specific extension (PrASE) was hybridized to this tag-array.

Materials and Methods

SNPs

13 SNP positions were selected from two databases with the site addresses www.snp.cshl.org and www.hgbase.interactiva.de. The name of the SNPs, the allele alternatives and the chromosomal locations were 24 (T/C) (Xq28), 155 (T/C) (20p11), 2384 (C/T) (22q13), 5175 (T/C) (20q13) and 3288 (T/C) (11q23) taken from www.hgbase.interactiva.de and TSC0140687 (A/G) (11p13-11p12), TSC0105540 (A/G) (12p13.3), TSC0139938 (A/G) (12q), TSC0009926 (C/T) (15q21.2), TSC0110127 (C/T) (1p35), TSC0100056 (A/G) (22q11.2), TSC0125096 (A/G) (22q12.3-22q13.2) and TSC0105206 (A/G) (5p) taken from www.snp.cshl.org.

PCR Amplification, Sample Preparation and Multiplex PrASE Reaction

The SNPs were amplified in a nested PCR fashion by a multiplex outer PCR followed by 13 inner and specific PCRs. One of the inner PCR primers in each set was biotinylated at the 5'-end to allow immobilization. Five micro liters of each of the 13 PCR products were mixed. Biotinylated and mixed inner PCR products were immobilized onto streptavidin-coated super paramagnetic beads (Dynabeads M270; Dynal, Oslo, Norway) and single-stranded DNA was obtained by alkali elution of the non-biotinylated strand. This procedure was performed by a Magnetrix robot (Magnetic Biosolutions, Stockholm, Sweden). The supernatant was then discarded and all 26 allele-specific primers (2 allele-specific primer/SNP) (5 pmol/primer) were added and annealed to the captured strand. Each allele-specific primer contained a specific tag (a barcode) at its 5'-end. The allele-specific primers with 5'-terminus tags are listed in Table 6.

TABLE 6

Allele-specific primers with corresponding tag

| | | |
|---|---|---|
| LT2 | SNP 24 | GCAGATCAATTAATACGATACCTGCGGTGTCCTGTCCTCTGAGACG |
| LT3 | SNP 24 A | GGTTCTGTTCTTCGTTGACATGAGGGTGTCCTGTCCTCTGAGACA |
| LT4 | SNP 155 A | TTAGTCTCCGACGGCAGGCTTCAATATGGCAAAGTCCAGGGCACA |
| LT5 | SNP 155 G | CTGTGACAGAGCCAACACGCAGTCTATGGCAAAGTCCAGGGCACG |
| LT6 | SNP 2384 G | CCTGGTGGTTGACTGATCACCATAACTCAGAAACTTCTTGAACCCAG |
| LT7 | SNP 2384 A | GCATGTATAGAACATAAGGTGTCTCCTCAGAAACTTCTTGAACCCAA |
| LT8 | SNP 5175 G | GCTAGATGAAGAGCAAGCGCATGGATGTACGGGAGGAGGCATGG |
| LT9 | SNP 5175 A | TACAACCGACAGATGTATGTAAGGCTGTACGGGAGGAGGCATGA |
| LT10 | SNP 3288 G | TTCAATCTGGTCTGACCTCCTTGTGGCCCCAGGTTCCCTAGTCG |
| LT11 | SNP 3288 A | ACACGATGTGAATATTATCTGTGGCGCCCCAGGTTCCCTAGTCA |
| LT12 | SNP 0684 T | TTGAAGTTCGCAGAATCGTATGTGTCAAGAAAGCACTGACCTGGAT |
| LT13 | SNP 0684 C | AACGTCTGTTGAGCACATCCTGTAACAAGAAAGCACTGACCTGGAC |
| LT 14 | SNP 5540 G | GGCAACTCATGCAATTATTGTGAGCGCAGAGGGGACGGGAAAGG |
| LT 15 | SNP 5540 A | CCAGAAGTATATTAATGAGCAGTGCAGGCAGAGGGGACGGGAAAGA |
| LT 16 | SNP 9938 T | AAGCAGTCTGTCAGTCAGTGCGTGAAAAGGAAGCACCGGGGCAAAT |
| LT 17 | SNP 9938 C | AATGATGCTCTGCGTGATGATGTTGAAGGAAGCACCGGGGAAAC |
| LT 18 | SNP 9926 G | AATACACGAAGGAGTTAGCTGATGCGTGTCCACCACACCCCTGG |
| LT 19 | SNP 9926 A | GCTGTTAATCATTACCGTGATAACGCCGTGTCCACCACACCCCTGA |
| LT 20 | SNP 0127 G | GCGGAACGGTCAGAGAGATTGATGTTGGCGGTTGTGCGGATTCAG |
| LT 21 | SNP 0127 A | GTTATGGTCAGTTCGAGCATAAGGCTGGCGGTTGTGCGGATTCAA |
| LT 22 | SNP 0056 T | TTACCTATGATTGATCGTGGTGATATCCGGGTGGAGGGACTGGAACAT |
| LT 23 | SNP 0056 C | GCTGTGGCATTGCAGCAGATTAAGGGGTGGAGGGACTGGAACAC |
| LT 24 | SNP 5096 T | TGACGTCATTGTAGGCGGAGAGCTAGGAGACATAAGTACTTCTCCT |
| LT 25 | SNP 5096 C | TCAATAATCAACGTAAGGCGTTCCTGGAGACATAAGTACTTCTCCC |
| LT 26 | SNP 5206 T | TTATCGGCTACATCGGTACTGACTCAAAGACCAAAACATTTCAAGACAT |
| LT 27 | SNP 5206 C | CCATTATCGCCTGGTTCATTCGTGAAAAGACCAAAACATTTCAAGACAC |

After annealing, excess allele-specific primers were discarded and the immobilized single-stranded DNA with annealed primers was mixed with Proteinase K and dye-labelled dNTPs (Cy5 C and Cy5 T). This mixture was incubated at 50° C. and then DNA polymerase (Klenow polymerase) was added into this mixture. After polymerization, the enzymes and dNTPs were discarded and immobilized DNA was washed. The immobilized DNA was then treated with alkali (0.1 M) and the supernatant (the PrASE product) was neutralized with HCl (0.1 M). The PrASE products (each containing a specific tag at the 5'-terminus) were then hybridized to glass slides with generic tag-arrays. The sequence of the tags on the glass slides is listed in Table 7. A comparison of Table 6 and Table 7 shows that each tag on the glass slide is complementary to one of the tags on the allele-specific extension primers. The sequence of all these unique sequence tags was taken from www.genome.wi.m-it.edu.

TABLE 7

List of sequence tags on the microarray chips

| LT2 | CGCAGGTATCGTATTAATTGATCTGC |
|---|---|
| LT3 | CCTCATGTCAACGAAGAACAGAACC |
| LT4 | ATTGAAGCCTGCCGTCGGAGACTAA |
| LT5 | AGACTGCGTGTTGGCTCTGTCACAG |
| LT6 | TTATGGTGATCAGTCAACCACCAGG |
| LT7 | GAGACACCTTATGTTCTATACATGC |
| LT8 | TCCATGCGCTTGCTCTTCATCTAGC |
| LT9 | GCCTTACATACATCTGTCGGTTGTA |
| LT10 | CACAAGGAGGTCAGACCAGATTGAA |
| LT11 | GCCACAGATAATATTCACATCGTGT |
| LT12 | ACACATACGATTCTGCGAACTTCAA |
| LT13 | TTACAGGATGTGCTCAACAGACGTT |
| LT14 | GCTCACAATAATTGCATGAGTTGCC |
| LT15 | CTGCACTGCTCATTAATATACTTCTGG |
| LT16 | TTCACGCACTGACTGACAGACTGCTT |
| LT17 | CAACATCATCACGCAGAGCATCATT |
| LT18 | GCATCAGCTAACTCCTTCGTGTATT |
| LT19 | GGCGTTATCACGGTAATGATTAACAGC |
| LT20 | ACATCAATCTCTCTGACCGTTCCGC |
| LT21 | GCCTTATGCTCGAACTGACCATAAC |
| LT22 | CGGATATCACCACGATCAATCATAGGTAA |
| LT23 | CCTTAATCTGCTGCAATGCCACAGC |
| LT24 | TAGCTCTCCGCCTACAATGACGTCA |
| LT25 | AGGAACGCCTTACGTTGATTATTGA |
| LT26 | GAGTCAGTACCGATGTAGCCGATAA |
| LT27 | ACTCGAATGAACCAGGCGATAATGG |
| LT28 | ATTATATCTGCCGCGAAGGTACGCC |
| LT29 | GGACAGACAGTGGCTACGGCTCAGTT |
| LT30 | CGGTATTCGCTTAATTCAGCACAAC |
| LT31 | GCTCTTACCTGTTGTGCAGATATAA |

Microarray Preparation and Spatial Separation of Samples

Amino linked oligonucleotide capture probes suspended at a concentration of 20 μM in 150 mM sodium phosphate pH 8.5 and 0.06% sarkosyl were spotted using a GMS 417 arrayer (Affymetrix, USA) on 3D-link activated slides (Motorola Life Sciences, IL, USA). Sarkosyl was added to the spotting solution as it improved spot uniformity. The primers were printed in 16 clusters on the microscope slide, each cluster containing one spot of a duplicated primer. The distance between the spots was 250 μM and the spot diameter was approximately 200 μM. The clusters were positioned in two columns of eight rows each with a 9 mm distance between cluster centres. After printing, the arrays were incubated overnight in a humid chamber followed by post coupling as outlined by the manufacturer. Briefly the slides were incubated at 50° C. for 15 minutes in blocking solution (50 mM ethanol amine, 0.1M Tris pH 9 and 0.1% SDS), rinsed twice in dH$_2$O and washed with 4×SSC/0.1% SDS (pre-warmed to 50° C.) for 15 to 60 minutes. The arrays were then rinsed in H$_2$O and dried by centrifugation for 3 minutes at 800 rpm.

The 16 clusters on the microarray slide were separated during hybridization by using a silicone mask (Elastosile 601 A/B Wacker Chemie GmbH, Munich, Germany) molded in a 96 well plate and excised to fit the slide. A Custom made rack was used to press the silicone firmly to the slide and keep it in place during the reactions.

Data Acquisition

Following the hybridization, data was obtained by scanning slides with a GMS 428 scanner (Affymetrix, USA). Data was analyzed in GenePix 4.0, (Axon instruments, USA). All spots were manually inspected prior to data extraction.

Results and Discussion

Figure 9:
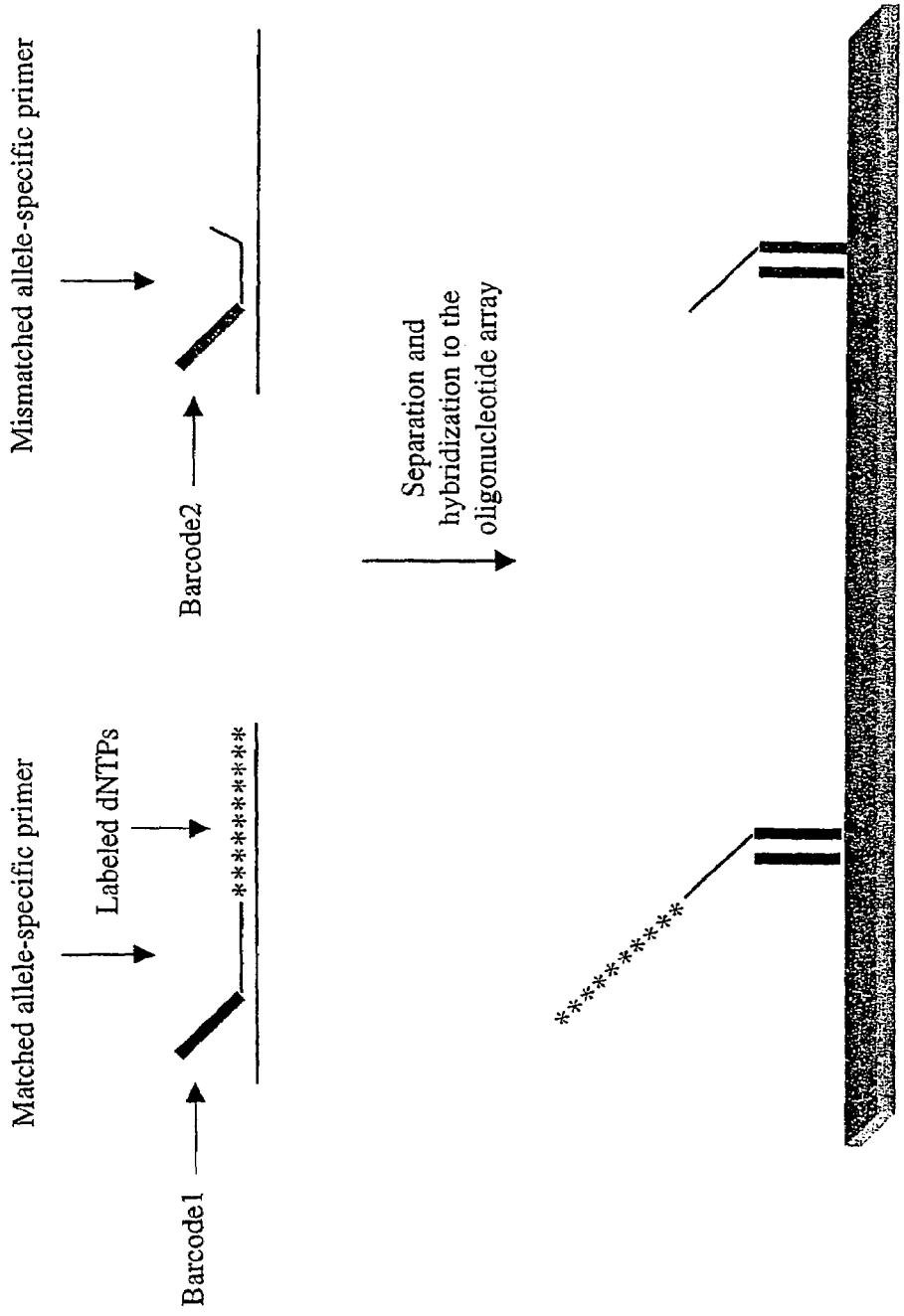
FIG. 9—A depiction of multiplex liquid-phase assay according to the invention and hybridization to generic oligonucleotide array.
Figure 10:
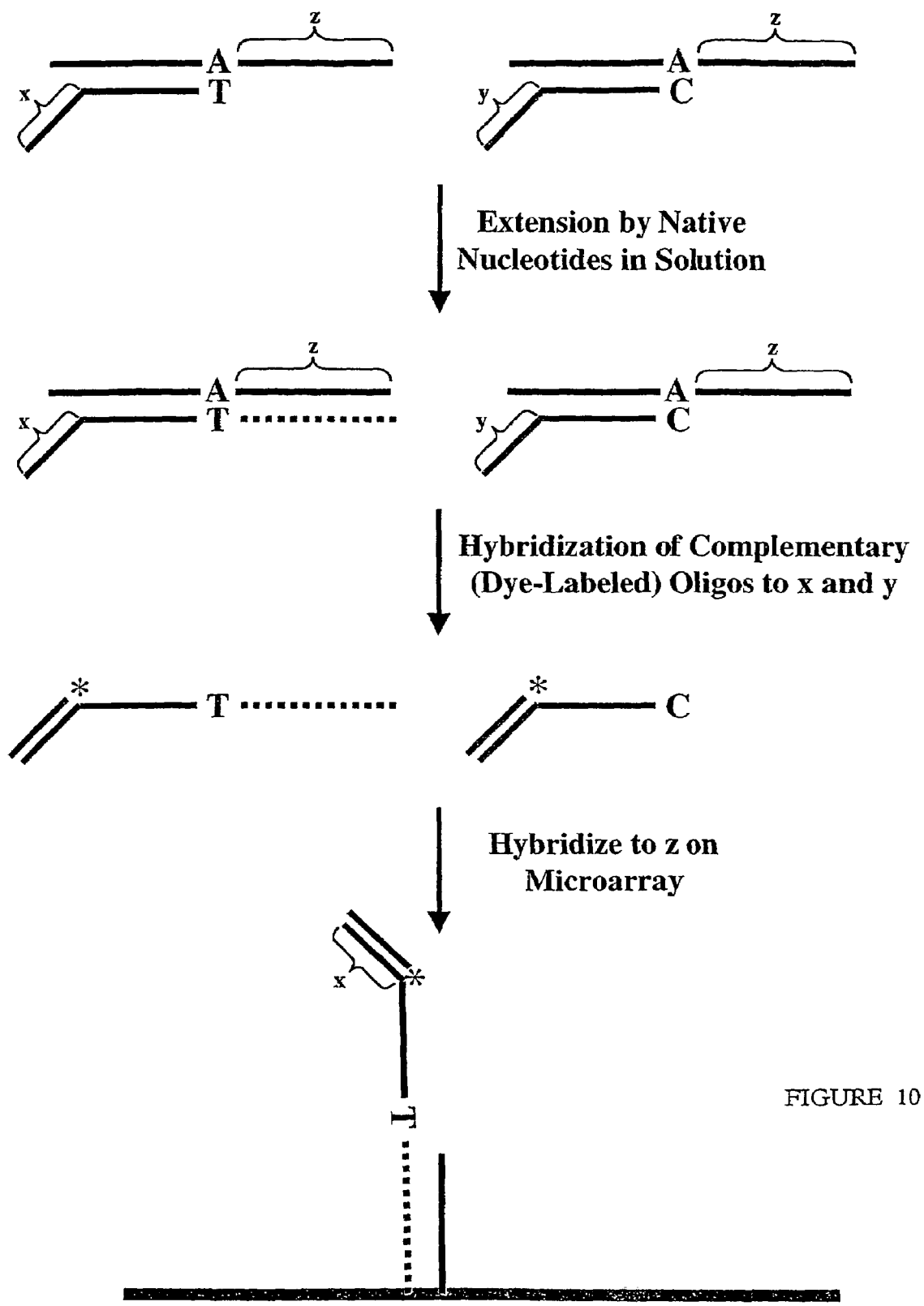
FIG. 10—A liquid-phase multiplex assay is performed in a single tube. The 5'-end of the allele-specific primers each carry a different barcode and the primer extension is performed with native (non-labelled) nucleotide(s) and the extension product (the 3'-sequence of the extended primer(s)) is hybridized to the oligonucleotides on the microarray chip. Matched primers are allowed to extend, and the 3'-sequence of the matched primer can be hybridized and detected. However, the mismatched primers do not extend during the primer extension reaction and consequently lack the 3'-sequence that can be hybridized to the oligonucleotides on the array. Thus, they do not hybridize to the array. The labelling of the allele-specific primers is performed indirectly by using dye-labelled oligonucleotides that are complementary to the sequence tags (barcodes) on 5'-end of the allele-specific primers. After allele-specific extension, the extension products are mixed and hybridized to labelled and complementary oligonucleotides (which are complementary to the sequence tags). The oligonucleotides are complementary to the allele-specific primer tags are labelled with two different dyes. This mixture is then hybridized to the oligonucleotides on the microarray chip, which are complementary to the extended products. The 3'-sequence of the matched primer will hybridize to the corresponding oligonucleotide on the chip and will be indirectly detected through dye-labelled oligonucleotide, which is hybridized to the tag. Mismatched primers do not extend and consequently lack 3'-sequence that can be hybridized to the oligonucleotides on the array, and thus are absent from the array.

FIG. 9 shows the principle of using sequence tags (barcodes) in an allele-specific primer extension assay for SNP typing. In this approach, instead of performing the extension reaction on the glass slide we have performed a multiplex allele-specific primer extension in solution. In addition, in order to obtain accurate genotyping data, Proteinase K was included in the extension reaction and the extension reaction was carried out at 50° C. to achieve high temperature stringency.

In this study, conventional allele-specific primer extension (ASE) assay was compared to Proteinase-mediated allele-specific primer extension (PrASE). In the ASE assay the results showed high levels of non-specific extension from 3'-mismatched primer hybridized to the template, leading to incorrect interpretation of the genotype. In the PrASE assay, the inclusion of the thermo-stable protein degrading (digesting) enzyme, Proteinase K, resulted in correct and specific extension products, and thus, correct genotyping.

Figure 11:
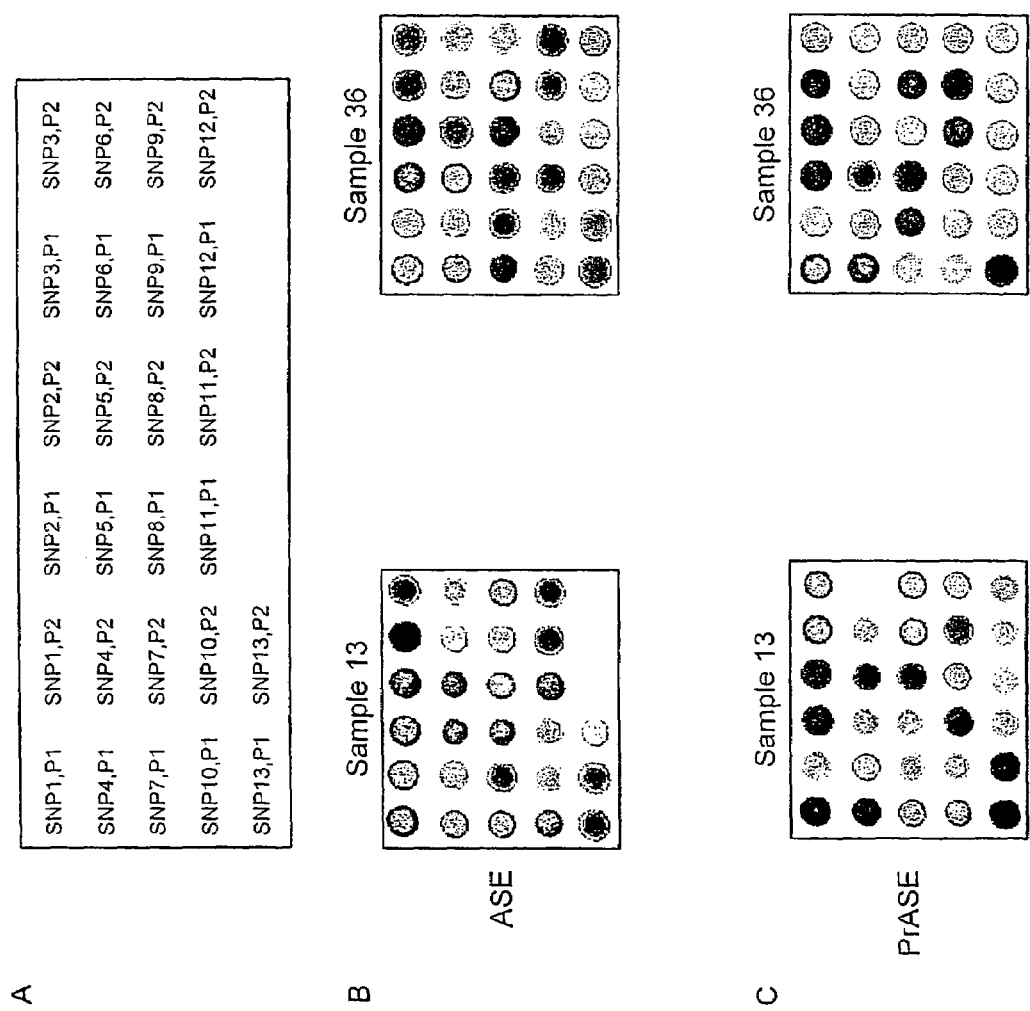
FIG. 11—Depicts a multiplex liquid-phase assay followed by hybridization to generic oligonucleotide array. Comparison of conventional allele-specific extension (ASE) assays and the assay of the current invention is shown.

As mentioned above, in the multiplex experimental setup, conventional Allele-Specific Primer Extension (ASE) was compared to Proteinase-Mediated Allele-Specific Primer Extension (PrASE). As shown in FIG. 11B (in which ASE has been performed) (samples 13 and 36) some of the 3'-mismatched primers hybridized to the target template exhibit such high levels of non-specific extension that the SNP genotyping determined from the results is incorrect (see also FIG. 12). However, when Proteinase K was included in the allele-specific primer extension, a significant difference was observed (FIG. 11C). The previously high signals for the 3'-mismatched configurations were removed via addition of Proteinase K (see also FIG. 12). In these 3'-mismatched primer-template configurations, the reaction kinetics are slow leading to degradation (digestion) of DNA polymerase by Proteinase K before any incorporation by the DNA polymerase can occur. However, in the case of 3'-matched primer-template configurations, the reaction kinetics are fast and incorporation of nucleotides takes place before degradation (digestion) of the DNA polymerase by Proteinase K.

Figure 12:
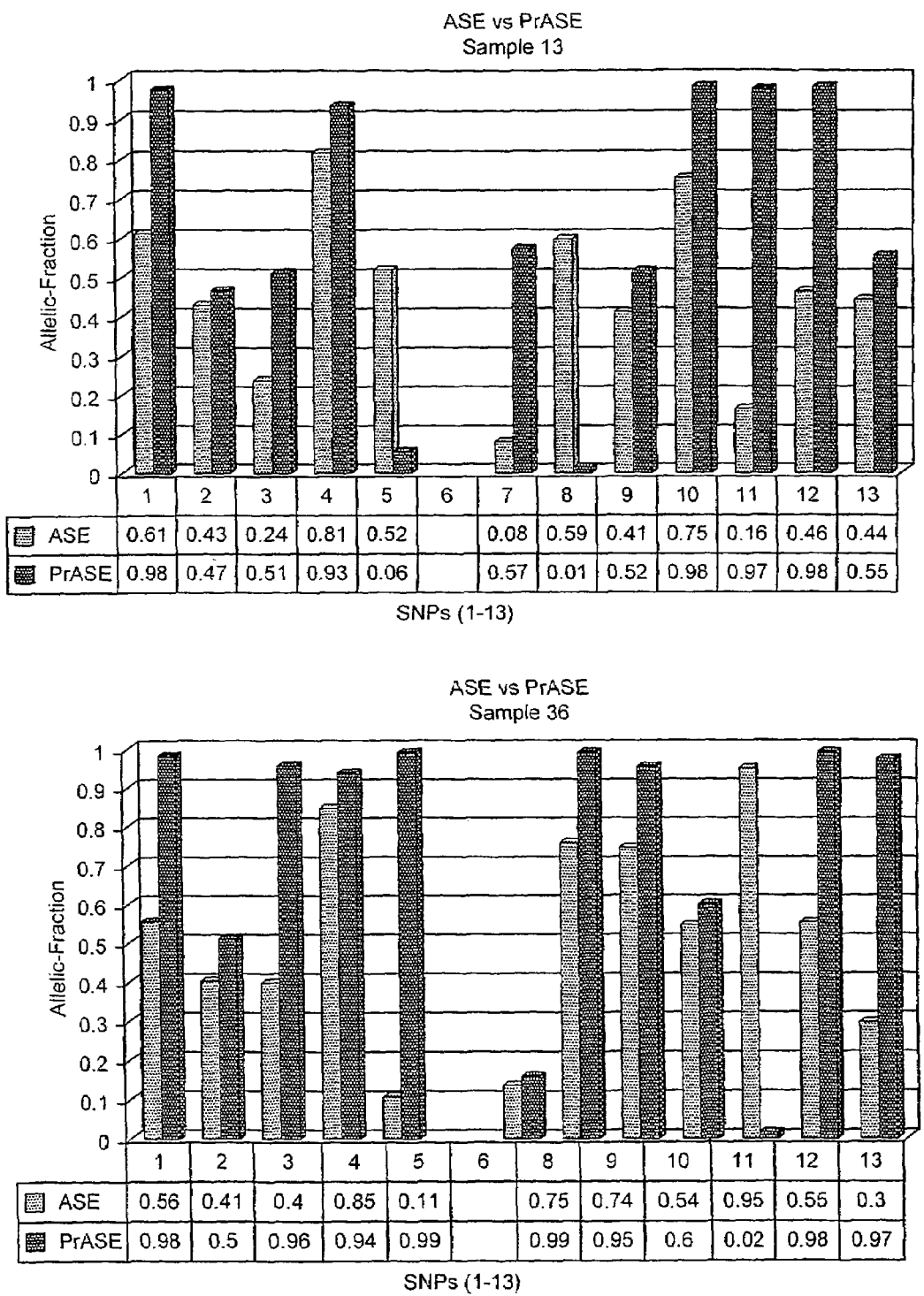
FIG. 12—To represent the extension signals from matched and mismatched primer pairs, allelic-fractions were calculated as wt/(wt+mut), in which wild type (wt) and mutant (mut) correspond to the signals from extension primers 1 and 2 respectively (see also FIG. 11). Using this formula, heterozygous samples are expected to have allelic-fractions around 0.5 (ratio of 1:1) and homozygous wt and mut are expected to have allelic-fractions of more than 0.8 and less than 0.2 respectively (as a signal to noise ratio of 4:1 is considered significant). As shown here, a high number of incorrect genotyping events have been observed by the conventional ASE method whilst the assay of the present invention has scored all SNPs correctly. For sample 13, the incorrect genotype allocation by ASE are observed in SNPs 1, 5, 7, 8, 11 and 12 and in sample 36 SNPs 1, 3, 5, 11, 12 and 13 have been scored incorrectly by ASE (see FIG. 12). Notice that in these two samples, the PCR for SNP 6 has failed and thus no genotyping data is indicated.

To represent the extension signals from matched and mismatched primer pairs, allelic-fractions were calculated as wt/(wt+mut) in which wild type (wt) and mutant (mut) correspond to the signals from extension primers 1 and 2 respectively (see Table 1) (FIG. 12). Using this formula, heterozygous samples are expected to have allelic-fractions of about 0.5 (ratio of 1:1) and homozygous wt and mut are expected to present allelic-fractions greater than 0.8 and less than 0.2, respectively (as a signal to noise ratio of 4:1 is considered significant). However, as expected, some deviation from the predicted allelic-fractions will always be observed. These deviations may be due to background on the glass surface or slight differences in hybridization efficiency of different barcodes (tags).

In FIG. 12, SNPs 1-13 correspond to SNPs 24 (G/A), 155 (A/G), 2384 (G/A), 5175 (G/A), 3288 (G/A), TSC0140687 (T/C), TSC0105540 (G/A), TSC0139938 (T/C), TSC0009926 (G/A), TSC0110127 (G/A), TSC0100056 (T/C), TSC0125096 (T/C) and TSC0105206 (T/C) respectively (the bases indicated for each SNP are the bases on the 3'-terminus of the primers and the first base here corresponds to P1 (primer 1) in FIG. 11A and the second base corresponds to P2 (primer 2) in FIG. 11A). As shown in FIG. 12, a high number of incorrect genotypes have been allocated using the conventional ASE while PrASE has scored all SNPs correctly. For sample 13, the incorrect genotype conclusions reached via ASE are observed in SNPs 1, 5, 7, 8, 11 and 12 and in sample 36 SNPs 1, 3, 5, 11, 12 and 13 have been scored incorrectly by ASE (see FIG. 12). Notice that in these two samples, the PCR for SNP 6 has failed and thus no genotyping data is indicated.

In conclusion, this Example shows that single nucleotide polymorphisms can rapidly be scored on tag-arrays with multiplex liquid-phase proteinase mediated allele-specific primer extension (PrASE). The data presented here clearly shows that inclusion of a polymerase-disabling agent such as Proteinase K in allele-specific primer extensions is essential to obtain correct and reliable genotyping results.

Example 4

Viral and Microbial Genotyping by a Unique Combination of Multiplex Competitive Type-Specific Hybridization and Proteinase-Mediated Allele-Specific Extension Followed by Hybridization to Generic Oligonucleotide Arrays Background Human papillomaviruses (HPV) are small, non-enveloped DNA viruses that are believed to be an important contributing factor in the etiology of certain benign and malignant tumorous lesions in humans such as cervical cancer. At present, there are more than 100 different HPV genotypes have been identified based on differences in DNA sequence. Human papillomaviurses are classified in low- and high-risk genotypes based on their oncogenic potential in anogential epithelia. Furthermore, this classification is almost entirely based on molecular characteristics and still under debate.

A wide variety of techniques have been used for HPV genotyping. HPV cannot be adequately cultured in vitro and serological assays only have limited accuracy, since they cannot distinguish between current and past infection. Therefore, diagnosis of HPV relies entirely on the detection of the viral DNA in clinical samples. Cytologic and histological examination does not permit direct assessment of HPV itself but diagnoses the consequences of viral infection. Therefore, detection of HPV-DNA can provide more sensitive diagnosis of infection and the associated risk for development of cervical neoplasia.

There are different techniques for HPV detection with advantages and disadvantages. The Hybrid Capture II system (HCII, Digene Corp., USA) is a signal amplification method, based on the hybridization of the target HPV-DNA to labeled RNA probes in solution and detection by specific monoclonal antibodies and a chemiluminiscent substrate, providing a quantitative measurement of HPV-DNA. Two different probe cocktails are used, one comprising of probes for low-risk genotypes 6, 22, 42 and 43 and 44; and the other containing probes for high-risk genotypes 16, 18, 31, 33, 35, 39, 45, 51, 52, 56, 58, 59 and 68. This assay has become the standard in many countries, is widely used in clinical studies and has been FDA approved. However, the HCII test has several disadvantages. The detection limit of the HCII is approximately 5000 genome equivalents and thus is less sensitive than PCR. The HCII assay does not permit identification of specific HPV genotypes but only distinguishes between high- and low-risk groups. The accuracy of the test is hampered by cross-reactivity of the two probe cocktails. Since determination of HPV persistence requires the identification of the specific HPV genotype, the HCII test cannot be used for such studies.

PCR is the most widely used target amplification method. For detection of HPV two PCR approaches are possible. The first method employs type-specific PCR methods, which are designed to exclusively amplify a single HPV genotype. Thus, to detect the presence of HPV-DNA in a single clinical sample, multiple PCR reactions should be performed separately. This method is labor-intensive and expensive. The second method is based on the use of consensus or general PCR primers to amplify a broad-spectrum of HPV genotypes. PCR primers are aimed at conserved regions among the different HPV genotypes. There are several different designs of general PCR primer sets that can be used to achieve broad-spectrum detection of HPV-DNA. GP5+/6+ and MY09/11 are two general primer sets that amply fragments of 150 and 450 base pairs respectively. Therefore, hybridization analysis of broad-spectrum PCR requires cocktails of probes as used in the hybrid capture method. PCR products may be directly sequenced to assess the sequence between the PCR primers. Rapid sequencing methods are now becoming available for high-throughput to permit application in routine analysis of clinical samples. However, it should be noted that sequence analysis is not very sensitive to simultaneously detect different sequences in a mixture. Sequences only represent a minority of the total PCR product may easily remain unnoticed and only the predominant genotype will be detected. This may be insufficient to analyze clinical samples containing a mixture of different HPV genotypes and will underestimate the prevalence of infections with multiple HPV genotypes, which has important consequences, for example, in vaccination or follow-up studies. In addition, in the sequencing approach, the cycle sequencing (or the sequencing) primer(s) are the same primers that have been used for PCR amplification and this causes enormous background problems in the sequencing if the PCR has generated non-specific fragments among the specific ones.

Another technique is the restriction fragment length polymorphism (RFLP). If mutations occur at the restriction site, the endonuclease will not recognize the site anymore and will fail to digest the DNA, resulting in different restriction fragments changing the original banding pattern. This method is relatively easy but is labor-intensive and requires adequate quality control of the restriction enzyme. More importantly, the application of this method depends on the availability of suitable restriction enzymes to permit detection of specific mutations in the target sequence. Detection of multiple HPV genotypes present in different quantities in a clinical sample by PCR and restriction fragment length polymorphism (PCR-RFLP) is usually complex and the sensitivity to detect minority genotypes is limited.

Recent studies have shown that the prevalence of HPV-DNA positivity and the prevalence of multiple HPV genotypes in the same patient is higher than assumed. Furthermore, the efficacy of large community-based HPV screening studies depends on the accuracy of the diagnostic assays used. To identify women with an increased risk for cervical neoplasia, it is obvious that detection of HPV-DNA alone is insufficient and additional aspects need to be included in the diagnosis. Accurate genotyping is essential for adequate classification of patients in a low-risk or high-risk group. Furthermore, there is preliminary evidence that presence of multiple HPV genotypes may reflect repeated exposure and may also be related to an increased risk for development of disease. To address cervical cancer worldwide, it is important to perform extensive epidemiological studies to assess the geographic distribution of HPV genotypes. Given the extensive. genetic heterogeneity of HPV, specific molecular tools will be required. Besides the identification of high-risk genotypes, also further detection of specific subtypes is clinically relevant.

Figure 13:
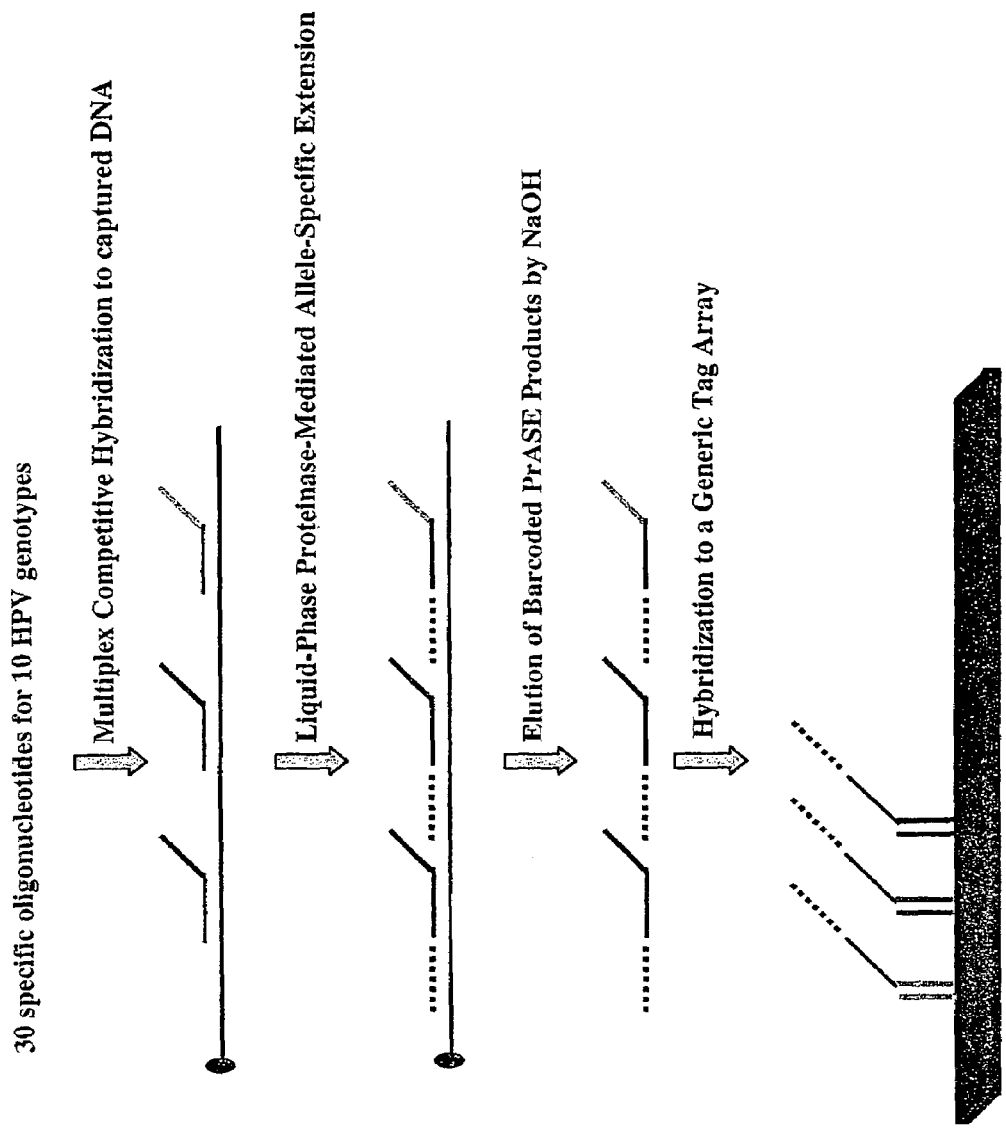
FIG. 13—Schematic presentation of Multiplex-Competitive Type-Specific Hybridization combined with the assay of the present invention, as described in Example 4.

For this purpose the inventors have developed an extremely accurate, cost effective, robust and fully automated technique for genotyping of different HPV types. In addition, we propose that this technique can be used for genotyping of other viruses and also can be used for microbial identification. The technology that the inventors have denoted Multiplex Competitive Type-Specific Hybridization combined with Protease-Mediated Allele-Specific Extension (MCTSH-PrASE) is based on a unique combination of several methods. These methods include a modified form of type-specific hybridization, liquid-phase PrASE on captured single-stranded DNA and high-throughput hybridization and analysis on an array of microarrays by using generic tag-arrays. This methodology is depicted in FIG. 13.

Materials and Methods

Microarray Preparation and Spatial Separation of Samples

Amino-linked oligonucleotide capture probes suspended at a concentration of 20 µM in 150 mM sodium phosphate pH 8.5 and 0.06% sarkosyl were spotted using a GMS 417 arrayer (Affymetrix, USA) on 3D-link activated slides (Motorola Life Sciences, IL, USA). Sarkosyl was added to the spotting solution as it improved spot uniformity. The primers were printed in 16 clusters on the microscope slide (an array of arrays) with each cluster containing one duplicate of each primer. The sequence of these tags on the glass slides is listed in Table 1. The sequence of all these unique sequence tags was taken from www.genome.wi.mit.edu.

The distance between the spots was 250 µM and the spot diameter was approximately 200 µM. The clusters were positioned in two columns of eight rows each with a 9 mm distance between cluster centers. After printing, the arrays were incubated overnight in a humid chamber followed by post coupling as outlined by the manufacturer. Briefly the slides were incubated at 50° C. for 15 minutes in blocking solution (50 mM ethanol amine, 0.1M Tris pH 9 and 0.1% SDS), rinsed twice in $H_2O$ and washed with 4×SSC/0.1% SDS (pre-warmed to 50° C.) for 15 to 60 minutes. The arrays were then rinsed in $H_2O$ and dried by centrifugation for 3 minutes at 800 rpm.

The 16 clusters on the microarray slide were separated during hybridization by using a silicone mask (Elastosile 601 A/B Wacker Chemie GmbH, Munich, Germany) molded in a 96 well plate and excised to fit the slide. A Custom made rack was used to press the silicone firmly to the slide and keep it in place during the reactions.

Tagged (Barcoded) Type-specific/Allele Specific Extension Primers

The DNA sequence of the L1 region of the high-risk (16, 18, 31, 33, 35, 39, 45, 51, 52, 58, 59, 66, 68, 69) and low-risk HPV (6, 11, 34, 40, 42, 43, 44) types were aligned for specific primer design. Three regions (in the 150 base pair long PCR amplified sequence) with high heterogeneity between different HPV types were selected to design base-specific extension primers. The distance between these oligonucleotides was 10 to 11 bases to allow elongation by DNA polymerase. A database search (BLAST from National Center for Biotechnology Information NCBI) showed matches with the corresponding HPV types. A total of 30 base-specific extension primers (three oligonucleotides per HPV type) were designed for the 10 HPV types investigated in this study (HPV-6, 11, 16, 18, 31, 33, 40, 45, 72 and 73). Each oligonucleotide contained a tag (barcode) at its 5'-end. The HPV base-specific extension oligonucleotides with 5'-terminus tags are listed in Table 9. The oligonucleotides were synthesized by MWG-biotech, Germany. A comparison of Table 7 and Table 8 shows that each oligonucleotide tag on the glass slide is complementary to one of the tags on the 5'-terminus of the base-specific extension primers.

TABLE 8

List of sequence tags and base-specific extension primers

| | |
|---|---|
| HPV6(1)LT2 | GCAGATCAATTAATACGATACCTGCG-ACGCAGTACCAACATGACAT |
| HPV6(2)LT3 | GGTTCTGTTCTTCGTTGACATGAGG-CGTAACTACATCTTCCACA |
| HPV6(3)LT4 | TTAGTCTCCGACGGCAGGCTTCAAT-TGATTATAAAGAGTACATGC |
| HPV11(1)LT5 | CTGTGACAGAGCCAACACGCAGTCT-ACGCAGTACAAATATGACAC |
| HPV11(2)LT6 | CCTGGTGGTTGACTGATCACCATAA-TGTGTCTAAATCTGCTACA |
| HPV11(3)LT7 | GCATGTATAGAACATAAGGTGTCTC-AGATTATAAGGAATACATGC |
| HPV16(1)LT8 | GCTAGATGAAGAGCAAGCGCATGGA-ACGCAGTACAAATATGTCAT |
| HPV16(2)LT9 | TACAACCGACAGATGTATGTAAGGC-CATATCTACTTCAGAAACT |
| HPV16(3)LT10 | TTCAATCTGGTCTGACCTCCTTGTG-TACTAACTTTAAAGAGTACC |

TABLE 8-continued

List of sequence tags and base-specific extension primers

```
HPV18(1)LT11  ACACGATGTGAATATTATCTGTGGC-TCGCAGTACCAATTTAACAA

HPV18(2)LT12  TTGAAGTTCGCAGAATCGTATGTGT-TACACAGTCTCCTGTACCT

HPV18(3)LT13  AACGTCTGTTGAGCACATCCTGTAA-TGCTACCAAATTTAAGCAGT

HPV31(1)LT14  GGCAACTCATGCAATTATTGTGAGC-ACGTAGTACCAATATGTCTG

HPV31(2)LT15  CCAGAAGTATATTAATGAGCAGTGCAG-AATTGCAAACAGTGATACT

HPV31(3)LT16  AAGCAGTCTGTCAGTCAGTGCGTGAA-TAGTAATTTTAAAGAGTATT

HPV33(1)LT17  AATGATGCTCTGCGTGATGATGTTG-TCGCAGTACTAATATGACTT

HPV33(2)LT18  AATACACGAAGGAGTTAGCTGATGC-AGTAACTAGTGACAGTACA

HPV33(3)LT19  GCTGTTAATCATTACCGTGATAACGCC-GAATTTTAAAGAATATATAA

HPV40(1)LT20  GCGGAACGGTCAGAGAGATTGATGT-TCGTAGCACTAATTTAACCT

HPV40(2)LT21  GTTATGGTCAGTTCGAGCATAAGGC-CACACAGTCCCCCACACCA

HPV40(3)LT22  TTACCTATGATTGATCGTGGTGATATCCG-TAACAGTAATTTCAAGGAAT

HPV45(1)LT23  GCTGTGGCATTGCAGCAGATTAAGG-CCGCAGTACTAATTTAACAT

HPV45(2)LT24  TGACGTCATTGTAGGCGGAGAGCTA-TACACAAAATCCTGTGCCA

HPV45(3)LT25  TCAATAATCAACGTAAGGCGTTCCT-TCCTACTAAGTTTAAGCACT

HPV72(1)LT26  TTATCGGCTACATCGGTACTGACTC-TCGCAGTACTAATGTAACTA

HPV72(2)LT27  CCATTATCGCCTGGTTCATTCGTGA-CACAGCGTCCTCTGTATCA

HPV72(3)LT28  GGCGTACCTTCGCGGCAGATATAAT-TTCTAATTTTCGTGAGTATC

HPV73(1)LT29  AACTGAGCCGTAGCCACTGTCTGTCC-TAGAAGCACTAATTTTTCTG

HPV73(2)LT30  GTTGTGCTGAATTAAGCGAATACCG-TACACAGGCTAGTAGCTCT

HPV73(3)LT31  TTATATCTGCACAACAGGTAAGAGCTGCCAACTCTAATTTTAAGG
```

HPV Patient Samples and Plasmids

The material for the study consisted of cervical scrapes taken from the ecto-endo cervix by CytoBrush® of ten women diagnosed with either primary invasive cervix cancer (Radiumhemmet, Karolinska Hospital) or abnormal cytology diagnosed through the Swedish national cervix cancer screening program (Gynecology Clinic, Karolinska Hospital). The samples were collected in sterile phosphate buffered saline (pH 8.0). DNA extraction was performed using the QIAmp® System (Qiagen Inc. Valencia, Calif. USA) according to the instructions described in the kit. The DNA was dissolved in 200 µl of Tris-EDTA buffer pH 7.4.

HPV whole genomic plasmids for types 6, 11, 16, 18, 33, 40, 45, 72 and 73 were used for this study.

PCR Amplification

The DNA amplifications were performed in 50 µl mixtures consisting of 5 µl DNA sample, 5 µl PCR buffer (Perkin Elmer, Norwalk, Conn., USA), 3.5 mM $MgCl_2$, 0.2 mM dNTP, 25 pmol GP5+/6+ primer set and 1 U of AmpliTaq$^R$ (Perkin Elmer). The GP6+ primer was biotinylated. The thermocycler temperature program consisted of denaturation at 94° C. for 1 minute, annealing at 38° C. for 1 minute, extension at 71° C. for 2 minutes for 40 cycles. Each PCR was initiated by a 4 minutes denaturation step at 94° C. and finished by a 4 minutes extension step at 71° C. A Perkin Elmer 9700 thermocycler was used for all amplifications. The PCR products generated a150 base pair DNA fragment.

Sample Preparation and Extension Reaction

Five micro-liters of the PCR products were immobilized onto streptavidin-coated super paramagnetic beads (Dynabeads M280; Dynal, Oslo, Norway) and single-stranded DNA was obtained by alkali elution of the non-biotinylated strand. This and other procedures described in this section were performed by a Magnetrix 1200 robot (Magnetic Biosolutions, Stockholm, Sweden). The supernatant was then discarded and the capture strand was resolved in a 60 µl solution containing $H_2O$, 10× annealing buffer (100 mM Tris-acetate pH 7.75, 20 mM Mg-acetate) and all 30 HPV-base-specific extension primers (6 pmol/each primer) were added and annealed to the captured strand. The annealing was performed at 70° C. for 1 minute and then at room temperature for 5 minutes. As mentioned above, each HPV oligonucleotide contained a specific tag (a barcode) at its 5'-end. The base-specific primers with 5'-terminus tags are listed in Table 7 in Example 3. After annealing, the unbound oligonucleotides and excess matched oligonucleotides were removed and the immobilized single-stranded DNA with annealed primers was mixed with Proteinase K and dye-labeled dNTPs (Cy5 C and Cy5 T). This mixture was then incubated at 50° C. and then DNA polymerase (Klenow polymerase) was added into this mixture. After polymerization, the enzymes and dNTPs were discarded and immobilized DNA was washed. The immobilized DNA was then treated with alkali (0.1 M) and the supernatant (the PrASE product) was neutralized with HCl (0.1 M). The PrASE products (each containing a specific tag at the 5'-terminus) were then hybridized to glass slides with generic tag-arrays.

Data Acquisition

Following the hybridization, data was obtained by scanning slides with a GMS 428 scanner (Affymetrix, USA). Data was extracted into a TIFF file and analyzed in GenePix 4.0, (Axon instruments, USA). All spots were manually inspected prior to data extraction. The fluorescence intensities (medians after background subtraction) were calculated by the GenePix 4.0 software and the data was then analyzed in Excel. As mentioned above, one slide was divided into 16 clusters and each cluster contained one duplicate spot of each tag oligonucleotide and thus the mean value of these spots was used to analyze the data for each sample.

Pyrosequencing™ Technology and Sanger Dideoxy Sequencing

All the results were sequenced and confirmed by Pyrosequencing™ technology and Sanger DNA sequencing (cycle sequencing). Pyrosequencing™ was performed on a Luc 96 (Pyrosequencing™ AB, Uppsala, Sweden) and conventional Sanger DNA sequencing was performed on an ABI 3700 DNA Analyzer (Applied Biosystems, Foster City, Calif.) using the BigDye terminator chemistry according to the manufacturer's manual.

Results and Discussion

Here we present a technology for accurate, fast and high throughput genotyping of Human papillomaviruses (HPV). We have used HPV as a model system but this technique represents a universal approach and is applicable for genotyping of other viral and microbial sequences. However, our choice of HPV genotypes was only based on the availability of HPV DNA plasmids and patient specimens. Human papillomaviruses (HPV) are DNA viruses that are believed to be an important contributing factor in the etiology of certain benign and malignant tumor lesions in human such as cervical cancer.

The genome of different HPV types is very variable and this has caused problems in genotyping of these heterogeneous sequences. There are different techniques for HPV detection and genotyping, all with their advantages and disadvantages. Many of these techniques rely on type-specific hybridization assays. Nevertheless, type-specific hybridization (often, when the species has two chromosomes, referred as allele-specific hybridization) is hampered by cross-reactivity (non-specific hybridization) giving false positive results. This non-specific hybridization is specially a problem in high throughput microarray based analysis. In the microarray based approaches, small amount of discriminating probes (type-specific oligonucleotides) are spotted and immobilized on the glass slides and an excess of mobile target DNA is allowed to hybridize to these probes. Theoretically, the target DNA will hybridize to perfect matched probe(s) and by using stringent temperature conditions, hybridization to mismatched probes is avoided. However, in practice, there are extremely small differences in the duplex stability between a perfect match and a mismatch at one base which limits the use of this technology. In addition, since the discriminating probes are immobilized, a perfect match probe has no chance to influence hybridization of the mobile (in solution) target DNA to the mismatch probes.

In spite of that, the first step in our approach utilizes specific hybridization of oligonucleotides to the target DNA. DNA sequence of the L1 region of 10 investigated HPV types (HPV 6, 11, 16, 18, 31, 33, 40, 45, 72 and 73) were aligned for specific primer design. Three regions in a 150 base pair long PCR amplified sequence with high heterogeneity between different HPV types were selected to design type-specific oligonucleotides. The distance between these oligonucleotides was 10 to 11 bases. Thus, a total of 30 type-specific oligonucleotides (three oligonucleotides per HPV type) were designed. One tenth of the PCR product with a biotin labeled primer was immobilized onto streptavidin-coated beads (Dynal, Oslo, Norway) and single-stranded DNA was obtained by alkali elution of the non-biotinylated strand. A relatively high concentration (6 pmol) of each of the type-specific oligonucleotides was then added in a multiplex fashion to anneal to the captured single-stranded target DNA. The solution was heated to 70° C. and then cooled to room temperature. The main difference between this approach and conventional type-specific hybridization assays is that in our approach the mobile type-specific probes (with high concentrations compared to the target DNA) are competing to hybridize to the same DNA sequence. Obviously, when the temperature is reduced from 70° C., the oligonucleotides (or the probes) that are completely matched to the target DNA will have favorable hybridization kinetics compared to the mismatched probes and thus the mismatched probes are out-competed. After this, at lower temperature (as low as room temperature) the mismatched probes would have the opportunity to hybridize non-specifically but the target is already occupied by the matched probes. After annealing, the unbound oligonucleotides and the excess matched oligonucleotides are discarded. In addition, in order to be able to distinguish which of the multiplexed annealed base-specific oligonucleotides have hybridized to the target DNA, each oligonucleotide contain a specific and unique tag (barcode) at its 5'-terminus functioning as the signature of that oligonucleotide.

In spite of improvements to allele-specific hybridization assays by employing the multiplex competitive approach, this method may still give rise to false positive signals. In a study performed on HIV-1 as a model system for investigation of the effects of internal primer-template mismatches (Christopherson et al, Nucleic Acids Research, 1997, Vol. 25, No. 3, 654-658), the authors concluded that the presence of two to four mismatches in the primer-template did not have a significant effect on PCR. However, they observed that the presence of five or more mismatches reduced the PCR products yield by at least 20-fold. This may indicate that despite the kinetic nature of multiplex competitive type-specific hybridization (MCTSH), some non-specific hybridization may still occur. Thus, we sought further to modify the MCTSU approach to provide a more accurate and specific assay. In particular, we have combined MCTSH with an enzymatic approach to provide an accurate viral genotyping technique. For this purpose, an base-specific primer extension assay was employed. Base-specific extension methods requiring only a single detection reaction are based on extension of base-specific primers that differ at their 3'-terminus nucleotide (or at other positions), defining the allelic variants. Despite its simplicity, the use of base-specific extension technologies has greatly been hampered by the poor discrimination property of the DNA polymerases, resulting in certain mismatches being poorly discriminated. However, we have previously shown that DNA polymerases extend the mismatched primer-templates (in the presence of nucleotides) with slower reaction kinetics in comparison to extension of the matched primer-template configurations.

Figure 14:
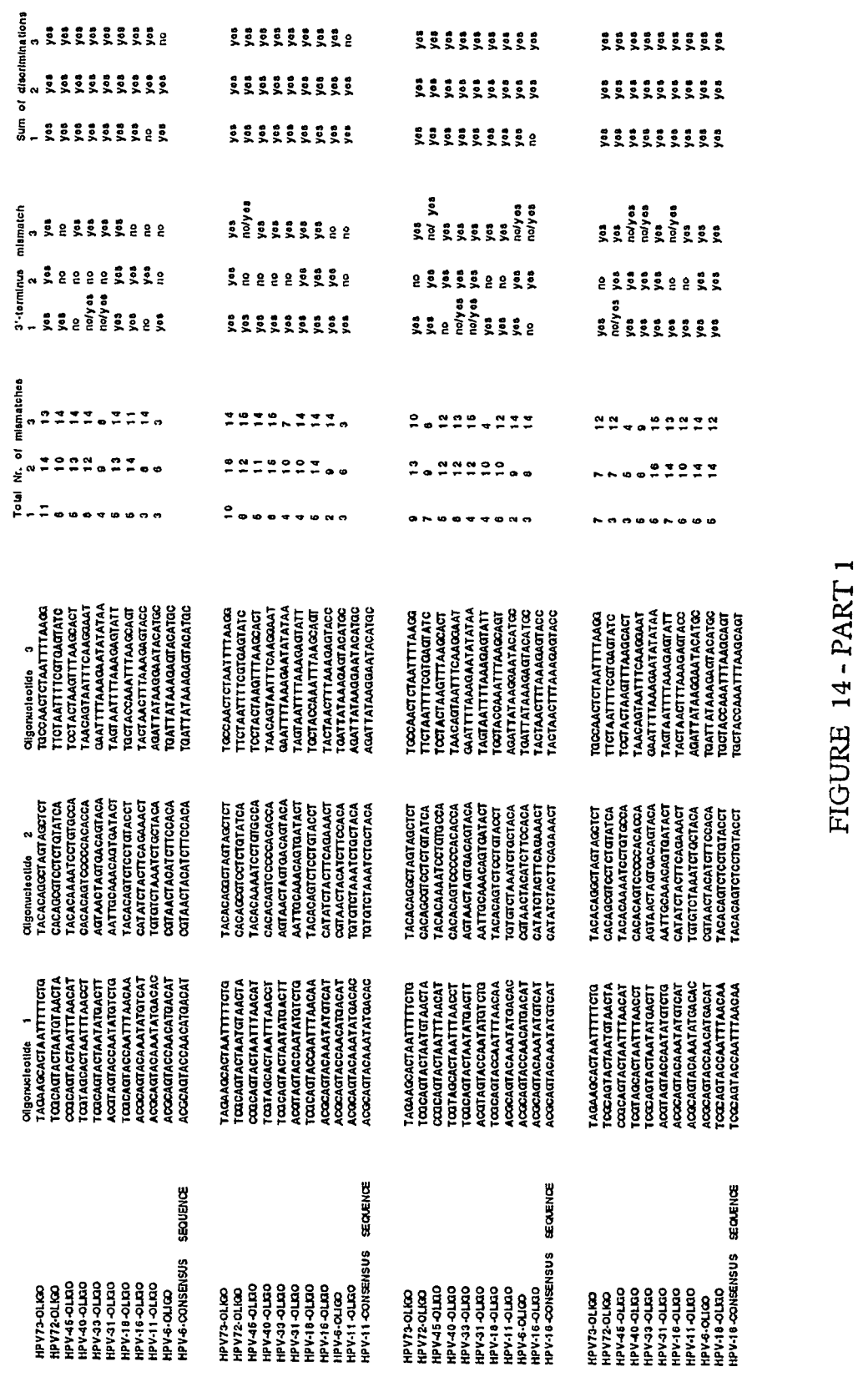
Figure 14:
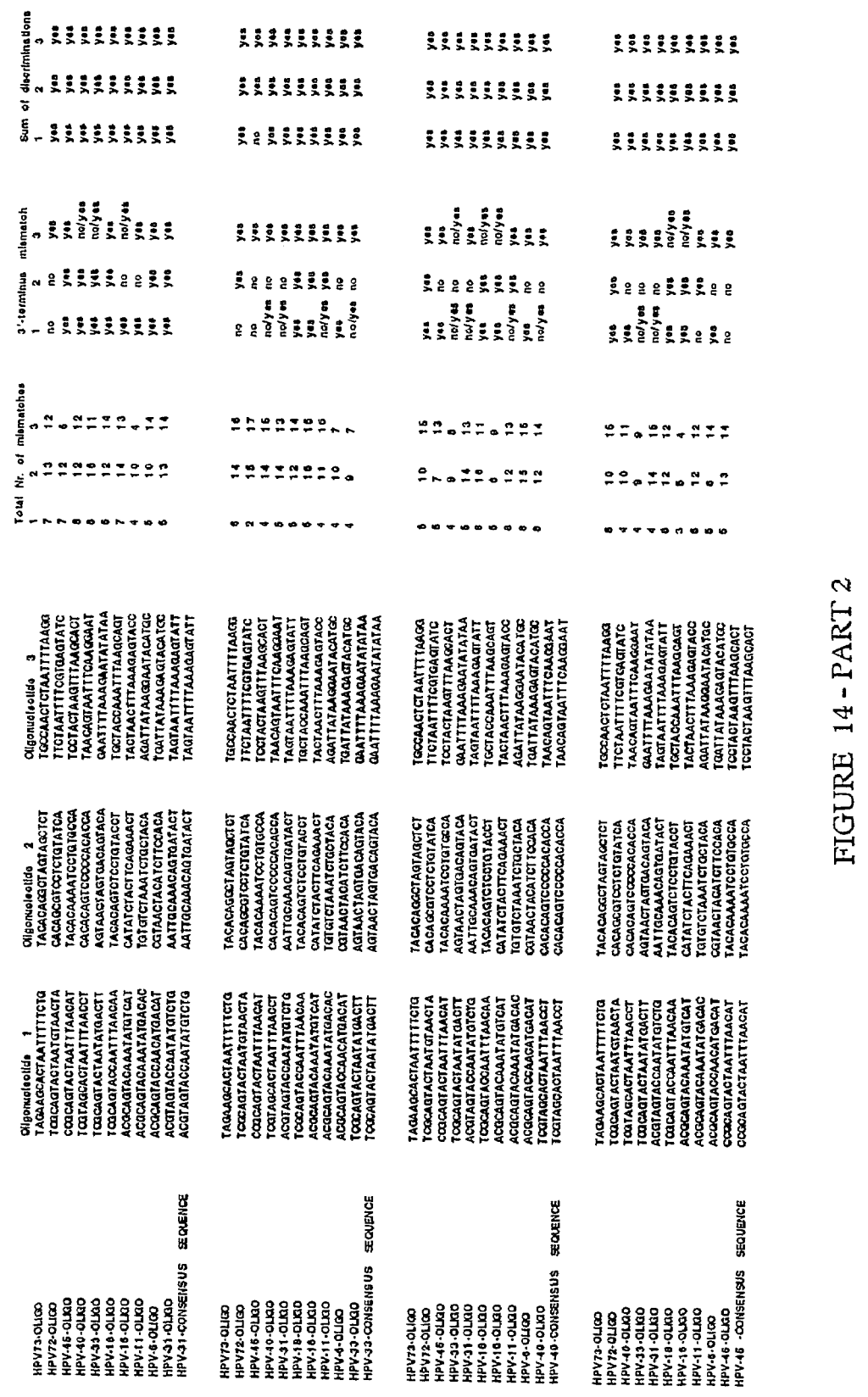

As mentioned above, DNA sequence of the L1 region of 10 HPV types were aligned for primer design of three regions with high heterogeneity. The first step in the experimental design was a theoretical simulation of the events. FIG. 14 illustrates this simulation. As shown in FIG. 14, the consensus sequence of the three regions of all 10 investigated types is given and just above these the sequence of 10 oligonucleotides is indicated. One of these oligonucleotides (for each region) forms a complete match to the consensus sequence and is always indicated as the first oligonucleotide above the consensus sequence. Nine oligonucleotides that correspond to the other HPV types are listed above the complete matched oligonucleotide and contain different number of mismatches when compared to the consensus sequence. The columns 1, 2 and 3 in the right correspond to the number of mismatches to the template (1), if there is a 3'-terminus mismatched primer-template (2) and sum of the discriminations (3). Obviously, a mismatch at or near the 5'-end of an oligonucleotide will have much less consequences on hybridization efficiency than one in the middle. And as the number of mismatches to the template differ and occur in different positions, these may have completely different influence on the competitive hybridization. Thus, in this simulation, irrespective of position of the mismatches, when the number of mismatches were less or equal to 4 the effect of mismatches in the competitive hybridization were assumed to be minute. Realistically, in the competitive hybridization, less than four mismatches should be enough to discriminate a complete match oligonucleotide from mismatching oligonucleotides but this assumption was kept to challenge the technique. The second discriminating factor in this technique is proteinase-mediated allele-specific extension (PrASE) assay and in the second column, the presence or absence of 3'-terminus mismatching base(s) is indicated by yes or no respectively. However, we have previously noticed that in many cases presence of a mismatch in a penultimate base hinders the primer extension and therefore in such cases the discrimination by PrASE was cautiously indicated by no/yes. When PrASE is not able to influence the process of type discriminations (a consequence of lack of 3'-terminus mismatches), the term no is used. As it is illustrated, high number of flagged discriminations are indicated in the first two columns. Nevertheless, in the third column when sum of discriminations is evaluated, only five combinations are flagged by no. The evaluation has been based on combining the discrimination factor of MCTSH (the first column) with PrASE (the second column). Four scenarios were possible by this combination. First, when the number of mismatches in MCTSH is indicated by more than 4 internal oligonucleotide-template mismatches and PrASE results in yes (presence of one or more primer-template 3'-terminus mismatches) the sum of discriminations will be indicated by yes. Second, when one of the discriminating factors is flagged (by no or has 4 or less internal mismatches) but the other one fulfills the criteria for correct genotyping, the sum of discriminations will be yes. Third, when MCTSH is flagged by 4 or less internal mismatches and PrASE is no/yes the resulting sum of discriminations has been assumed to be yes. The argument here was that the presence of a mismatch in a penultimate base hinders a proper primer extension (at least in many cases) and this in combination with 2 to 4 other internal mismatches should provide discrimination. The fourth scenario is when both factors fail to fulfill correct genotyping criteria and consequently the sum of discriminations will also fail and is notified by a no flag. The results of this simulation indicate that the use of three regions may be overflowing. However, in order to provide an accurate genotyping method and to be prepared for unpredicted problems that have not been taken in consideration in our simulation, the assay was performed with the use of three oligonucleotide sets for three regions. Thus, the use of three oligonucleotide sets provides an extreme accurate genotyping result. If one of the primers fails and causes non-(type)specific signal, the other two will be discriminated and will not contribute to non-(type)specific signals. In addition, in order to consider a genotype result as true result, all three primers have to give extension signal.

What is claimed is:

1. A method of detecting a base at a pre-determined position in a nucleic acid molecule, which comprises performing enzymatic oligomer elongation reactions using base-specific detection oligomers, with each oligomer being specific for a particular base at the predetermined position, and comparing the enzymatic oligomer elongation reactions to determine which base is present at the position, wherein a protein degrading enzyme is present during the enzymatic oligomer elongation reactions at a concentration such that mismatched enzymatic elongation reactions are eliminated or reduced.

2. The method of claim 1 wherein the protein degrading enzyme is Proteinase K.

3. The method of claim 1 wherein the base-specific oligomers have a base-specific position at the 3' end, the 3'-1 position or the 3'-2 position.

4. The method of claim 1 wherein the base-specific oligomers are tagged.

5. The method of claim 4 wherein the tag is a barcode.

6. The method of claim 1 wherein the base-specific oligomers are labelled, directly or indirectly.

7. The method of claim 1 wherein the method is performed in a solid phase microarray format.

8. The method of claim 7 wherein the target nucleic acid molecule or base-specific oligomers are hybridized to the microarray after the enzymatic oligomer elongation reaction.

9. The method of claim 8 wherein the hybridization occurs to immobilized complementary oligonucleotides on the microarray.

10. The method of claim 7 wherein the base-specific oligomers or the nucleic acid molecule are immobilized in the array prior to the enzymatic oligomer elongation reactions.

11. The method of claim 7 wherein multiple enzymatic oligomer elongation reactions are carried out simultaneously or in parallel.

12. The method of claim 1 wherein the base-specific oligomers are annealed to the nucleic acid molecules under competitive conditions wherein the base-specific oligomers are competing to anneal to the nucleic acid molecule.

13. The method of claim 12 wherein the annealing step is performed at 50-95° C. followed by cooling to 15-50° C.

14. The method of claim 1 wherein the enzymatic elongation reactions are compared by determining the efficiency of the enzymatic oligomer elongation reaction for each of the base-specific oligomers and comparing them.

15. The method of claim 1 wherein the enzymatic oligomer elongation reactions are catalyzed by a polymerase enzyme.

16. The method of claim 15 wherein the base-specific oligomers are primers, and the primers are elongated via the addition of nucleotides.

17. The method of claim 16 wherein the nucleotides are labelled or are intermediary nucleotides to which a label can be attached.

18. The method of claim 16 wherein primer elongation is determined by detecting or monitoring pyrophosphate release.

19. The method of claim 16 wherein a fluorescently labelled probe is hybridized to the nucleic acid molecule prior to elongation of the primers, and elongation is detected via an increase in fluorescence level.

20. The method of claim 1 wherein the enzymatic oligomer elongation reactions are catalyzed by a ligase enzyme.

21. The method of claim 20 wherein the base-specific oligomers are padlock probes.

22. The method of claim 20 wherein the base-specific oligomers are probes, and a second probe is provided which hybridizes to the nucleic acid molecule next to the base-specific oligomers.

23. The method of claim 22 wherein the junction between the base specific probes and second probe is at the pre-determined position.

24. The method of claim 22 wherein the enzymatic ligation detection reactions are determined via detecting the size of the oligomer.

25. The method of claim 22 wherein the base-specific probes are tagged with a label and the second probe is tagged with a hook.

26. The method of claim 1 wherein 2, 3 or 4 base specific oligomers are used.

27. The method of claim 26 wherein 4 base specific oligomers are used to detect an unknown base at the pre-determined position.

* * * * *